(12) United States Patent
Herman et al.

(10) Patent No.: US 6,780,987 B1
(45) Date of Patent: Aug. 24, 2004

(54) β-CAP73 CONTROL OF NORMAL AND ABNORMAL CELL MIGRATION

(75) Inventors: Ira Herman, Newton, MA (US); Alice Y. Welch, Brookeville, MD (US)

(73) Assignee: Trustees of the Tufts College, Boston, MA (US)

( * ) Notice: Subject to any disclaimer, the term of this patent is extended or adjusted under 35 U.S.C. 154(b) by 0 days.

(21) Appl. No.: 09/750,590

(22) Filed: Dec. 28, 2000

Related U.S. Application Data

(63) Continuation-in-part of application No. 09/733,818, filed on Dec. 8, 2000, now abandoned.
(60) Provisional application No. 60/170,182, filed on Dec. 10, 1999.

(51) Int. Cl.[7] .................. C07H 21/04; A61K 48/00; C12Q 1/68

(52) U.S. Cl. .................. 536/23.5; 536/23.1; 514/44; 435/6

(58) Field of Search .................. 536/23.5, 23.1; 514/44; 435/6

(56) References Cited

U.S. PATENT DOCUMENTS 5,744,300 A * 4/1998 Linskens et al. .................. 435/6

FOREIGN PATENT DOCUMENTS

WO  WO 98/49302  * 11/1998

OTHER PUBLICATIONS

Wilkin et al., Identification and characterization of novel genes modulated in the thyroid of dogs treated with methimazole and propylthiouracil, 1996, The Journal of Biological Chemeistry.*
Allen PG, et al. "Phalloidin binding and rheological differences among actin isoforms." *Biochemistry.* Nov. 12, 1996;35(45):14062–9.
Arber S, et al. "Regulation of actin dynamics through phosphorylation of cofilin by LIM–kinase", *Nature.* Jun. 25, 1998;393(6687):805–9.
Aspenstrom, P, et al. "Two GTPases, Cdc42 and Rac, bind directly to a protein implicated in the immunodeficiency disorder Wiskott–Aldrich syndrome". *Curr. Biol.* Jan. 1, 1996;6(1):70–5.
Ayscough KR. "In vivo functions of actin–binding proteins." *Curr Opin Cell Biol.* Feb. 1998;10(1):102–11.
Bassell GJ, et al. "Sorting of beta–actin mRNA and protein to neurites and growth cones in culture." *J. Neurosci.* Jan. 1, 1998;18(1):251–65.
Bea F, et al. "Cardiac alpha–actin in smooth muscle cells: detection in umbilical cord vessels and in atherosclerotic lesions." *Basic Res Cardiol.* Apr. 2000;95(2):106–13.
Brault V, et al. "Substitution of flight muscle–specific actin by human (beta)–cytoplasmic actin in the indirect flight muscle of Drosophila." *J Cell Sci.* Nov. 1999;112 ( Pt 21):3627–39.
Carlier MF. "Control of actin dynamics." *Curr Opin Cell Biol.* Feb. 1998;10(1):45–51.
Clowes, AW, et al. "Arterial smooth muscle cells in vivo: relationship between actin isoform expression and mitogenesis and their modulation by heparin." *J. Cell Biol.* Nov. 1988;107(5):1939–45.
Dugina, V, et al. "Rat fibroblasts cultured from various organs exhibit differences in alpha–smooth muscle actin expression, cytoskeletal pattern, and adhesive structure organization." *Exp Cell Res.* Feb. 1, 1998;238(2);481–90.
Fyrberg EA, et al. "The actin genes of Drosophila: a dispersed multigene family." *Cell.* Feb. 1980;19(2):365–78.
Genbank Accession AB046781, *Homo Sapiens* mRNA for KIIA1561 protein, partial cds.
Genbank Accession X99145, Canis familiaris mRNA for C3VS protein.
Gunning, P, et al. "Actin and tropomyosin isoforms in morphogenesis." *Anat Embryol (Berl).* Apr. 1997;195(4):311–5.
Hannan AJ, et al. "Structural compartments within neurons: developmentally regulated organization of microfilament isoform mRNA and protein." *Mol Cell Neurosci.* Aug. 1998;11(5–6):289–304.
Herman IM. Actin isoforms. Curr Opin Cell Biol. Feb. 1993; 5(1):48–55.
Herman IM, et al. "Comparison of purified anti–actin and fluorescent–heavy meromyosin staining patterns in dividing cells." *J Cell Biol.* Mar. 1979;80(3);509–20.
Herman IM, et al. "Microvascular pericytes contain muscle and nonmuscle actins." *J. Cell Biol.* Jul. 1985;101(1):43–52.
Hoock TC, et al. "Beta actin and its mRNA are localized at the plasma membrane and the regions of moving cytoplasm during the cellular response to injury". *J. Cell Biol.* Feb. 1991;112(4):653–64.
Janmey PA, et al. "Modulation of gelsolin function by phosphatidylinositol 4,5–biphosphate." *Nature.* Jan. 22–28, 1987;325(6102):362–4.

(List continued on next page.)

*Primary Examiner*—Anne-Marie Falk
*Assistant Examiner*—Daniel M. Sullivan
(74) *Attorney, Agent, or Firm*—Lahive & Cockfield, LLP; Giulio A. DeConti, Jr.; Elizabeth A. Hanley

(57) ABSTRACT

The invention provides isolated nucleic acids molecules, designated βCAP73 nucleic acid molecules, which encode a novel actin binding protein. The invention also provides antisense nucleic acid molecules, recombinant expression vectors containing βCAP73 nucleic acid molecules, host cells into which the expression vectors have been introduced, and nonhuman transgenic animals in which a βCAP73 gene has been introduced or disrupted. The invention still further provides isolated βCAP73 proteins, fusion proteins, mutant proteins, antigenic peptides and anti-βCAP73 antibodies. Diagnostic and therapeutic methods utilizing compositions of the invention are also provided.

3 Claims, 19 Drawing Sheets

OTHER PUBLICATIONS

Kimura K, et al. "Hypertensive glomerular damage as revealed by the expression of alpha–smooth muscle actin and non–muscle myosin." *Kidney Int Suppl.* Jun. 1996;55:S169–72.

Kislauskis EH, et al. "Isoform–specific 3'–untranslated sequences sort alpha–cardiac and beta–cytoplasmic actin messenger RNAs to different cytoplasmic compartments". *J Cell Biol.* Oct. 1993;123(1):165–72.

Kislauskis EH, et al. Sequences responsible for intracellular localization of beta–actin messenger RNA also affect cell phenotype. J. Cell Biol. Oct. 1994;127(2):441–51.

Kureishi, Y, et al. "Rho–associated kinase directly induces smooth muscle contraction through myosin light chain phosphorylation." *J Biol Chem.* May 9, 1997;272(19):12257–60.

Lassing I, et al. "Specificity of the interaction between phosphatidylinositol 4,5–bisphosphate and the profilin:actin complex" J Cell Biochem. Jul. 1988;37(3):255–67.

Meagher RB, et al. "Isovariant dynamics expand and buffer the responses of complex systems: the diverse plant actin gene family" *Plant Cell.* Jun. 1999;11(6):995–1006.

Miki H, et al. "N–WASP, a novel actin–depolymerizing protein, regulates the cortical cytoskeletal rearrangement in a PIP2–dependent manner downstream of tyrosine kinases." *EMBO J.* Oct. 1, 1996;15(19):5326–35.

Otey CA, et al. "Immunolocalization of muscle and non-muscle isoforms of actin in myogenic cells and adult skeletal muscle." *Cell Motil Cytoskeleton,* 1988;9(4):337–48.

Otey CA, et al. "Immunolocalization of the gamma isoform of nonmuscle actin in cultured cells." *J Cell Biol.* May 1986;102(5):1726–37.

Potter DA, et al. "Calpain regulates actin remodeling during cell spreading". *J Cell Biol.* May 4, 1998;141(3):647–62.

Pinder JC, et al. "Concentrated Tris solutions for the preparation, depolymerization, and assay of actin: application to erythroid actin" *Anal Biochem.* Mar. 1, 1995;225(2):291–5.

Sanders LC, et al. "Inhibition of myosin light–chain kinase by p21–activated kinase." *Science.* Mar. 26, 1999;283(5410):2083–5.

Schafer, DA, et al. "Dynamics of capping protein and actin assembly in vitro: uncapping barbed ends by polyphosphoinositides." *J. Cell Biol.* Oct. 1996; 135(1):169–79.

Schevzov G, et al. "High level expression of transfected beta– and gamma–actin genes differentially impacts on myoblast cytoarchitecture." *J Cell Biol.* May 1992;117(4);775–85.

Schroer E, et al. "Purification and characterization of a protein from chicken gizzard, which inhibits actin polymerization." *Eur J Biochem.* Dec. 16, 1985;153(3):515–20.

Shuster CB, et al. "Indirect association of ezrin with F–actin: isoform specificity and calcium sensitivity." *J Cell Biol.* Mar. 1995;128(5):837–48.

Shuster CB, et al. "Beta cap73: a novel beta actin–specific binding protein". *Cell Motil Cytoskeleton.* 1996;35(3):175–87.

Symons, M, et al. "Wiskott–Aldrich syndrome protein, a novel effector for the GTPase CDC42Hs, is implicated in actin polymerization." *Cell.* Mar. 8, 1996;84(5):723–34.

The TIGR Human Gene Index (HGI) HGI THC Report: THC186491, http://www.tigr.org/docs/scpipts/tc_report.pl.

The TIGR Human Gene Index (HGI) HGI THC Report: THC244788, http://www.tigr.org/docs/scpipts/tc_report.pl.

The TIGR Human Gene Index (HGI) HGI THC Report: THC213238, http://www.tigr.org/docs/scpipts/tc_report.pl.

von Arx P, et al. "Dominant negative efect of cytoplasmic actin isoproteins on cardiomyocyte cytoarchitecture and function." *J. Cell Biol.* Dec. 1995;131(6 Pt 2):1759–73.

Watanabe N, et al. "p140mDia, a mammalian homolog of *Drosophila diaphanous*, is a target protein for Rho small GTPase and is a ligand for profilin." *EMBO J.* Jun. 2, 1997;16(11):3044–56.

Yang N, et al. "Cofilin phosphorylation by LIM–kinase 1 and its role in Rac–mediated actin reorganization." *Nature.* Jun. 25, 1998;393(6687):809–12.

Yao X, et al. "Erzin–calpain I interactions in gastric parietal cells." *Am J Physiol.* Jul. 1993;265(1 Pt 1):C36–46.

* cited by examiner

```
cagtgttgag gcggcaggat gtagagtgct gttcaagctt tccagtggag tccccgaaaa  60
gggaaggcag agaaagacat cttctaaata acaaatagga ggagttacag tacctgactt 120
ggggctgctc ttaatcaagt gctgccgctg caaggaagat aattttcaag cgttatgaag 180
gcggagaagg attccgaaga cgaagaaaat atccttagag atccaagcta agtgtagtgc 240
agcatgaaga ttgcagaaca ggaagagttc taagaagaag gactgagtca ctagttagga 300
gtctctctga gggctggctt tgtgagccac agtgatttgt aacttaatgc gaactaattt 360
gctgttagca acaagaaact aaatcctgtc t atg atg agc tgt tgg ttt tct   412
                                  Met Met Ser Cys Trp Phe Ser
                                   1                5
```

```
tgt gct cct aag aac aga caa gca gca gat tgg aac aaa tac gat gac   460
Cys Ala Pro Lys Asn Arg Gln Ala Ala Asp Trp Asn Lys Tyr Asp Asp
         10              15                  20 cga ttg atg aga gca gca gaa agg gga gat gta gaa aaa gtg tcc tca   508
Arg Leu Met Arg Ala Ala Glu Arg Gly Asp Val Glu Lys Val Ser Ser
     25                  30                  35 atc ctt gct aaa aag gga gtc aat cca ggc aag cta gat gta gaa ggc   556
Ile Leu Ala Lys Lys Gly Val Asn Pro Gly Lys Leu Asp Val Glu Gly
 40                  45                  50                  55 aga tct gcc ttt cat gtt gtg gcc tca aag gga aat ctt gag tgt ttg   604
Arg Ser Ala Phe His Val Val Ala Ser Lys Gly Asn Leu Glu Cys Leu
                 60                  65                  70 aat gcc atc ctc ata cat gga gtt gat att aca acc agt gac acc gca   652
Asn Ala Ile Leu Ile His Gly Val Asp Ile Thr Thr Ser Asp Thr Ala
             75                  80                  85 gga agg aat gct ctt cac ctg gct gca aag tat ggg cat gca ctg tgt   700
Gly Arg Asn Ala Leu His Leu Ala Ala Lys Tyr Gly His Ala Leu Cys
         90                  95                 100 cta caa aaa ctt cta cag tac aat tgt ccc act gaa cat gta gac ctg   748
Leu Gln Lys Leu Leu Gln Tyr Asn Cys Pro Thr Glu His Val Asp Leu
     105                 110                 115 cag gga aga act gca ctt cat gat gca gct atg gca gac tgt cct tct   796
Gln Gly Arg Thr Ala Leu His Asp Ala Ala Met Ala Asp Cys Pro Ser
 120                 125                 130                 135 agc ata cag ctg ctc tgc gac cat ggg gcc tcg gtg aat gcc aaa gat   844
Ser Ile Gln Leu Leu Cys Asp His Gly Ala Ser Val Asn Ala Lys Asp
             140                 145                 150
```

Fig. 4-1

```
gta gat ggg cgg aca cca ctt gtt ctg gct acc cag atg tgt agg cca    892
Val Asp Gly Arg Thr Pro Leu Val Leu Ala Thr Gln Met Cys Arg Pro
            155                 160                 165 aca ata tgt caa ctg ctg ata gat aga ggg gcg gat att aat tcc aga    940
Thr Ile Cys Gln Leu Leu Ile Asp Arg Gly Ala Asp Ile Asn Ser Arg
            170                 175                 180 gac aaa caa aac agg act gct ctc atg cta gga tgc gag tat ggt tgc    988
Asp Lys Gln Asn Arg Thr Ala Leu Met Leu Gly Cys Glu Tyr Gly Cys
            185                 190                 195 aaa gat gca gta gaa gtc tta atc aaa aac ggc gct gac gtg acc ttg    1036
Lys Asp Ala Val Glu Val Leu Ile Lys Asn Gly Ala Asp Val Thr Leu
200                 205                 210                 215 ctg gac gcc ctt ggc cat gac agt tct tac tat gca aga att ggt gac    1084
Leu Asp Ala Leu Gly His Asp Ser Ser Tyr Tyr Ala Arg Ile Gly Asp
            220                 225                 230 aat ctg gac att cta acc tta ctg aag act gca tca gaa aat tcc aac    1132
Asn Leu Asp Ile Leu Thr Leu Leu Lys Thr Ala Ser Glu Asn Ser Asn
            235                 240                 245 aaa ggg aga gaa ctt tgg aag aaa gga cca tct tta caa cag cga aat    1180
Lys Gly Arg Glu Leu Trp Lys Lys Gly Pro Ser Leu Gln Gln Arg Asn
            250                 255                 260 ttg tct cag atg cta gat gaa gta aat acg aag tca aat cag agg gag    1228
Leu Ser Gln Met Leu Asp Glu Val Asn Thr Lys Ser Asn Gln Arg Glu
            265                 270                 275 cat caa aac att cag gat ctg gag att gaa aat gaa gat ctg aaa gag    1276
His Gln Asn Ile Gln Asp Leu Glu Ile Glu Asn Glu Asp Leu Lys Glu
280                 285                 290                 295 aga ttg aga aaa att cag caa gaa cag aga ata tta ttg gat aaa gtc    1324
Arg Leu Arg Lys Ile Gln Gln Glu Gln Arg Ile Leu Leu Asp Lys Val
            300                 305                 310 aat ggt tta cag cta cag ctg aat gag gaa gta atg gtg gct gat gat    1372
Asn Gly Leu Gln Leu Gln Leu Asn Glu Glu Val Met Val Ala Asp Asp
            315                 320                 325 ctg gaa agt gag aaa gaa aag ctg aag tcc ctt ttg gca gcc aaa gaa    1420
Leu Glu Ser Glu Lys Glu Lys Leu Lys Ser Leu Leu Ala Ala Lys Glu
            330                 335                 340 aag cag cat gaa gaa agc cta aga act att gag gct ctg aaa agt aga    1468
Lys Gln His Glu Glu Ser Leu Arg Thr Ile Glu Ala Leu Lys Ser Arg
345                 350                 355
```

Fig. 4-2

```
ttt aag tat ttt gag agt gat cat tta gga tca gga agt cat ttc agg    1516
Phe Lys Tyr Phe Glu Ser Asp His Leu Gly Ser Gly Ser His Phe Arg
360             365                 370                 375 aaa gaa gat atg ctt ctt aaa caa ggt caa atg tac atg aca gac tca    1564
Lys Glu Asp Met Leu Leu Lys Gln Gly Gln Met Tyr Met Thr Asp Ser
            380                 385                 390 cag tgt act tcc aca ggc atg cca gtc cat atg caa agc cga tct atg    1612
Gln Cys Thr Ser Thr Gly Met Pro Val His Met Gln Ser Arg Ser Met
                395                 400                 405 tta aga cca ctg gag cta gcc tta cct aat caa gcc tca tat tcg gaa    1660
Leu Arg Pro Leu Glu Leu Ala Leu Pro Asn Gln Ala Ser Tyr Ser Glu
            410                 415                 420 aac gaa att tta aag aaa gaa tta gaa gca atg aga act ttc tgt gat    1708
Asn Glu Ile Leu Lys Lys Glu Leu Glu Ala Met Arg Thr Phe Cys Asp
425                 430                 435 tca gca aaa caa gac aga ctc aaa ctc caa aat gaa ctg gct cac aag    1756
Ser Ala Lys Gln Asp Arg Leu Lys Leu Gln Asn Glu Leu Ala His Lys
440                 445                 450                 455 gtg gcg gag tgc aag gcc tta gca ttg gaa tgt gaa agg gtg aaa gag    1804
Val Ala Glu Cys Lys Ala Leu Ala Leu Glu Cys Glu Arg Val Lys Glu
                460                 465                 470 gat tca gat gag cag ata aag caa cta gaa gat gcc ttg aaa gac gtg    1852
Asp Ser Asp Glu Gln Ile Lys Gln Leu Glu Asp Ala Leu Lys Asp Val
            475                 480                 485 cag aag aga atg tat gag tcg gaa ggt aaa gtg aaa caa atg cag aca    1900
Gln Lys Arg Met Tyr Glu Ser Glu Gly Lys Val Lys Gln Met Gln Thr
        490                 495                 500 cat ttt ctt gcc ttg aaa gag cac ctg aca agt gat gcg gcc act ggg    1948
His Phe Leu Ala Leu Lys Glu His Leu Thr Ser Asp Ala Ala Thr Gly
505                 510                 515 aac cac agg ctg atg gag gaa ctg aag gat cag ttg aaa gac atg aaa    1996
Asn His Arg Leu Met Glu Glu Leu Lys Asp Gln Leu Lys Asp Met Lys
520                 525                 530                 535 gtg aaa tac gaa ggt gcg tcc gca gaa gtg ggg aaa ttg aga aac caa    2044
Val Lys Tyr Glu Gly Ala Ser Ala Glu Val Gly Lys Leu Arg Asn Gln
                540                 545                 550 atc aaa caa aat gaa atg tta gtt gaa gag ttt aag aga gat gag ggc    2092
Ile Lys Gln Asn Glu Met Leu Val Glu Glu Phe Lys Arg Asp Glu Gly
            555                 560                 565
```

Fig. 4-3

```
aag ctg atg gaa gag aat aag cga ctg cag aag gag ttg agc atg tgt    2140
Lys Leu Met Glu Glu Asn Lys Arg Leu Gln Lys Glu Leu Ser Met Cys
        570                 575                 580 gaa ctg gag cga gag aag aga gga agg aag ctc act gag atg gaa ggc    2188
Glu Leu Glu Arg Glu Lys Arg Gly Arg Lys Leu Thr Glu Met Glu Gly
        585                 590                 595 cag tta aag gac ttg tca gcc aag ctg gcc ctt tct att cca gca gag    2236
Gln Leu Lys Asp Leu Ser Ala Lys Leu Ala Leu Ser Ile Pro Ala Glu
600                 605                 610                 615 aaa ttt gaa aac atg aag agc ttg tta tca aat gaa ctg aac gag aag    2284
Lys Phe Glu Asn Met Lys Ser Leu Leu Ser Asn Glu Leu Asn Glu Lys
                620                 625                 630 gca aaa aaa tta ata gat gtg gaa aga gaa tat gaa aga tca ctt aat    2332
Ala Lys Lys Leu Ile Asp Val Glu Arg Glu Tyr Glu Arg Ser Leu Asn
            635                 640                 645 gaa act aga cca tta aag aga gaa ctt gag aat ttg aag gcc aaa ctg    2380
Glu Thr Arg Pro Leu Lys Arg Glu Leu Glu Asn Leu Lys Ala Lys Leu
        650                 655                 660 gct cag cac gtc aaa cca gag gaa cat gag cag ctc aag agc aga tta    2428
Ala Gln His Val Lys Pro Glu Glu His Glu Gln Leu Lys Ser Arg Leu
665                 670                 675 gag cag aag tca gga gaa ctt ggg aag agg atc act gag tta aca tcg    2476
Glu Gln Lys Ser Gly Glu Leu Gly Lys Arg Ile Thr Glu Leu Thr Ser
680                 685                 690                 695 aaa aat cag acg tta caa aag gaa atc gaa aag gtc tgc ctg gat aat    2524
Lys Asn Gln Thr Leu Gln Lys Glu Ile Glu Lys Val Cys Leu Asp Asn
                700                 705                 710 aag ctc ctt aca caa caa gta aat aac tta aca act gaa atg aaa aat    2572
Lys Leu Leu Thr Gln Gln Val Asn Asn Leu Thr Thr Glu Met Lys Asn
            715                 720                 725 cat tac gtc cct tta aaa gta agt gaa gaa atg aaa aag tca cat gat    2620
His Tyr Val Pro Leu Lys Val Ser Glu Glu Met Lys Lys Ser His Asp
        730                 735                 740 gta att gtt gat gat ttg aat aaa aag ctt tca gat gtg aca cac aaa    2668
Val Ile Val Asp Asp Leu Asn Lys Lys Leu Ser Asp Val Thr His Lys
745                 750                 755 tat aca gaa aag aag ttg gaa atg gag aag ttg ctt atg gaa aat gcc    2716
Tyr Thr Glu Lys Lys Leu Glu Met Glu Lys Leu Leu Met Glu Asn Ala
760                 765                 770                 775
```

Fig. 4-4

```
agt tta agt aaa aat gtc agc cgc ctg gaa act gtg ttc ata cct ccc    2764
Ser Leu Ser Lys Asn Val Ser Arg Leu Glu Thr Val Phe Ile Pro Pro
            780                 785                 790 gag aga cac gaa aaa gaa atg atg gct ctg aaa tcc aat atc act gaa    2812
Glu Arg His Glu Lys Glu Met Met Ala Leu Lys Ser Asn Ile Thr Glu
            795                 800                 805 ctt aag aag cag ctg tct gaa ctt aat aaa aaa tgt ggt gaa gac caa    2860
Leu Lys Lys Gln Leu Ser Glu Leu Asn Lys Lys Cys Gly Glu Asp Gln
            810                 815                 820 gag aaa ata tat tca ctc atg tct gaa aac aat gat ttg aaa aag acc    2908
Glu Lys Ile Tyr Ser Leu Met Ser Glu Asn Asn Asp Leu Lys Lys Thr
            825                 830                 835 atg agt cat cag tat gtg ccc gtg aaa acc cat gaa gag att aaa act    2956
Met Ser His Gln Tyr Val Pro Val Lys Thr His Glu Glu Ile Lys Thr
840                 845                 850                 855 gcc ttg agt agc aca ttg gat aaa acc aat aga gaa tta gta gat gtg    3004
Ala Leu Ser Ser Thr Leu Asp Lys Thr Asn Arg Glu Leu Val Asp Val
                860                 865                 870 aag aag aag tgt gaa gat ata aat caa gaa ttt gtg aaa ata aaa gat    3052
Lys Lys Lys Cys Glu Asp Ile Asn Gln Glu Phe Val Lys Ile Lys Asp
                875                 880                 885 gag aac gaa ata tta aaa aga aat ctg gag aac act cag aac caa gta    3100
Glu Asn Glu Ile Leu Lys Arg Asn Leu Glu Asn Thr Gln Asn Gln Val
            890                 895                 900 aaa gct gag tac atc agc cta aga gag cat gaa gaa aag atg agt ggc    3148
Lys Ala Glu Tyr Ile Ser Leu Arg Glu His Glu Glu Lys Met Ser Gly
905                 910                 915 cta agg aag agc atg aag aag gtc cag gac aac agc gct gaa ata ctg    3196
Leu Arg Lys Ser Met Lys Lys Val Gln Asp Asn Ser Ala Glu Ile Leu
920                 925                 930                 935 gct aag tac aaa aaa agc cag gag gag att gtc acc ctg cat gag gag    3244
Ala Lys Tyr Lys Lys Ser Gln Glu Glu Ile Val Thr Leu His Glu Glu
            940                 945                 950 att gca gcc cag aag aga gaa ctc gac acg ata cag gaa tgc atc aag    3292
Ile Ala Ala Gln Lys Arg Glu Leu Asp Thr Ile Gln Glu Cys Ile Lys
            955                 960                 965 cta aaa tat gct ccg atc atc agc ttg gaa gag tgt gag aga aaa ttt    3340
Leu Lys Tyr Ala Pro Ile Ile Ser Leu Glu Glu Cys Glu Arg Lys Phe
            970                 975                 980
```

Fig. 4-5

```
aaa gcc act gag aaa gaa cta aaa gaa cag cta tcc cag cag aca cag    3388
Lys Ala Thr Glu Lys Glu Leu Lys Glu Gln Leu Ser Gln Gln Thr Gln
985                 990                 995 aag tat aat acc agt gaa gaa gag gcc aag aag tgc aag caa gag aat    3436
Lys Tyr Asn Thr Ser Glu Glu Glu Ala Lys Lys Cys Lys Gln Glu Asn
1000                1005                1010                1015 gac aag tta aag aag gag atc ctc act ctt cag aag gat cta aag gat    3484
Asp Lys Leu Lys Lys Glu Ile Leu Thr Leu Gln Lys Asp Leu Lys Asp
                1020                1025                1030 aag aat gtt cac att gag aat tct tat gaa aca gaa aga gca tta agc    3532
Lys Asn Val His Ile Glu Asn Ser Tyr Glu Thr Glu Arg Ala Leu Ser
        1035                1040                1045 aga aaa aca gaa gag ctg aac aga cag tta aaa gac ctg ttg cag aaa    3580
Arg Lys Thr Glu Glu Leu Asn Arg Gln Leu Lys Asp Leu Leu Gln Lys
    1050                1055                1060 tac aca gag gca aag aag gag aaa gag aag ctc gtg gag gaa aat gcc    3628
Tyr Thr Glu Ala Lys Lys Glu Lys Glu Lys Leu Val Glu Glu Asn Ala
1065                1070                1075 aag cag act tct gag atc ctt gca gca caa act ctt ttg cag aag cag    3676
Lys Gln Thr Ser Glu Ile Leu Ala Ala Gln Thr Leu Leu Gln Lys Gln
1080                1085                1090                1095 cat gtt ccg ctg gag cag gtt gag tcc ctg aaa aaa tct ctt agt ggt    3724
His Val Pro Leu Glu Gln Val Glu Ser Leu Lys Lys Ser Leu Ser Gly
            1100                1105                1110 aca atc gag aca ctc aag gaa gaa ctg aaa act aag cag aga tgt tat    3772
Thr Ile Glu Thr Leu Lys Glu Glu Leu Lys Thr Lys Gln Arg Cys Tyr
        1115                1120                1125 gag aaa gag cag cag aca gtg acc caa ctg cgg cag atg ctg gag aat    3820
Glu Lys Glu Gln Gln Thr Val Thr Gln Leu Arg Gln Met Leu Glu Asn
    1130                1135                1140 cag aag aac tcc tct gtg ccc ctg gct gag cat ttg cag gtt aag gaa    3868
Gln Lys Asn Ser Ser Val Pro Leu Ala Glu His Leu Gln Val Lys Glu
1145                1150                1155 gca ttt gag aaa gaa gtt gga atc ata aaa gct agc ttg aga gaa aag    3916
Ala Phe Glu Lys Glu Val Gly Ile Ile Lys Ala Ser Leu Arg Glu Lys
1160                1165                1170                1175 gaa gaa gaa agc caa aac aaa act gaa gag gtc tcc aaa ctc cag tct    3964
Glu Glu Glu Ser Gln Asn Lys Thr Glu Glu Val Ser Lys Leu Gln Ser
            1180                1185                1190
```

Fig. 4-6

```
gag att cag aat act aaa caa gcg tta aaa aaa tta gag act cgg gag    4012
Glu Ile Gln Asn Thr Lys Gln Ala Leu Lys Lys Leu Glu Thr Arg Glu
        1195                1200                1205 gtg gtt gat ttg tcg aaa tat aaa gca acg aaa agc gat ttg gag aca    4060
Val Val Asp Leu Ser Lys Tyr Lys Ala Thr Lys Ser Asp Leu Glu Thr
        1210                1215                1220 cag att tcc gac tta aac gaa aaa ttg gcc aat ctg aat agg aag tat    4108
Gln Ile Ser Asp Leu Asn Glu Lys Leu Ala Asn Leu Asn Arg Lys Tyr
        1225                1230                1235 gag gaa gta tgt gag gag gtt ttg cat gcc aaa aag aag gaa ctg tct    4156
Glu Glu Val Cys Glu Glu Val Leu His Ala Lys Lys Lys Glu Leu Ser
1240                1245                1250                1255 gct aaa gat gag aag gaa ttg ctc cat ttc agc ata gag caa gaa atc    4204
Ala Lys Asp Glu Lys Glu Leu Leu His Phe Ser Ile Glu Gln Glu Ile
            1260                1265                1270 aaa gat cag cag gaa cga tgt gac aaa tcc tta aca acc atc acg gag    4252
Lys Asp Gln Gln Glu Arg Cys Asp Lys Ser Leu Thr Thr Ile Thr Glu
        1275                1280                1285 cta cag aga aga ata cag gaa tct gcc aaa caa atc gaa gca aaa gat    4300
Leu Gln Arg Arg Ile Gln Glu Ser Ala Lys Gln Ile Glu Ala Lys Asp
        1290                1295                1300 aat aag ata act gaa ctg ctc aat gat gtg gag aga tta aaa cag gcc    4348
Asn Lys Ile Thr Glu Leu Leu Asn Asp Val Glu Arg Leu Lys Gln Ala
    1305                1310                1315 ctc aat ggc ctt tcc cag ctc acc tat gga agt ggg agt ccc agc aag    4396
Leu Asn Gly Leu Ser Gln Leu Thr Tyr Gly Ser Gly Ser Pro Ser Lys
1320                1325                1330                1335 agg cag agt cag ctg att gac agc ctg cag cag cag gtc agg tcc ctg    4444
Arg Gln Ser Gln Leu Ile Asp Ser Leu Gln Gln Gln Val Arg Ser Leu
                1340                1345                1350 cag cag cag ctg gcg gat gcc gac aga cag cac caa gaa gta att gca    4492
Gln Gln Gln Leu Ala Asp Ala Asp Arg Gln His Gln Glu Val Ile Ala
            1355                1360                1365 att tat cgg aca cac ctt ctt agt gct gca cag ggt cac atg gat gag    4540
Ile Tyr Arg Thr His Leu Leu Ser Ala Ala Gln Gly His Met Asp Glu
        1370                1375                1380 gat gtg cag gcc gcc tta ctg cag atc ata cag atg cgg cag ggg ctc    4588
Asp Val Gln Ala Ala Leu Leu Gln Ile Ile Gln Met Arg Gln Gly Leu
        1385                1390                1395
```

Fig. 4-7

```
gtg tgc tagtcggcac cccccagccc acagtggctt tccctgctgg tgctgagcat    4644
Val Cys
1400 tctgtgcgca acttcatggc ctttctgggc ctcgctgtgc tagtataatt aaaataaagt 4704 gtattttgat ccatcaaaaa aaaaaaaaaa aa                               4736
```

Fig. 4-8

Sequence Alignment of bcap73 cDNA against Canine familiaris mRNA for C3VS protein (GenBank accession X99145)

```
Query=βCAP73
Sbjct=C3VS

Query:  358  tttgctgttagcaacaagaaactaaatcctgtctatgatgagctgttggttttcttgtgc 417
             ||||||| |||||||| ||||| ||||||||||||||||| ||||||||||||||||||
Sbjct:   12  tttgctgctagcaaccagaaaccaaatcctgtctatgatgaactgttggttttcttgtgc 71

Query:  418  tcctaagaacagacaagcagcagattggaacaaatacgatgaccgattgatgagagcagc 477
             || ||||||||||| |||||||||||||||||||| ||||||||||||||||| | |||
Sbjct:   72  tcccaagaacagacatgcagcagattggaacaaatatgatgaccgattgatgaaagccgc 131

Query:  478  agaaaggggagatgtagaaaaagtgtcctcaatccttgctaaaaagggagtcaatccagg 537
              | ||||||||||||||||||||| ||||||||||||||||||||||| |||||||||
Sbjct:  132  ggagaggggagatgtagaaaaagtttcctcaatccttgctaaaaagggcatcaatccagg 191

Query:  538  caagctagatgtagaaggcagatctgcctttcatgttgtggcctcaaagggaaatcttga 597
             ||| ||||||gt ||aaggcagatctgcctt catgttgtggcctcaaaggg aatcttga 597
Sbjct:  192  caaactagatgtggaaggcagatctgccttccatgttgtggcctcaaaggggaatcttga 251

Query:  598  gtgtttgaatgccatcctcatacatggagttgatattacaaccagtgacaccgcaggaag 657
              |||||||||||||||| |||||||||||||||||||||||||||||||| ||||||||
Sbjct:  252  atgtttgaatgccatccttatacatggagttgatattacaaccagtgacactgcaggaag 311

Query:  658  gaatgctcttcacctggctgcaaagtatgggcatgcactgtgtctacaaaaacttctaca 717
             ||||||||||||| |||||||||||||||||||||||| ||||||||||||||||||||
Sbjct:  312  aaatgctcttcacttggctgcaaagtatgggcatgcattgtgtctacaaaaacttctaca 371

Query:  718  gtacaattgtcccactgaacatgtagacctgcagggaagaactgcacttcatgatgcagc 777
             ||||||||||||||||||||||| |||||||||||||||| |||||||||||| |||||
Sbjct:  372  gtacaattgtcccactgaacatgcagacctgcagggaagaaccgcacttcatgacgcagc 431

Query:  778  tatggcagactgtccttctagcatacagctgctctgcgaccatggggcctcggtgaatgc 837
             | ||||||||||||||| ||||||||||||||| || |||||||||||||| |||||||
Sbjct:  432  aatggcagactgtccttccagcatacagctgctttgtgaccatggggcctccgtgaatgc 491

Query:  838  caaagatgtagatgggcggacaccacttgttctggctacccagatgtgtaggccaacaat 897
             |||||||| |||||||||||||| | ||||||||||||| ||||||||||||||| |||
Sbjct:  492  caaagatgtggatgggcggacaccgctggttctggctactcagatgtgtaggccagcaat 551
```

Fig. 9-1

```
Query:  898  atgtcaactgctgatagatagaggggcggatattaattccagagacaaacaaaacaggac  957
             |||||||||||||||||| ||||||| ||||||||||||||||||||||||||||||
Sbjct:  552  ctgtcaactgctgatagatcgaggggcagagattaattccagagacaaacaaaacagaac  611

Query:  958  tgctctcatgctaggatgcgagtatggttgcaaagatgcagtagaagtcttaatcaaaaa  1017
             |||||||||||| |||| |||||||||||||| | |||| |||||||||||| |||||
Sbjct:  612  tgctctcatgcttggttgcgagtatggttgtaaggatgctgtagaagtcttacttaaaaa  671

Query:  1018 cggcgctgacgtgaccttgctggacgcccttggccatgacagttcttactatgcaagaat  1077
             || |||| | |||| ||||||||  |||||||||||| |||||||||||||||||||||
Sbjct:  672  tggtgctgatgtaagcctgctggatgccttgggccatgatagttcttactatgcaagaat  731

Query:  1078 tggtgacaatctggacattctaaccttactgaagactgcatcagaaaattccaacaaagg  1137
             |||||||||||||||||||||||| |||| ||||||||| |||||||| ||||||||||
Sbjct:  732  tggtgacaatctggacattctaactttattgaagactgcgtcagaaaataccaacaaagg  791

Query:  1138 gagagaactttggaagaaaggaccatctttacaacagcgaaatttgtctcagatgctaga  1197
             |||||||||||||||||||||||||||||||| ||||||||||||| | |||||||||
Sbjct:  792  gagagaactttggaagaaaggaccatctttacagcagcgaaatttgccgtacatgctaga  851

Query:  1198 tgaagtaaatacgaagtcaaatcagagggagcatcaaaacattcaggatctggagattga  1257
             ||||||||| | |||||||| |||||||||||||| |||||||||||| |||||||||
Sbjct:  852  tgaagtaaatgtgaagtcaagtcagagggagcatcgaaacattcaggagctggagattga  911

Query:  1258 aaatgaagatctgaaagagagattgagaaaaattcagcaagaacagagaatattattgga  1317
             |||||||| | ||||||||  || ||||||||||||||||||||||||||||||| |||
Sbjct:  912  aaatgaagatttgaaagacaggttgagaaaaattcagcaagaacagagaatattactgga  971

Query:  1318 taaagtcaatggtttacagctacagctgaatgaggaagtaatggtggctgatgatctgga  1377
             ||||||||||||||||||| ||||||||||||||||||| |||| ||||||||||||||
Sbjct:  972  taaagtcaatggtttacaactacagctgaatgaggaagtgatggttgctgatgatctgga  1031

Query:  1378 aagtgagaaagaaaagctgaagtcccttttggcagccaaagaaaagcagcatgaagaaag  1437
             ||||||||||||||||||||||| || |||||| ||||||||||||| |||||||||||
Sbjct:  1032 aagtgagaaagaaaagctgaagtctcttttggtggctaaagaaaagcaacatgaagaaag  1091

Query:  1438 cctaagaactattgaggctctgaaaagtagatttaagtattttgag  1483
             ||||||||||||||| | |||||||| |||||||| |||||||||
Sbjct:  1092 cctaagaactattgagtctctgaaaaacagatttaaatattttgag  1137
```

Fig. 9-2

```
Query: 1566 agtgtacttccacaggcatgccagtccatatgcaaagccgatctatgttaagaccactgg 1625
             ||||||||||| ||| ||||| ||| |||||||| |||||||||||||||||||||||
Sbjct: 1136 agtgtacttccccaggggtgccagcccacatgcaaagcaggtctatgttaagaccactgg 1195

Query: 1626 agctagccttacctaatcaagcctcatattcggaaaacgaaatttttaaagaaagaattag 1685
             ||||| |||||| |||||| ||||||||| ||||| || ||||| ||||||||||  ||
Sbjct: 1196 agctatcattacccaatcaaacctcatattctgaaaatgacctcttaaagaaagagttag 1255

Query: 1686 aagcaatgagaactttctgtgattcagcaaaacaagacagactcaaactccaaaatgaac 1745
             |||||||||||||||||| |||||||| ||||||||||| |||||| |||| |||||
Sbjct: 1256 aagcaatgagaactttctgcgaatcagccaaacaagaccgcctcaagctccagaacggag 1315

Query: 1746 tggctcacaaggtggcggagtgcaaggccttagcattggaatgtgaaagggtgaaagagg 1805
             |||| |||||||||| ||||||| || ||||| || ||||||||| | |||| ||||
Sbjct: 1316 tggcgcacaaggtggctgagtgcaaagctttaggactagaatgtgaacgcatcaaggagg 1375

Query: 1806 attcagatgagcagataaagcaactagaagatgccttgaaagacgtgcagaagagaatgt 1865
              || ||||||||||||||||||  |||||| ||| | ||||| ||||||||||||||
Sbjct: 1376 actctgatgagcagataaagcagttagaagacgcattgaaagatgtgcagaagagaatgt 1435

Query: 1866 atgagtcggaaggtaaagtgaaacaaatgcagacacatttcttgccttgaaagagcacc 1925
             |||||||||||||||||| |||||||||||||||||| |||||||| | |||||||||
Sbjct: 1436 atgagtcggaaggtaaagtaaaacaaatgcagacacactttcttgcccttaaagagcacc 1495

Query: 1926 tgacaagtgatgcggccactgggaaccacaggctgatggaggaactgaaggatcagttga 1985
             |||| ||||| |||| |  |||| ||||||| |||||||| |||||||||||||||||
Sbjct: 1496 tgaccagtgaagcagctataggggaatcacagactaatggaggagctgaaggatcagttga 1555

Query: 1986 aagacatgaaagtgaaatacgaaggtgcgtccgcagaagtggggaaattgagaaaccaaa 2045
              |||||||||| |||||| ||||| || || ||||||||||| ||| || |||||||
Sbjct: 1556 aggacatgaaagcgaaatatgagggtgcatcagcagaagtgggaaaactgcgaaaccaaa 1615

Query: 2046 tcaaacaaaatgaaatgttagttgaagagtttaagagagatgagggcaagctgatggaag 2105
             ||||||||||||  || |||| ||||| |||||||||||||| ||||||||| |||||
Sbjct: 1616 tcaaacaaaatgagctgctagtagaacagtttaggagagatgaaggcaagctggtggaag 1675

Query: 2106 agaataagcgactgcagaaggagttgagcatgtgtgaactggagcgagagaagagaggaa 2165
             |||||||||||| ||||||| | ||||| |||||||| ||||||||||| |||| |||
Sbjct: 1676 agaataagcgattgcagaaggaactcagtatgtgtgaaacggagcgagacaagaaaggaa 1735
```

Fig. 9-3

```
Query: 2166  ggaagctcactgagatggaaggccagttaaaggacttgtcagccaagctggccctttcta  2225
             ||| | |  ||||||  ||||||||| ||||||||  ||||||  | ||| ||||||  || | ||
Sbjct: 1736  ggagggttgctgaggtggaaggccaggtaaaggaactcttagcaaagctgaccttgtcag  1795

Query: 2226  ttccagcagagaaatttgaaaacatgaagagcttgttatcaa  2267
             |||||| || |||||||| | |||||||||||| |||||||
Sbjct: 1796  ttccaactgaaaaatttgagagcatgaagagcttattatcaa  1837
```

Fig. 9-4

Sequence Alignment of bcap73 against Tentative Human Concensus (THC) Contiguous Sequences THC244788 THC143090 THC186491 THC213238 (from TIGR)

Score = 1052 bits (547), Expect = 0.0
Identities = 905/1092 (82%), Positives = 905/1092 (82%), Gaps = 4/1092 (0%)

Query=bcap73 cDNA
Sbjct=THC seq

```
Query: 3136 aaagatgagtggcctaaggaagagcatgaagaaggtccaggacaacagcgctgaaatact 3195
            |||||||| |||||  ||||||||| || |||||| ||||  |  || |||||||   |
Sbjct: 6    aaagatgagctcgctaagtcagagcatgagaaaggtscaggatagtaatgctgaaatctt 65

Query: 3196 ggctaagtacnnnnnnnngccaggaggagattgtcaccctgcatgaggagattgcagccca 3255
            ||| | |||           |||||||||||||| || ||||| |||| ||| ||||||
Sbjct: 66   ggccamctacagaaaaggccaagaagagattgtgacactkcatgccgaaattaragccca 125

Query: 3256 gaagagagaactcgacacgatacaggaatgcatcaagctaaaatatgctccgatcatcag 3315
            || || || ||||||||| |||||| ||||||||| || |||||||||||  ||||| ||||
Sbjct: 126  gargarggagctcgacacaatacaagartgcattaaggtaaaatatgccccaattgtcag 185

Query: 3316 cttggaagagtgtgagagaaaatttaaagccactgagaagaac-taaaagaacagctat 3374
            ||| | |||| | ||||||||||||||||| ||||| |||||| |||||| ||| |||
Sbjct: 186  ctttgaggagtscgagagaaaatttaaagcaacagagaaagaacctaaaagaccagttat 245

Query: 3375 cccagcagacacagaagtataataccagtgaagaagaggccaagaagtgcaagcaagaga 3434
              |||||||||||| ||||| |  || ||||||||||||  ||||| | |||||||||||
Sbjct: 246  cagagcagacacaaaagtatagtgtcagtgaagaagaagtcaagaaaaacaagcaagaga 305

Query: 3435 atgacaagttaaagaaggagatcctcactcttcagaaggatctaaaggataagaatgttc 3494
            |||||||||||||||||||||| |  || ||||||||||| || | || ||| ||||||
Sbjct: 306  atgacaagttaaagaaggagattttacccttcagaaagatttgagagayaagacagttc 365

Query: 3495 acattgagaattcttatgaaacagaaagagcattaagcagaaaaacagaagagctgaaca 3554
            ||||||| ||| |||||||  |||||||||||||||||||||||||||| ||||| ||||
Sbjct: 366  tcattgagaagtctcatgaaatggaaagagcattaagcagaaaaacagacgagctaaaca 425

Query: 3555 gacagttaaaagacctgttgcagaaatacacagaggcaaagaaggagaaagagaagctcg 3614
            | |||||||||| ||| | ||||||||||||| ||| ||| ||| | |||||||||| |
Sbjct: 426  aacagttaaaagacttgtcacagaaatacacggaagtaaagaatgtgaaagagaagctag 485
```

Fig. 10-1

```
Query: 3615 tggaggaaaatgccaagcagacttctgagatccttgcagcacaaactcttttgcagaagc 3674
              ||||||||||||||||  ||||||||||||||||||  ||||| |||| ||||||||| |
Sbjct: 486  tagaagaaaatgccaaacagacttctgagatacttgcagtgcaaaatcttttgcaaaaac 545

Query: 3675 agcatgttccgctggagcaggttgagtccctgaaaaaatctcttagtggtacaatcgaga 3734
             |||||||||  ||||  ||||||||| | ||||||||||||||||| |||  ||||  |
Sbjct: 546  aacatgttccattggaacaggttgaggctctgaaaaaatctcttaatggcacaattgaaa 605

Query: 3735 cactcaaggaagaactgaaaactaagcagagatgttatgagaaagagcagcagacagtga 3794
            |  ||||||||||||||  ||  ||| |||| || |  ||||||||||||||||||||||
Sbjct: 606  atctaaaggaagaactgaagagtatgcaaaggtgttacgagaaagagcagcagacagtga 665

Query: 3795 cccaactgcggcagatgctggagaatcagaagaactcctctgtgcccctggctgagcatt 3854
            || ||||||| || |  || |||||||| |||||||| |||||| ||||||| |||||||
Sbjct: 666  ccaaactgcatcaattgttggagaatcaaaagaactcttctgtaccc ctggcagagcatt 725

Query: 3855 tgcaggttaaggaagcatttgagaaagaagttggaatcataaaagctagcttgagagaaa 3914
            ||||| || ||||||||||||||||||||||||||||||||||||| ||||||||||||
Sbjct: 726  tgcagattaaagaagcatttgagaaagaagttggaatcataaaagccagcttgagagaaa 785

Query: 3915 aggaagaagaaagccaaaacaaaactgaagaggtctccaaactccagtctgagattcaga 3974
            ||||||||||||||||||||||||  |||||||||||||||| |||| || |||||||
Sbjct: 786  aggaagaagaaagccaaaacaaaatggaagaagtctccaaacttcagtcggaggttcaga 845

Query: 3975 atactaaacaagcgttnnnnnnnnttagagactcgggaggtggttgatttgtcgaaatata 4034
            |||||||||||||| ||        ||||||||  ||||||| ||| |||||  ||||||
Sbjct: 846  atactaaacaagcmttaaaaaaattagagactagagaggtagttgacttgtctaaatata 905

Query: 4035 aagcaacgaaaagcgatttggagacacagatttccgacttaaacgaaaaattggccaatc 4094
            |||||||  ||||| ||||||||||||||||||| |||||||| ||||||||||||||||
Sbjct: 906  aagcaacaaaaagtgatttggagacacagatttctagcttaaatgaaaaattggccaatc 965

Query: 4095 tgaataggaagtatgaggaagtatgtgaggaggttttgcatgccaaaaagaaggaactgt 4154
            |||||||| ||||||||||||| |||||||||| ||||||||||  ||||||||| |||
Sbjct: 966  tgaatagaaagtatgaggaagt-tgtgaggaagttttgcatgccmaaaagaaggaaatat 1024

Query: 4155 ctgctaaagatgagaaggaattgctccatttcagcatagagcaagaaatcaaagatcagc 4214
            ||| ||||||||||||||| ||||| |||||||| ||  |||||| ||||||| || ||||
Sbjct: 1025 ctgscaaagatgagaagga-ttactgc-tttcaccttgagscaggaaattaagggtcagr 1082
```

Fig. 10-2

```
Query: 4215 aggaacgatgtg 4226
             ||||||||||||
Sbjct: 1083 aggaacgatgtg 1094
```

Fig. 10-3

β-CAP73 CONTROL OF NORMAL AND ABNORMAL CELL MIGRATION

RELATED APPLICATIONS

This application claims priority to U.S. Provisional Application No. 60/170,182, filed on Dec. 10, 1999, and is a continuation in part of U.S. Utility application Ser. No. 09/733,818, filed on Dec. 8, 2000, now abandoned, the contents of each are incorporated herein in their entirety by this reference.

GOVERNMENT SUPPORT

This invention was made with government support under GM55110 awarded by the National Institutes of Health. The government has certain rights in the invention.

BACKGROUND OF THE INVENTION

Many eukaryotic cells necessarily possess the ability to move within their environment in response to certain stimuli (e.g. endothelial cells in response to injury, macrophages during immune response). This property of motility is facilitated by coordinated and dynamic modifications to the structure of the cytoskeleton, resulting in net movement. A major cytoskeletal component of motile eukaryotic cells are actin complexes, whose filamentous structure throughout the cell is complex and highly variable. Numerous isoforms of eukaryotic actin have been identified, many of which are found distributed to specific areas of the cell and its cytoskeleton. The ability to disassemble and reassemble actin polymers in a controlled and orderly fashion is central to proper cellular motility. Polymerized actin exists in equilibrium with the monomeric form. The equilibrium constant for the polymerization and depolymerization reactions of actin can be altered by the presence of actin-binding proteins (ABPs). These proteins play an important role in a cell's ability to control cytoskeletal rearrangements, and hence, promote effective cell motility. Many vital functions are served through the ability of some cells to migrate, including response and repair or tissue damage.

SUMMARY OF THE INVENTION

The present invention is based, at least in part, on the discovery of a novel β-actin specific binding protein and its family members, referred to herein as "beta-cap73" or "BETA-CAP73" or "βcap73" or "βCAP73" or "BCAP73" or "bcap73" nucleic acid and protein molecules. The bcap73 molecules of the present invention are useful as modulating agents to regulate a variety of cellular processes, including but not limited to cell motility, directed migration, subcellular distribution of β-actin, response to injury, and changes in cellular morphology. Accordingly, in one aspect, this invention provides isolated nucleic acid molecules encoding bcap73 proteins or biologically active portions thereof, as well as nucleic acid fragments suitable as primers or hybridization probes for the detection of bcap73-encoding nucleic acids.

In one embodiment, a bcap73 nucleic acid molecule of the invention is at least 40%, 45%, 50%, 55%, 60%, 65%, 70%, 75%, 80%, 83%, 85%, 90%, 95%, 98%, identical to the nucleotide sequence (e.g., to the entire length of the nucleotide sequence) shown in SEQ ID NO:1 or 3, or a complement thereof.

In a preferred embodiment, the isolated nucleic acid molecule includes the nucleotide sequence shown SEQ ID NO: 1 or 3, or a complement thereof. In another embodiment, the nucleic acid molecule includes SEQ ID NO: 3 and nucleotides 392–4597 of SEQ ID NO: 1. In another preferred embodiment, the nucleic acid molecule consists of the nucleotide sequence shown in SEQ ID NO: 1 or 3. In another preferred embodiment, the nucleic acid molecule includes a fragment of at least 1911 nucleotides (e.g., 1911 contiguous nucleotides) of the nucleotide sequence of SEQ ID NO: 1 or 3, or a complement thereof In another embodiment, a bcap73 nucleic acid molecule includes a nucleotide sequence encoding a protein having an amino acid sequence sufficiently identical to the amino acid sequence of SEQ ID NO: 2. In a preferred embodiment, a bcap73 nucleic acid molecule includes a nucleotide sequence encoding a protein having an amino acid sequence at least 40%, 45%, 50%, 55%, 60%, 65%, 70%, 75%, 80%, 83%, 85%, 90%, 95%, 98% or more identical to the entire length of the amino acid sequence of SEQ ID NO: 2.

In another preferred embodiment, an isolated nucleic acid molecule encodes the amino acid sequence of bovine or human or another vertebrate bcap73. In yet another preferred embodiment, the nucleic acid molecule includes a nucleotide sequence encoding a protein having the amino acid sequence of SEQ ID NO: 2. In yet another preferred embodiment, the nucleic acid molecule is at least 1911 nucleotides in length. In a further preferred embodiment, the nucleic acid molecule is at least 1911 nucleotides in length and encodes a protein having a bcap73 activity (as described herein).

Another embodiment of the invention features nucleic acid molecules, preferably bcap73 nucleic acid molecules, which specifically detect bcap73 nucleic acid molecules relative to nucleic acid molecules encoding non-bcap73 proteins. For example, in one embodiment, such a nucleic acid molecule is at least 1911, 1911–2000, 2000–2250, 2250–2500, 2500–2750, 2750–3000, 3000–3250, 3250–3500, 3500–3750, 3750–4000, 4000–4250, 4250–4500, 4500–4736 or more nucleotides in length and hybridizes under stringent conditions to a nucleic acid molecule comprising the nucleotide sequence shown in SEQ ID NO: 1, or a complement thereof. The lengths of nucleic acid molecules of this invention can be within a range using any one of the aforementioned numbers as the upper or lower limit of the range. For example, the nucleic acid molecules can be of a length between at least 1911 and 3000 nucleotides in length.

In preferred embodiments, the nucleic acid molecules are at least 15 (e.g., contiguous) nucleotides in length and hybridize under stringent conditions to nucleotides 1–357, 2268–3135, 4227–4736, of SEQ ID NO: 1. In other preferred embodiments, the nucleic acid molecules comprise nucleotides 1–357, 2268–3135, 4227–47326, of SEQ ID NO: 1. In other preferred embodiments, the nucleic acid molecules consist of nucleotides 1–357, 2268–3135, 4227–4736, of SEQ ID NO: 1.

In other preferred embodiments, the nucleic acid molecule encodes a naturally occurring allelic variant of a polypeptide comprising the amino acid sequence of SEQ ID NO: 2, wherein the nucleic acid molecule hybridizes to a nucleic acid molecule comprising SEQ ID NO: 1 or 3 under stringent conditions.

Another embodiment of the invention provides an isolated nucleic acid molecule which is antisense to a bcap73 nucleic acid molecule, e.g., the coding strand of a bcap73 nucleic acid molecule.

Another aspect of the invention provides a vector comprising a bcap73 nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a bcap73 protein, by culturing in a suitable medium, a host cell, e.g., a mammalian host cell such as a human or a non-human mammalian cell, of the invention containing a recombinant expression vector, such that the protein is produced.

Another aspect of this invention features isolated or recombinant bcap73 proteins and polypeptides. In one embodiment, the isolated protein, preferably a bcap73 protein, includes at least one ankyrin repeat domain. In another embodiment, the isolated protein, preferably a bcap73 protein, includes an actin binding domain. In another embodiment, the isolated protein, preferably a bcap73 protein, includes an ezrin binding domain. In yet another embodiment, the isolated protein, preferably a bcap73 protein, includes at least one ankyrin repeat domain and an actin binding domain. In a preferred embodiment, the protein, preferably a bcap73 protein, includes at least one ankyrin repeat domain and has an amino acid sequence at least about 40%, 45%, 50%, 55%, 60%, 65%, 70%, 75%, 80%, 85%, 90%, 95%, 98% or more identical to the amino acid sequence of SEQ ID NO: 2. In another preferred embodiment, the protein, preferably a bcap73 protein, includes an actin binding domain and has an amino acid sequence at least about 40%, 45%, 50%, 55%, 60%, 65%, 70%, 75%, 80%, 83%, 85%, 90%, 95%, 98% or more identical to the amino acid sequence of SEQ ID NO: 2. In a further preferred embodiment, the protein, preferably a bcap73 protein, includes at least one actin binding domain and an ankyrin repeat domain and has an amino acid sequence at least about 30%, 35%, 40%, 45%, 50%, 55%, 60%, 65%, 70%, 75%, 80%, 83%, 85%, 90%, 95%, 98% or more identical to the amino acid sequence of SEQ ID NO: 2.

In another preferred embodiment, the protein, preferably a bcap73 protein, includes at least one ankyrin binding domain and plays a role in cytoskeletal structure and cell motility, e.g., the regulation of actin function and/or actin intracellular distribution. In yet another preferred embodiment, the protein, preferably a bcap73 protein, includes an actin binding domain and plays a role in cell motility, e.g., the regulation of actin function and/or the intracellular distribution of actin. In a further preferred embodiment, the protein, preferably a bcap73 protein, includes at least one ankyrin binding domain and one actin binding domain and plays a role in cell motility, e.g., the regulation of actin function and/or the intracellular distribution of actin. In yet another preferred embodiment, the protein, preferably a bcap73 protein, includes at least one ankyrin binding domain and is encoded by a nucleic acid molecule having a nucleotide sequence which hybridizes under stringent hybridization conditions to a nucleic acid molecule comprising the nucleotide sequence of SEQ ID NO: 1 or 3. In a further embodiment, the protein, preferably a bcap73 protein, includes an actin binding domain and is encoded by a nucleic acid molecule having a nucleotide sequence which hybridizes under stringent hybridization conditions to a nucleic acid molecule comprising the nucleotide sequence of SEQ ID NO: 1 or 3. In another embodiment, the protein, preferably a bcap73 protein, includes at least one ankyrin binding domain and at least one an actin binding domain and is encoded by a nucleic acid molecule having a nucleotide sequence which hybridizes under stringent hybridization conditions to a nucleic acid molecule comprising the nucleotide sequence of SEQ ID NO: 1 or 3.

In another embodiment, the invention features fragments of the protein having the amino acid sequence of SEQ ID NO: 2, wherein the fragment comprises at least 15 amino acids (e.g., contiguous amino acids) of the amino acid sequence of SEQ ID NO: 2. In another embodiment, the protein, preferably a bcap73 protein, has the amino acid sequence of SEQ ID NO: 2.

In another embodiment, the invention features an isolated protein, preferably a bcap73 protein, which is encoded by a nucleic acid molecule consisting of a nucleotide sequence at least about 40%, 45%, 50%, 55%, 60%, 65%, 70%, 75%, 80%, 83%, 85%, 90%, 95%, 98% or more identical to a nucleotide sequence of SEQ ID NO: 1 or 3, or a complement thereof. This invention further features an isolated protein, preferably a bcap73 protein, which is encoded by a nucleic acid molecule consisting of a nucleotide sequence which hybridizes under stringent hybridization conditions to a nucleic acid molecule comprising the nucleotide sequence of SEQ ID NO: 1 or 3, or a complement thereof.

The proteins of the present invention or portions thereof, e.g., biologically active portions thereof, can be operatively linked to a non-bcap73 polypeptide (e.g., heterologous amino acid sequences) to form fusion proteins. The invention further features antibodies, such as monoclonal or polyclonal antibodies, that specifically bind proteins of the invention, preferably bcap73 proteins. In addition, the bcap73 proteins or biologically active portions thereof can be incorporated into pharmaceutical compositions, which optionally include pharmaceutically acceptable carriers.

In another aspect, the present invention provides a method for detecting the presence of a bcap73 nucleic acid molecule, protein or polypeptide in a biological sample by contacting the biological sample with an agent capable of detecting a bcap73 nucleic acid molecule, protein or polypeptide such that the presence of a bcap73 nucleic acid molecule, protein or polypeptide is detected in the biological sample.

In another aspect, the present invention provides a method for detecting the presence of bcap73 activity in a biological sample by contacting the biological sample with an agent capable of detecting an indicator of bcap73 activity such that the presence of bcap73 activity is detected in the biological sample.

In another aspect, the invention provides a method for modulating bcap73 activity comprising contacting a cell capable of expressing bcap73 with an agent that modulates bcap73 activity such that bcap73 activity in the cell is modulated. In one embodiment, the agent inhibits bcap73 activity. In another embodiment, the agent stimulates bcap73 activity. In one embodiment, the agent is an antibody that specifically binds to a bcap73 protein. In another embodiment, the agent modulates expression of bcap73 by modulating transcription of a bcap73 gene or translation of a bcap73 mRNA. In yet another embodiment, the agent is a nucleic acid molecule having a nucleotide sequence that is antisense to the coding strand of a bcap73 mRNA or a bcap73 gene.

In one embodiment, the methods of the present invention are used to treat a subject having a disorder characterized by aberrant or unwanted bcap73 protein or nucleic acid expression or activity by administering an agent which is a bcap73 modulator to the subject. In one embodiment, the bcap73 modulator is a bcap73 protein. In another embodiment the bcap73 modulator is a bcap73 nucleic acid molecule. In yet another embodiment, the bcap73 modulator is a peptide, peptidomimetic, or other small molecule. In a preferred embodiment, the disorder characterized by aberrant or unwanted bcap73 protein or nucleic acid expression is a disorder associated with deregulated cell motility or with aberrant intracellular distribution of actin isoforms (e.g. β-actin); or with inability to adequately respond to tissue damage; or with tumor-induced angiogenesis; or with cardiovascular disorders or conditions.

The present invention also provides diagnostic assays for identifying the presence or absence of a genetic alteration characterized by at least one of (i) aberrant modification or mutation of a gene encoding a bcap73 protein; (ii) misregulation of the gene; and (iii) aberrant post-translational modification of a bcap73 protein, wherein a wild-type form of the gene encodes a protein with a bcap73 activity.

In another aspect the invention provides methods for identifying a compound that binds to or modulates the activity of a bcap73 protein, by providing an indicator composition comprising a bcap73 protein having bcap73 activity, contacting the indicator composition with a test compound, and determining the effect of the test compound on bcap73 activity in the indicator composition to identify a compound that modulates the activity of a bcap73 protein.

Other features and advantages of the invention will be apparent from the following detailed description and claims.

BRIEF DESCRIPTION OF THE DRAWINGS

FIGS. 4-1, 4-2, 4-3, 4-4, 4-5, 4-6, 4-7, and 4-8: The cDNA sequence of bcap73 is shown, with the 5' and 3' untranslated regions. The entire nucleotide sequence is SEQ ID NO: 1. The nucleotide sequence which corresponds to the open reading frame (ORF) spans nucleotide positions 392 to 4597 and is SEQ ID NO: 3. The deduced amino acid sequence which is coded in the ORF is shown as well and is SEQ ID NO: 2.

FIG. 5: A northern blot analysis on bcap73 mRNA expression in various tissues. Transcript is detected predominantly in skeletal muscle, brain and heart.

FIG. 6: Immunofluorescence photography showing the formation of novel membrane protrusions in bovine retinal pericytes which overexpress histidine-tagged recombinant bcap73. These rounded protrusions are predominantly located on the ventral regions of the cell. Recombinant bcap73 is found within these membrane protrusions. The left side shows filamentous actin visualized with rhodamine-conjugated phalloidin. The right side shows localization of recombinant bcap73 using INDIA probe (a horseradish peroxidase-conjugated nickel reagent) which identified the histidine tag, followed by rabbit anti-HRP and fluorescein-conjugated anti-rabbit antibodies.

FIG. 7: Immunofluorescence photography showing the formation of aberrant cellular projections in bovine retinal pericytes which overexpress recombinant bcap73 domains fused to GFP (green fluorescent protein). CAP-C-GFP (bcap73 bases 3503–4736) and CAP-N-GFP (bcap73 bases 2430–3503) were transiently transfected into bovine retinal pericytes, causing these cells to project arborized membrane structures. Note that untransfected cells do not exhibit these protrusions, but remain flat. CAP-N-GFP expression is shown on top (A), CAP-C-GFP expression is shown below (B). Left and right sides are matched fluorescent and phase images.

FIG. 8: A northern blot analysis showing that bcap73 transcript is down-regulated in endothelial cells which are responding to injury. Endothelial cells that are mechanically injured migrate into wound spaces in order to repair and re-populate the area. These crawling cells show a large decrease in bcap73 mRNA as an early response to the injury at 30, 60, and 90 minutes after injury. Here, this is compared to contact-inhibited, stationary cells (marked "con").

FIGS. 9-1, 9-2, 9-3, and 9-4: A sequence alignment of bcap73 cDNA (SEQ ID NO:1) against the C: familiaris C3VS gene (GenBank Accession No. X99145).

FIGS. 10-1, 10-2, and 10-3: A sequence alignment of bcap73 cDNA (SEQ ID NO:1) against Tentative Human Consensus (THC) Contiguous Sequences from the TIGR (Accession Nos. THC244788, THC186491, THC186491, THC213238).

DETAILED DESCRIPTION OF THE INVENTION

The present invention is based, at least in part, on the discovery of novel actin binding protein (ABP) family members, referred to herein as "beta-cap73" or "βcap73" or "bcap73" nucleic acid and protein molecules. ABP molecules modulate the proliferation, motility, differentiation, and survival of a variety of cells of mesodermal and/or neuroectodermal and/or ectodermal and/or endodermal origin, including fibroblasts, cells of the immune system, cells of the nervous system, cardiac muscle cells, skeletal muscle cells, vascular endothelial cells, vascular smooth muscle endothelial cells, and cells involved with repair of tissue injury.

Figure 1:
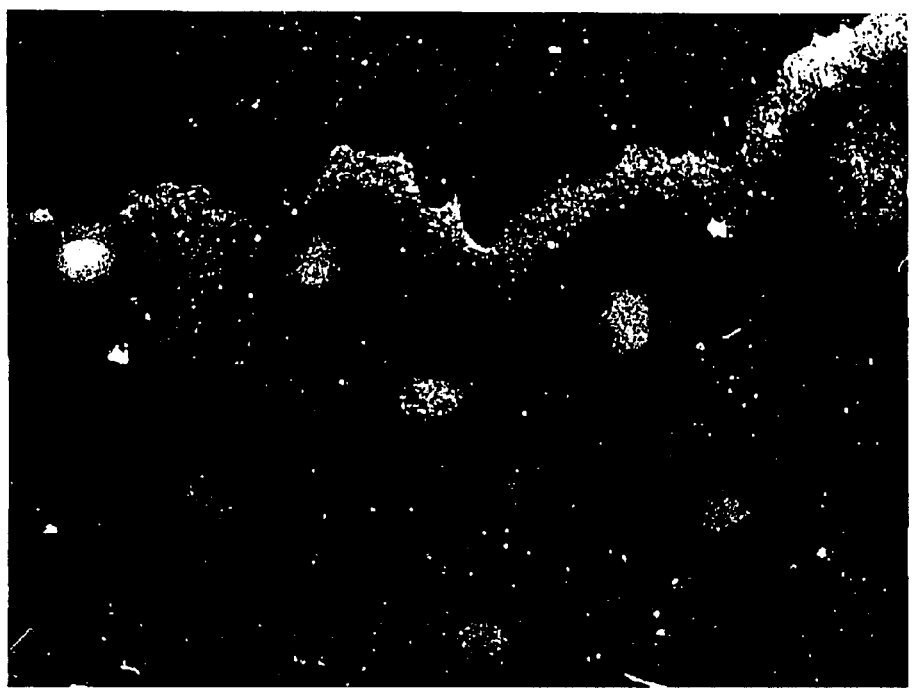
FIG. 1: A photograph of indirect immunofluorescence showing localization of bcap73 in cells that are moving into a wound (top). Also visible are contact-inhibited cells behind the wound edge which show no cortical enrichment of bcap73. Nuclear staining is background signal generated by the labelled tertiary antibody.
Figure 6:
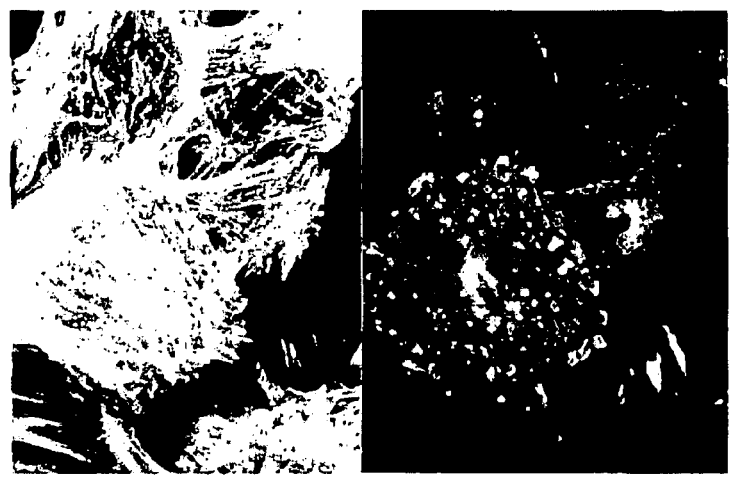
Figure 7A:
Figure 7B:
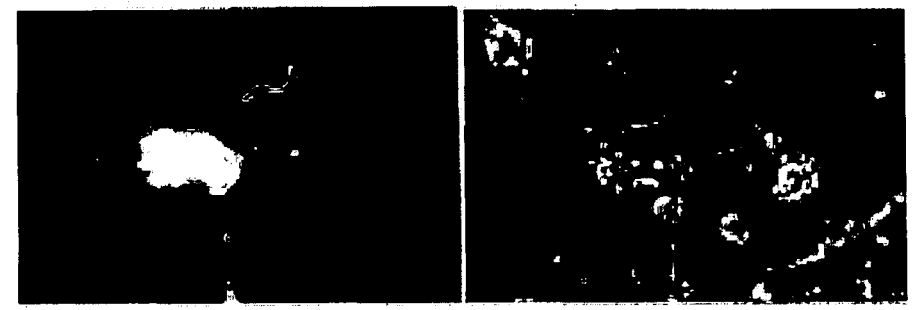
Figure 8:
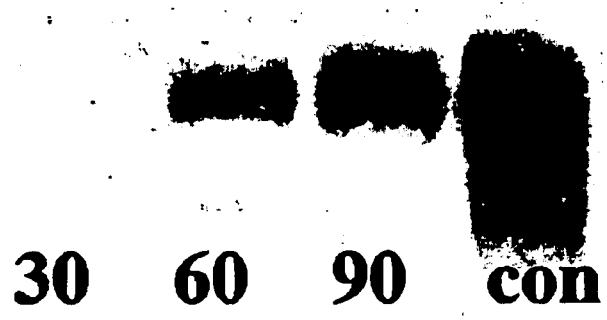

The bcap73 molecules of the present invention may also be motility regulatory proteins that function to modulate intracellular actin distribution, actin activity, changes in cytoskeletal structure, and response to tissue injury. Thus, the bcap73 molecules of the present invention may play a role in tissue repair mechanisms. As used herein, the term "tissue repair mechanisms" include mechanisms which regulate 1) intracellular actin distribution, 2) actin activity, 3) changes in cytoskeletal structure, 4) cell motility and migration 5) cellular response to tissue damage, and/or 6) repair of tissue damage. The ability of some cells, (e.g. vascular endothelial cells, vascular smooth muscle cells, fibroblasts, and keratinocytes) to move in response to stimuli (e.g. injury) depends upon their ability to coordinate directional assembly and disassembly of actin filaments of the cytoskeleton. The activity and cellular distribution of actin monomers and polymers are governed, at least in part, by "actin binding proteins" (ABPs) which interact with actin moieties. The bcap73 molecules of the present invention may be involved in such regulation of actin (FIGS. 6 and 7). Thus, the bcap73 molecules, by participating in regulation of actin activity and cytoskeletal rearrangement, may themselves modulate tissue repair mechanisms and act as targets and therapeutic agents for controlling tissue repair mechanisms (FIGS. 1 and 8).

Aberrant or excessive or insufficient expression of ABPs and their functional relatives which are involved in the regulation of actin function and intracellular actin distribution and cellular motility can lead to perturbed cellular functions, which in turn can lead to cellular disorders (or exacerbate existing cellular disorders). As used herein, a "cellular disorder" includes a disorder, disease, or condition characterized by aberrant or insufficient cellular ability to move or migrate properly in response to certain stimuli (e.g. tissue damage), or inability to properly regulate actin function and distribution within the cell. Thus, the bcap73 molecules may act as novel diagnostic targets and therapeutic agents for controlling cellular disorders related to motility, including cancer (e.g. tumor angiogenesis and metastasis). Additionally, bcap73 molecules may act as novel therapeutic agents for ameliorating certain cellular disorders and conditions through their ability to migrate and to regulate tissue injury response. As used herein, the terms "cellular disorders" and "conditions" include cardiovascular disorders and epidermal wounds. As used herein, the term "cardiovascular disorder" includes a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include congenital heart defects (e.g., atrioventricular canal defects), hypertension, atherosclerosis, coronary artery spasm, coronary artery disease, valvular disease, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, long-QT syndrome, congestive heart failure, sinus node dysfunction, atrial flutter, myocardial infarction, coronary artery spasm, arrhythmias, and cardiomyopathies. As used herein, the term "epidermal wounds" includes wounds suffered by burn victims, wounds suffered through surgical procedures, and wounds that are normally ameliorated through the actions of keratinocytes.

Bcap73-associated or related disorders also include disorders of tissues in which bcap73 is expressed, e.g., cardiac tissue, vascular system, skeletal muscle, and tissues of the nervous system. Bcap73-associated or related disorders can furthermore include disorders of tissues which can be affected or impacted by tissue in which bcap73 is normally expressed.

The bcap73 molecules of the present invention were identified from an injury response-activated bovine endothelial cDNA library. Vascular endothelial cells and keratinocytes contain the ability to respond to injury. Accordingly, the bcap73 molecules may also act as novel diagnostic targets and therapeutic agents for controlling or enhancing injury repair in a variety of disorders, diseases, or conditions. For example, the bcap73 molecules may provide novel diagnostic targets and therapeutic agents for controlling or enhancing the response elicited through various forms of vascular tissue injury, e.g., atherosclerosis, mechanical damage from balloon angioplasty, and tumor-induced angiogenesis.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., bovine and monkey proteins. Members of a family may also have common functional characteristics.

For example, sequence conservation among bcap73-related family members indicates that these proteins are likely to include at least one ankyrin repeat domain. As used herein, the term "ankyrin repeat domain" includes an amino acid sequence and/or protein structure that has one or more occurrences of the consensus amino acid sequence for an ankyrin repeat domain which comprises the following pattern:

G-x-T-[PA]-L-H-x-A-A-x-x-G-x-x-x-[VI]-[VA]-x-x-L-L-x-x-G-A-x-x-N-x-x-[TD] (SEQ ID NO: 4)

The signature patterns or consensus patterns described herein are described according to the following designation: all amino acids are indicated according to their universal single letter designation; "x" designates any amino acid; amino acids in brackets indicates any one of the amino acids within the brackets, e.g., [VI] indicates either V (valine) or I (isoleucine) in that amino acid position. Bovine bcap73 has such a signature pattern at about amino acid residues 55 to 85, 88 to 118, 121 to 151, 184 to 214, 217 to 247, and 250 to 280 of SEQ ID NO: 2.

By further example, the family of bcap73-related proteins are likely to comprise at least one, and preferably two, three, four, five, six, seven, eight, nine or more ankyrin repeat domains. As used herein, the term "ankyrin repeat domain" includes a protein domain involved in protein:protein interactions, having an amino acid sequence of about 20–40 amino acid residues and having a bit score for the alignment of the sequence to the ankyrin repeat domain of at least 1 (using hidden Markov model analysis; HMM). Preferably, an ankyrin repeat domain includes at least about 25–40, more preferably about 25–35 amino acid residues, or most preferably about 30–35 amino acids and has a bit score for the alignment of the sequence to the ankyrin repeat domain (HMM) of at least 3, 5, 10, 20, 30, 40, 50, or greater. The ankyrin repeat domain (HMM) has been assigned the PFAM Accession PF00023 (www.pfam.wustl.edu). Ankyrin repeats are described in, for example, Otto E. et al. (1991) *J. Biol. Chem.* 114:241–253, Hatada E. N. et al. (1992) *PNAS USA* 89:2489–2493, and Blank V. P. et al. (1992) *Trends Genet.* 8:144–149, the contents of which are incorporated herein by reference.

In another preferred embodiment, an ankyrin repeat domain includes at least about 20–80, or more preferably about 20–30 amino acid residues, and has at least 50–60% homology, preferably about 60–70%, more preferably about 70–80%, or about 80–90% homology with an ankyrin repeat domain of bovine bcap73 (residues 55 through 280 of SEQ ID NO: 2).

As a further example, sequence conservation among bcap73-related family members indicates that these proteins are likely to include at least one actin-binding domain. As used herein, the term "actin-binding domain" includes an amino acid sequence and/or protein structure that preferably associated with one or more specific surfaces of actin monomers and polymers.

In a preferred embodiment, an actin-binding domain among bcap73-related family members comprises a primary amino acid sequence which forms secondary and/or tertiary structures which comprise an alpha helical coiled coil domain. In a preferred embodiment, this domain would span at least one, more preferably two or three or more actin monomers. In a further preferred embodiment, this domain allows bcap73 to bind axially along the length of the actin filament at the actin filament end.

In another preferred embodiment, an actin-binding domain includes at least about 20–800, or more preferably about 20–450, or most preferably 50–150 or 100–120 amino acid residues, and has at least 50–60% homology, preferably about 60–70%, more preferably about 70–80%, or about 80–90% homology with an actin-binding domain of bovine bcap73. (located within about residues 940 through 1401, or within about residues 1120–1220 of SEQ ID NO: 2).

Accordingly, bcap73 proteins having at least 50–60% homology, preferably about 60–70%, more preferably about 70–80%, or about 80–90% homology with a ankyrin repeat domain of bovine bcap73 are within the scope of the invention. Furthermore, bcap73 proteins having at least 50–60% homology, preferably about 60–70%, more preferably about 70–80%, or about 80–90% homology with an actin binding domain of bovine bcap73 are also within the scope of the invention.

Isolated proteins of the present invention, preferably bcap73 proteins, have an amino acid sequence sufficiently identical to the amino acid sequence of SEQ ID NO: 2, or are encoded by a nucleotide sequence sufficiently identical to SEQ ID NO: 1 or 3. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, a "bcap73 activity", "biological activity of bcap73" or "functional activity of bcap73", refers to an activity exerted by a bcap73 protein, polypeptide or nucleic acid molecule on a bcap73 responsive cell or tissue, or on a bcap73 protein substrate, as determined in vivo, or in vitro, according to standard techniques. In one embodiment, a bcap73 activity is a direct activity, such as an association with a bcap73-target molecule. As used herein, a "target molecule" or "binding partner" is a molecule with which a bcap73 protein binds or interacts in nature, such that bcap73-mediated function is achieved. A bcap73 target molecule can be a non-bcap73 molecule or a bcap73 protein or polypeptide of the present invention. In an exemplary embodiment, a bcap73 target molecule is a bcap73 substrate, e.g., a β-actin or an ezrin molecule. Alternatively, a bcap73 activity is an indirect activity, such as a subcellular actin distribution or regulation of actin function or cell motility or response to tissue injury, mediated by interaction of the bcap73 protein with a bcap73 substrate, e.g., a β-actin or an ezrin molecule. Preferably, a bcap73 activity is the ability to act as an actin-binding factor and to modulate functions such as subcellular actin distribution, changes in cytoskeletal structure, cell motility, and response to injury.

Accordingly, another embodiment of the invention features isolated bcap73 proteins and polypeptides having a bcap73 activity. Preferred proteins are bcap73 proteins having at least one ankyrin repeat domain, and, preferably, a bcap73 activity. Other preferred proteins are bcap73 proteins having an actin binding domain and, preferably, a bcap73 activity. Yet other preferred proteins are bcap73 proteins having at least one ankyrin repeat domain and an actin binding domain and, preferably, a bcap73 activity. Additional preferred proteins have at least one ankyrin repeat domain and/or actin binding domain, and are, preferably, encoded by a nucleic acid molecule having a nucleotide sequence which hybridizes under stringent hybridization conditions to a nucleic acid molecule comprising the nucleotide sequence of SEQ ID NO: 1 or 3.

The nucleotide sequence of the isolated bovine bcap73 cDNA and the predicted amino acid sequence of the bovine bcap73 polypeptide are SEQ ID NO: 1 and 2 respectively and are shown in FIG. 4.

The bovine bcap73 gene, which is approximately 4736 nucleotides in length, encodes a protein of approximately 1401 amino acid residues in length, which has a predicted molecular weight of approximately 154 kDa, and an observed molecular weight of approximately 73 kDa.

Various aspects of the invention are described in further detail in the following subsections:

I. Isolated Nucleic Acid Molecules

One aspect of the invention pertains to isolated nucleic acid molecules that encode bcap73 proteins or biologically active portions thereof, as well as nucleic acid fragments sufficient for use as hybridization probes to identify bcap73-encoding nucleic acid molecules (e.g., bcap73 mRNA) and fragments for use as PCR primers for the amplification or mutation of bcap73 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated bcap73 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO: 1 or 3, or a portion thereof, can be isolated using standard molecular biology techniques and the sequence information provided herein. Using all or portion of the nucleic acid sequence of SEQ ID NO: 1 or 3, as a hybridization probe, bcap73 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO: 1or 3 can be isolated by the polymerase chain reaction (PCR) using synthetic oligonucleotide primers designed based upon the sequence of SEQ ID NO: 1 or 3.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to bcap73 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO: 1. The sequence of SEQ ID NO: 1 corresponds to the bovine bcap73 cDNA. This cDNA comprises sequences encoding the bovine bcap73 protein (i.e., "the coding region", from nucleotides 392–4597), the 5' untranslated sequences (nucleotides 1–391), as well as 3' untranslated sequences (nucleotides 4598–4736). Alternatively, the nucleic acid molecule can comprise only the coding region of SEQ ID NO: 1 (e.g., nucleotides 392–4597, corresponding to SEQ ID NO: 3).

In another preferred embodiment, an isolated nucleic acid molecule of the invention comprises a nucleic acid molecule which is a complement of the nucleotide sequence shown in SEQ ID NO: 1 or 3, or a portion of any of these nucleotide sequences. A nucleic acid molecule which is complementary to the nucleotide sequence shown in SEQ ID NO: 1 or 3, is one which is sufficiently complementary to the nucleotide sequence shown in SEQ ID NO: 1 or 3, such that it can hybridize to the nucleotide sequence shown in SEQ ID NO: 1 or 3, thereby forming a stable duplex.

In still another preferred embodiment, an isolated nucleic acid molecule of the present invention comprises a nucleotide sequence which is at least about 32.2%, 35%, 40%, 45%, 50%, 55%, 60%, 65%, 70%, 75%, 80%, 83%, 85%, 90%, 95%, 98% or more identical to the entire length of the nucleotide sequence shown in SEQ ID NO: 1 or 3, or a portion of any of these nucleotide sequences.

Moreover, the nucleic acid molecule of the invention can comprise only a portion of the nucleic acid sequence of SEQ ID NO: 1 or 3, for example, a fragment which can be used as a probe or primer or a fragment encoding a portion of a bcap73 protein, e.g., a biologically active portion of a bcap73 protein. The nucleotide sequence determined from the cloning of the bcap73 gene allows for the generation of probes and primers designed for use in identifying and/or cloning other bcap73 family members, as well as bcap73 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 1 or 3, of an anti-sense sequence of SEQ ID NO: 1 or 3, or of a naturally occurring allelic variant or mutant of SEQ ID NO: 1 or 3. In one embodiment, a nucleic acid molecule of the present invention comprises a nucleotide sequence which is greater than 1911, 1911–2000, 2000–2250, 2250–2500, 2500–2750, 2750–3000, 3000–3250, 3250–3500, 3500–3750, 3750–4000, 4000–4250, 4250–4500, 4500–4736, or more nucleotides in length and hybridizes under stringent hybridization conditions to a nucleic acid molecule of SEQ ID NO: 1 or 3. The lengths of nucleic acid molecules of the invention can be within a range using any one of the aforementioned numbers as the upper or lower limit of the range. For example, the nucleic acid molecules can be of a length greater than at least 1911 and/or 3000 nucleotides in length.

Probes based on the bcap73 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a bcap73 protein, such as by measuring a level of a bcap73-encoding nucleic acid in a sample of cells from a subject e.g., detecting bcap73 mRNA levels or determining whether a genomic bcap73 gene has been mutated or deleted.

A nucleic acid fragment encoding a "biologically active portion of a bcap73 protein" can be prepared by isolating a portion of the nucleotide sequence of SEQ ID NO: 1 or 3, which encodes a polypeptide having a bcap73 biological activity (the biological activities of the bcap73 proteins are described herein), expressing the encoded portion of the bcap73 protein (e.g., by recombinant expression in vitro) and assessing the activity of the encoded portion of the bcap73 protein.

The invention further encompasses nucleic acid molecules that differ from the nucleotide sequence shown in SEQ ID NO: 1 or 3, due to degeneracy of the genetic code and thus encode the same bcap73 proteins as those encoded by the nucleotide sequence shown in SEQ ID NO: 1 or 3. In another embodiment, an isolated nucleic acid molecule of the invention has a nucleotide sequence encoding a protein having an amino acid sequence shown in SEQ ID NO: 2.

In addition to the bcap73 nucleotide sequences shown in SEQ ID NO: 1 or 3, it will be appreciated by those skilled in the art that DNA sequence polymorphisms that lead to changes in the amino acid sequences of the bcap73 proteins may exist within a population (e.g., the human population). Such genetic polymorphism in the bcap73 genes may exist among individuals within a population due to natural allelic variation. As used herein, the terms "gene" and "recombinant gene" refer to nucleic acid molecules which include an open reading frame encoding a bcap73 protein, preferably a mammalian bcap73 protein, and can further include non-coding regulatory sequences, and introns.

Allelic variants of bovine bcap73 include both functional and non-functional bcap73 proteins. Functional allelic variants are naturally occurring amino acid sequence variants of the bovine bcap73 proteins that maintain the ability to bind a bcap73 ligand or substrate and/or modulate subcellular distribution of actin and/or actin function and/or changes in cytoskeletal structure and/or cell motility and/or response to tissue injury. Functional allelic variants will typically contain only conservative substitution of one or more amino acids of SEQ ID NO: 2, or substitution, deletion or insertion of non-critical residues in non-critical regions of the protein.

Non-functional allelic variants are naturally occurring amino acid sequence variants of the bovine bcap73 proteins that do not have the ability to either bind a bcap73 ligand or substrate and/or modulate cell proliferation and/or migration mechanisms. Non-functional allelic variants will typically contain a non-conservative substitution, a deletion, or insertion or premature truncation of the amino acid sequence of SEQ ID NO: 2, or a substitution, insertion or deletion in critical residues or critical regions.

The present invention further provides non-bovine orthologues of the bovine bcap73 proteins. Orthologues of the bovine bcap73 proteins are proteins that are isolated from non-bovine organisms and possess the same bcap73 ligand binding and/or modulation of subcellular actin distribution and/or actin function and/or changes in cytoskeletal structure and/or cell motility and/or response to tissue injury of the bovine bcap73 proteins. Orthologues of the bovine bcap73 proteins can readily be identified as comprising an amino acid sequence that is substantially identical to SEQ ID NO: 2.

Moreover, nucleic acid molecules encoding other bcap73 family members and, thus, which have a nucleotide sequence which differs from the bcap73 sequences of SEQ ID NO: 1 or 3 are intended to be within the scope of the invention. For example, another bcap73 cDNA can be identified based on the nucleotide sequence of bovine bcap73. Moreover, nucleic acid molecules encoding bcap73 proteins from different species, and which, thus, have a nucleotide sequence which differs from the bcap73 sequences of SEQ ID NO: 1 or 3 are intended to be within the scope of the invention. For example, a human bcap73 cDNA or a mouse bcap73 cDNA can be identified based on the nucleotide sequence of a bovine bcap73.

Nucleic acid molecules corresponding to natural allelic variants and homologues of the bcap73 cDNAs of the invention can be isolated based on their homology to the bcap73 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the bcap73 cDNAs of the invention can further be isolated by mapping to the same chromosome or locus as the bcap73 gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO: 1 or 3. In other embodiment, the nucleic acid is at least 30, 50, 100, 100, 150, 200, 250, 300, 350, 400, 450, 500, 550, 600, 650, 700, 750, 800, 900, 1000, 1100, 1200, 1400, 1600, 1800, 2000, 2200, 2400, 2600, 2800, 3000, 3200, 3400, 3600, 3800, 4000, 4200, 4400, 4600 or more nucleotides in length. The nucleic acid molecules of the invention can be of a length within a range which uses any one of the aforementioned numbers as the upper or lower limit of the range. For example, the nucleic acid molecules can be of a length between at least 30 and 250 nucleotides in length.

As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of SEQ ID NO: 1 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the bcap73 sequences that may exist in the population, the skilled artisan will further appreciate that changes can be introduced by mutation into the nucleotide sequences of SEQ ID NO: 1 or 3, thereby leading to changes in the amino acid sequence of the encoded bcap73 proteins, without altering the functional ability of the bcap73 proteins. For example, nucleotide substitutions leading to amino acid substitutions at "non-essential" amino acid residues can be made in the sequence of SEQ ID NO: 1 or 3. A "non-essential" amino acid residue is a residue that can be altered from the wild-type sequence of bcap73 (e.g., the sequence of SEQ ID NO: 2) without altering the biological activity, whereas an "essential" amino acid residue is required for biological activity. For example, amino acid residues that are conserved among the bcap73 proteins of the present invention, e.g., those present in the actin-binding domain and/or the actin-binding domain, are predicted to be particularly unamenable to alteration. Furthermore, additional amino acid residues that are conserved between the bcap73 proteins of the present invention and other members of the ABP family are not likely to be amenable to alteration.

Accordingly, another aspect of the invention pertains to nucleic acid molecules encoding bcap73 proteins that contain changes in amino acid residues that are not essential for activity. Such bcap73 proteins differ in amino acid sequence from SEQ ID NO: 2, yet retain biological activity. In one embodiment, the isolated nucleic acid molecule comprises a nucleotide sequence encoding a protein, wherein the protein comprises an amino acid sequence at least about 30%, 35%, 40%, 45%, 50%, 55%, 60%, 65%, 70%, 75%, 80%, 85%, 90%, 95%, 98% or more identical to SEQ ID NO: 2.

An isolated nucleic acid molecule encoding a bcap73 protein identical to the protein of SEQ ID NO: 2, can be created by introducing one or more nucleotide substitutions, additions or deletions into the nucleotide sequence of SEQ ID NO: 1 or 3, such that one or more amino acid substitutions, additions or deletions are introduced into the encoded protein. Mutations can be introduced into SEQ ID NO: 1 or 3, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a bcap73 protein is preferably replaced with another amino acid residue from the same side chain family. Alternatively, in another embodiment, mutations can be introduced randomly along all or part of a bcap73 coding sequence, such as by saturation mutagenesis, and the resultant mutants can be screened for bcap73 biological activity to identify mutants that retain activity. Following mutagenesis of SEQ ID NO: 1 or 3, the encoded protein can be expressed recombinantly and the activity of the protein can be determined.

In a preferred embodiment, a mutant bcap73 protein can be assayed for the ability to (1) interact with a non-bcap73 protein molecule, e.g., a bcap73 ligand or substrate; (2) activate a bcap73-dependent signal transduction pathway; or (3) modulate subcellular distribution of actin and/or actin function and/or changes in cytoskeletal structure and/or cell motility and/or response to tissue injury.

In addition to the nucleic acid molecules encoding bcap73 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire bcap73 coding strand, or to only a portion thereof. In one embodiment, an antisense nucleic acid molecule is antisense to a "coding region" of the coding strand of a nucleotide sequence encoding bcap73. The term "coding region" refers to the region of the nucleotide sequence comprising codons which are translated into amino acid residues (e.g., the coding region of bovine bcap73 corresponds to SEQ ID NO: 3). In another embodiment, the antisense nucleic acid molecule is antisense to a "noncoding region" of the coding strand of a nucleotide sequence encoding bcap73. The term "noncoding region" refers to 5' and 3' sequences which flank the coding region that are not translated into amino acids (i.e., also referred to as 5' and 3' untranslated regions).

Given the coding strand sequences encoding bcap73 disclosed herein (e.g., SEQ ID NO: 3), antisense nucleic acids of the invention can be designed according to the rules of Watson and Crick base pairing. The antisense nucleic acid molecule can be complementary to the entire coding region of bcap73 mRNA, but more preferably is an oligonucleotide which is antisense to only a portion of the coding or noncoding region of bcap73 mRNA. For example, the antisense oligonucleotide can be complementary to the region surrounding the translation start site of bcap73 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a bcap73 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave bcap73 mRNA transcripts to thereby inhibit translation of bcap73 mRNA. A ribozyme having specificity for a bcap73-encoding nucleic acid can be designed based upon the nucleotide sequence of a bcap73 cDNA disclosed herein (i.e., SEQ ID NO: 1 or 3). For example, a derivative of a Tetrahymena L-19 IVS RNA can be constructed in which the nucleotide sequence of the active site is complementary to the nucleotide sequence to be cleaved in a bcap73-encoding mRNA. See, e.g., Cech et al. U.S. Pat. No. 4,987,071; and Cech et al. U.S. Pat. No. 5,116,742. Alternatively, bcap73 mRNA can be used to select a catalytic RNA having a specific ribonuclease activity from a pool of RNA molecules. See, e.g., Bartel, D. and Szostak, J. W. (1993) *Science* 261:1411–1418.

Alternatively, bcap73 gene expression can be inhibited by targeting nucleotide sequences complementary to the regulatory region of the bcap73 (e.g., the bcap73 promoter and/or enhancers) to form triple helical structures that prevent transcription of the bcap73 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the bcap73 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1):5–23). As used herein, the terms "peptide nucleic acids" or "PNAS" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of bcap73 nucleic acid molecules can be used in therapeutic and diagnostic applications. For example, PNAs can be used as anti sense or antigene agents for sequence-specific modulation of gene expression by, for example, inducing transcription or translation arrest or inhibiting replication. PNAs of bcap73 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of bcap73 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of bcap73 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1 996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO89/09810) or the blood-brain barrier (see, e.g., PCT Publication No. WO89/10134). In addition, oligonucleotides can be modified with hybridization-triggered cleavage agents (See, e,g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated bcap73 Proteins and Anti-bcap73 Antibodies

One aspect of the invention pertains to isolated bcap73 proteins, and biologically active portions thereof, as well as polypeptide fragments suitable for use as immunogens to raise anti-bcap73 antibodies. In one embodiment, native bcap73 proteins can be isolated from cells or tissue sources by an appropriate purification scheme using standard protein purification techniques. In another embodiment, bcap73 proteins are produced by recombinant DNA techniques. Alternative to recombinant expression, a bcap73 protein or polypeptide can be synthesized chemically using standard peptide synthesis techniques.

An "isolated" or "purified" protein or biologically active portion thereof is substantially free of cellular material or other contaminating proteins from the cell or tissue source from which the bcap73 protein is derived, or substantially free from chemical precursors or other chemicals when chemically synthesized. The language "substantially free of cellular material" includes preparations of bcap73 protein in which the protein is separated from cellular components of the cells from which it is isolated or recombinantly produced. In one embodiment, the language "substantially free of cellular material" includes preparations of bcap73 protein having less than about 30% (by dry weight) of non-bcap73 protein (also referred to herein as a "contaminating protein"), more preferably less than about 20% of non-bcap73 protein, still more preferably less than about 10% of non-bcap73 protein, and most preferably less than about 5% non-bcap73 protein. When the bcap73 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of bcap73 protein in which the protein is separated from chemical precursors or other chemicals which are involved in the synthesis of the protein. In one embodiment, the language "substantially free of chemical precursors or other chemicals" includes preparations of bcap73 protein having less than about 30% (by dry weight) of chemical precursors or non-bcap73 chemicals, more preferably less than about 20% chemical precursors or non-bcap73 chemicals, still more preferably less than about 10% chemical precursors or non-bcap73 chemicals, and most preferably less than about 5% chemical precursors or non-bcap73 chemicals.

As used herein, a "biologically active portion" of a bcap73 protein includes a fragment of a bcap73 protein which participates in an interaction between a bcap73 molecule and a non-bcap73 molecule. Biologically active portions of a bcap73 protein include peptides comprising amino acid sequences sufficiently identical to or derived from the amino acid sequence of the bcap73 protein, e.g., the amino acid sequence shown in SEQ ID NO: 2, which include less amino acids than the full length bcap73 proteins, and exhibit at least one activity of a bcap73 protein. Typically, biologically active portions comprise a domain or motif with at least one activity of the bcap73 protein, e.g., modulating cell proliferation mechanisms. A biologically active portion of a bcap73 protein can be a polypeptide which is, for example, 10, 25, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400 or more amino acids in length. Biologically active portions of a bcap73 protein can be used as targets for developing agents which modulate a bcap73 mediated activity, e.g., modulation of subcellular distribution of actin and/or actin function and/or changes in cytoskeletal structure and/or cell motility and/or response to tissue injury.

In one embodiment, a biologically active portion of a bcap73 protein comprises at least one ankyrin repeat domain, and/or at least one actin-binding domain. It is to be understood that a preferred biologically active portion of a bcap73 protein of the present invention may contain at least one ankyrin repeat domain. Another preferred biologically active portion of a bcap73 protein may contain at least one actin-binding domain. Moreover, other biologically active portions, in which other regions of the protein are deleted, can be prepared by recombinant techniques and evaluated for one or more of the functional activities of a native bcap73 protein.

In a preferred embodiment, the bcap73 protein has an amino acid sequence shown in SEQ ID NO: 2. In other embodiments, the bcap73 protein is substantially identical to SEQ ID NO: 2, and retains the functional activity of the protein of SEQ ID NO: 2, yet differs in amino acid sequence due to natural allelic variation or mutagenesis, as described in detail in subsection I above. Accordingly, in another embodiment, the bcap73 protein is a protein which comprises an amino acid sequence at least about 30%, 35%, 40%, 45%, 50%, 55%, 60%, 65%, 70%, 75%, 80%, 85%, 90%, 95%, 98% or more identical to SEQ ID NO: 2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the bcap73 amino acid sequence of SEQ ID NO: 2 having 1401 amino acid residues, at least 420, preferably at least 560, more preferably at least 701, even more preferably at least 841, and even more preferably at least 981, 1121 or 1261 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using:a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to bcap73 nucleic acid molecules of the invention. BLAST protein searches can be performed with the XBLAST program, score=100, wordlength=3 to obtain amino acid sequences homologous to bcap73 protein molecules of the invention. To obtain gapped alignments for comparison purposes, Gapped BLAST can be utilized as described in Altschul et al., (1997) *Nucleic Acids Res.* 25(17) :3389–3402. When utilizing BLAST and Gapped BLAST programs, the default parameters of the respective programs (e.g., XBLAST and NBLAST) can be used. See http://www.ncbi.nlm.nih.gov.

The invention also provides bcap73 chimeric or fusion proteins. As used herein, a bcap73 "chimeric protein" or "fusion protein" comprises a bcap73 polypeptide operatively linked to a non-bcap73 polypeptide. A "bcap73 polypeptide" refers to a polypeptide having an amino acid sequence corresponding to bcap73, whereas a "non-bcap73 polypeptide" refers to a polypeptide having an amino acid sequence corresponding to a protein which is not substantially homologous to the bcap73 protein, e.g., a protein which is different from the bcap73 protein and which is derived from the same or a different organism. Within a bcap73 fusion protein the bcap73 polypeptide can correspond to all or a portion of a bcap73 protein. In a preferred embodiment, a bcap73 fusion protein comprises at least one biologically active portion of a bcap73 protein. In another preferred embodiment, a bcap73 fusion protein comprises at least two biologically active portions of a bcap73 protein. Within the fusion protein, the term "operatively linked" is intended to indicate that the bcap73 polypeptide and the non-bcap73 polypeptide are fused in-frame to each other. The non-bcap73 polypeptide can be fused to the N-terminus or C-terminus of the bcap73 polypeptide.

For example, in one embodiment, the fusion protein is a GST-bcap73 fusion protein in which the bcap73 sequences are fused to the C-terminus of the GST sequences. Such fusion proteins can facilitate the purification of recombinant bcap73.

In a further embodiment, the fusion protein is a 6×His-bcap73 fusion protein in which six consecutive histidine residues are fused to the N-terminus, or the C-terminus, or embedded within the amino acid sequence of bcap73 protein. Such fusion proteins can facilitate the detection and chromatographic purification of recombinant bcap73 and associated proteins.

In another embodiment, the fusion protein is a bcap73 protein containing a heterologous signal sequence at its N-terminus. In certain host cells (e.g., mammalian host cells), expression and/or secretion of bcap73 can be increased through use of a heterologous signal sequence.

The bcap73 fusion proteins of the invention can be incorporated into pharmaceutical compositions and administered to a subject in vivo. The bcap73 fusion proteins can be used to affect the bioavailability of a bcap73 substrate. Use of bcap73 fusion proteins may be useful therapeutically for the treatment of disorders caused by, for example, (i) aberrant modification or mutation of a gene encoding a bcap73 protein; (ii) mis-regulation of the bcap73 gene; (iii) aberrant post-translational modification of a bcap73 protein; (iv) wildtype activity that is insufficient for therapeutic purposes; and (v) wildtype activity that is overabundant for therapeutic purposes.

Moreover, the bcap73-fusion proteins of the invention can be used as immunogens to produce anti-bcap73 antibodies in a subject, to purify bcap73 ligands and in screening assays to identify molecules which inhibit the interaction of bcap73 with a bcap73 substrate.

Preferably, a bcap73 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A bcap73-encoding nucleic acid can be cloned into such an expression vector such that the fusion moiety is linked in-frame to the bcap73 protein.

The present invention also pertains to variants of the bcap73 proteins which function as either bcap73 agonists (mimetics) or as bcap73 antagonists. Variants of the bcap73 proteins can be generated by mutagenesis, e.g., discrete point mutation or truncation of a bcap73 protein. An agonist of the bcap73 proteins can retain substantially the same, or a subset, of the biological activities of the naturally occurring form of a bcap73 protein. An antagonist of a bcap73 protein can inhibit one or more of the activities of the naturally occurring form of the bcap73 protein by, for example, competitively modulating a bcap73-mediated activity of a bcap73 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the bcap73 protein.

In one embodiment, variants of a bcap73 protein which function as either bcap73 agonists (mimetics) or as bcap73 antagonists can be identified by screening combinatorial libraries of mutants, e.g., truncation mutants, of a bcap73 protein for bcap73 protein agonist or antagonist activity. In one embodiment, a variegated library of bcap73 variants is generated by combinatorial mutagenesis at the nucleic acid level and is encoded by a variegated gene library. A variegated library of bcap73 variants can be produced by, for example, enzymatically ligating a mixture of synthetic oligonucleotides into gene sequences such that a degenerate set of potential bcap73 sequences is expressible as individual polypeptides, or alternatively, as a set of larger fusion proteins (e.g., for phage display) containing the set of bcap73 sequences therein. There are a variety of methods which can be used to produce libraries of potential bcap73 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential bcap73 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a bcap73 protein coding sequence can be used to generate a variegated population of bcap73 fragments for screening and subsequent selection of variants of a bcap73 protein. In one embodiment, a library of coding sequence fragments can be generated by treating a double stranded PCR fragment of a bcap73 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the bcap73 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of bcap73 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify bcap73 variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated bcap73 library. For example, a library of expression vectors can be transfected into a cell line, e.g., an endothelial cell line, which ordinarily responds to bcap73 in a particular bcap73 substrate-dependent manner. The transfected cells are then contacted with bcap73 and the effect of expression of the mutant on signaling by the bcap73 substrate can be detected, e.g., by monitoring intracellular calcium, IP3, or diacylglycerol concentration, phosphorylation profile of intracellular proteins, cell proliferation and/or migration, or the activity of an bcap73-regulated transcription factor. Plasmid DNA can then be recovered from the cells which score for inhibition, or alternatively, potentiation of signaling by the bcap73 substrate, and the individual clones further characterized.

An isolated bcap73 protein, or a portion or fragment thereof, can be used as an immunogen to generate antibodies that bind bcap73 using standard techniques for polyclonal and monoclonal antibody preparation. A full-length bcap73 protein can be used or, alternatively, the invention provides antigenic peptide fragments of bcap73 for use as immunogens. The antigenic peptide of bcap73 comprises at least 8 amino acid residues of the amino acid sequence shown in SEQ ID NO: 2 and encompasses an epitope of bcap73 such that an antibody raised against the peptide forms a specific immune complex with bcap73. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of bcap73 that are located on the surface of the protein, e.g., hydrophilic regions, as well as regions with high antigenicity.

A bcap73 immunogen typically is used to prepare antibodies by immunizing a suitable subject, (e.g., rabbit, goat, mouse or other mammal) with the immunogen. An appropriate immunogenic preparation can contain, for example, recombinantly expressed bcap73 protein or a chemically synthesized bcap73 polypeptide. The preparation can further include an adjuvant, such as Freund's complete or incomplete adjuvant, or similar immunostimulatory agent. Immunization of a suitable subject with an immunogenic bcap73 preparation induces a polyclonal anti-bcap73 antibody response.

Accordingly, another aspect of the invention pertains to anti-bcap73 antibodies. The term "antibody" as used herein refers to immunoglobulin molecules and immunologically active portions of immunoglobulin molecules, i.e., molecules that contain an antigen binding site which specifically binds (immunoreacts with) an antigen, such as bcap73. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind bcap73. The term "monoclonal antibody" or "monoclonal antibody composition", as used herein, refers to a population of antibody molecules that contain only one species of an antigen binding site capable of immunoreacting with a particular epitope of bcap73. A monoclonal antibody composition thus typically displays a single binding affinity for a particular bcap73 protein with which it immunoreacts.

Polyclonal anti-bcap73 antibodies can be prepared as described above by immunizing a suitable subject with a bcap73 immunogen. The anti-bcap73 antibody titer in the immunized subject can be monitored over time by standard techniques, such as with an enzyme linked immunosorbent assay (ELISA) using immobilized bcap73. If desired, the antibody molecules directed against bcap73 can be isolated from the mammal (e.g., from the blood) and further purified by well known techniques, such as protein A chromatography to obtain the IgG fraction. At an appropriate time after immunization, e.g., when the anti-bcap73 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic*

Cell Genet. 3:231–36). Briefly, an immortal cell line (typically a myeloma) is fused to lymphocytes (typically splenocytes) from a mammal immunized with a bcap73 immunogen as described above, and the culture supernatants of the resulting hybridoma cells are screened to identify a hybridoma producing a monoclonal antibody that binds bcap73.

Any of the many well known protocols used for fusing lymphocytes and immortalized cell lines can be applied for the purpose of generating an anti-bcap73 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind bcap73, e.g., using a standard ELISA assay.

Alternative to preparing monoclonal antibody-secreting hybridomas, a monoclonal anti-bcap73 antibody can be identified and isolated by screening a recombinant combinatorial immunoglobulin library (e.g., an antibody phage display library) with bcap73 to thereby isolate immunoglobulin library members that bind bcap73. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) Nuc. Acid Res. 19:4133–4137; Barbas et al. (1991) *Proc. Natl. Acad. Sci. USA* 88:7978–7982; and McCafferty et al. *Nature* (1990) 348:552–554.

Additionally, recombinant anti-bcap73 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-bcap73 antibody (e.g., monoclonal antibody) can be used to isolate bcap73 by standard techniques, such as affinity chromatography or immunoprecipitation. An anti-bcap73 antibody can facilitate the purification of natural bcap73 from cells and of recombinantly produced bcap73 expressed in host cells. Moreover, an anti-bcap73 antibody can be used to detect bcap73 protein (e.g., in a cellular lysate or cell supernatant) in order to evaluate the abundance and pattern of expression of the bcap73 protein. Anti-bcap73 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a bcap73 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., bcap73 proteins, mutant forms of bcap73 proteins, fusion proteins, and the like).

The recombinant expression vectors of the invention can be designed for expression of bcap73 proteins in prokaryotic or eukaryotic cells. For example, bcap73 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in bcap73 activity assays, (e.g., direct assays or competitive assays described in detail below), or to generate antibodies specific for bcap73 proteins, for example. In a preferred embodiment, a bcap73 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the bcap73 expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (In Vitrogen Corp, San Diego, Calif.).

Alternatively, bcap73 proteins can be expressed in insect cells using baculovirus expression vectors. Baculovirus vectors available for expression of proteins in cultured insect cells (e.g., Sf 9 cells) include the pAc series (Smith et al.

(1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter, U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546). Also known in the art are eukaryotic promoters which are specific for vascular endothelial cells (for example, the tie-2 promoter) and eukaryotic promoters which are specific for vascular smooth muscle cells (for example, the SM22 promoter) and eukaryotic promoters which are specific for keratinocytes. In a preferred embodiment, tissue-specific promoters are used to direct expression of bcap73 molecules of the invention in vascular smooth muscle cells and/or vascular endothelial cells in order to ameliorate vascular and/or arterial injury, including injury related to arterial occlusion and/or atherosclerosis and/or balloon angioplasty. In a further preferred embodiment, tissue specific promoters are used to direct expression of bcap73 molecules of the invention to enhance the reparative response of keratinocytes and/or fibroblasts to-epidermal wounds, including burns and wounds from surgery. In a further preferred embodiment, tissue specific promoters are used to direct expression of bcap73 molecules of the invention to hamper or block endothelial migration associated with certain angiogenesis event; e.g. those associated with tumors and carcinomas.

The expression characteristics of an endogenous bcap73 gene within a cell line or microorganism may be modified by inserting a heterologous DNA regulatory element into the genome of a stable cell line or cloned microorganism such that the inserted regulatory element is operatively linked with the endogenous bcap73 gene. For example, an endogenous bcap73 gene which is normally "transcriptionally silent", i.e., a bcap73 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous bcap73 gene may be activated by insertion of a promiscuous regulatory element that works across cell types.

A heterologous regulatory element may be inserted into a stable cell line or cloned microorganism, such that it is operatively linked with an endogenous bcap73 gene, using techniques, such as targeted homologous recombination, which are well known to those of skill in the art, and described, e.g., in Chappel, U.S. Pat. No. 5,272,071; PCT publication No. WO 91/06667, published May 16, 1991.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to bcap73 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a bcap73 nucleic acid molecule of the invention is introduced, e.g., a bcap73 nucleic acid molecule within a recombinant expression vector or a bcap73 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a bcap73 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a bcap73 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a bcap73 protein. Accordingly, the invention further provides methods for producing a bcap73 protein using the host cells of the invention. In one embodiment, the method comprises culturing the host cell of the invention (into which a recombinant expression vector encoding a bcap73 protein has been introduced) in a suitable medium such that a bcap73 protein is produced. In another embodiment, the method further comprises isolating a bcap73 protein from the medium or the host cell.

The host cells of the invention can also be used to produce non-human transgenic animals. For example, in one embodiment, a host cell of the invention is a fertilized oocyte or an embryonic stem cell into which bcap73-coding sequences have been introduced. Such host cells can then be used to create non-human transgenic animals in which exogenous bcap73 sequences have been introduced into their genome or homologous recombinant animals in which endogenous bcap73 sequences have been altered. Such animals are useful for studying the function and/or activity of a bcap73 and for identifying and/or evaluating modulators of bcap73 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous bcap73 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a bcap73-encoding nucleic acid into the male pronuclei of a fertilized oocyte, e.g., by microinjection, retroviral infection, and allowing the oocyte to develop in a pseudopregnant female foster animal. The bcap73 cDNA sequence of SEQ ID NO: 1 can be introduced as a transgene into the genome of a non-human animal. Alternatively, a non-human homologue of a human bcap73 gene, such as a mouse or rat bcap73 gene, can be used as a transgene. Alternatively, a bcap73 gene homologue, such as another bcap73 family member, can be isolated based on hybridization to the bcap73 cDNA sequences of SEQ ID NO: 1(described further in subsection I above) and used as a transgene. Intronic sequences and polyadenylation signals can also be included in the transgene to increase the efficiency of expression of the transgene. A tissue-specific regulatory sequence(s) can be operably linked to a bcap73 transgene to direct expression of a bcap73 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a bcap73 transgene in its genome and/or expression of bcap73 mRNA in tissues or cells of the animals. A transgenic founder animal can then be used to breed additional animals carrying the transgene. Moreover, transgenic animals carrying a transgene encoding a bcap73 protein can further be bred to other transgenic animals carrying other transgenes.

To create a homologous recombinant animal, a vector is prepared which contains at least a portion of a bcap73 gene into which a deletion, addition or substitution has been introduced to thereby alter, e.g., functionally disrupt, the bcap73 gene. The bcap73 gene can be a bovine gene (e.g., the cDNA of SEQ ID NO: 3), but more preferably, is a non-human homologue of a bovine bcap73 gene (e.g., a cDNA isolated by stringent hybridization with the nucleotide sequence of SEQ ID NO: 1). For example, a mouse bcap73 gene can be used to construct a homologous recombination nucleic acid molecule, e.g., a vector, suitable for altering an endogenous bcap73 gene in the mouse genome. In a preferred embodiment, the homologous recombination nucleic acid molecule is designed such that, upon homologous recombination, the endogenous bcap73 gene is functionally disrupted (i.e., no longer encodes a functional protein; also referred to as a "knock out" vector). Alternatively, the homologous recombination nucleic acid molecule can be designed such that, upon homologous recombination, the endogenous bcap73 gene is mutated or otherwise altered but still encodes functional protein (e.g., the upstream regulatory region can be altered to thereby alter the expression of the endogenous bcap73 protein). In the homologous recombination nucleic acid molecule, the altered portion of the bcap73 gene is flanked at its 5' and 3' ends by additional nucleic acid sequence of the bcap73 gene to allow for homologous recombination to occur between the exogenous bcap73 gene carried by the homologous recombination nucleic acid molecule and an endogenous bcap73 gene in a cell, e.g., an embryonic stem cell. The additional flanking bcap73 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced bcap73 gene has homologously recombined with the endogenous bcap73 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 9210968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT. International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The bcap73 nucleic acid molecules, fragments of bcap73 proteins, and anti-bcap73 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a bcap73 protein or an anti-bcap73 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may-be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin,mitomycin C, and cis-dichlorodiamine platinum(II) (DDP)cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470), stereotactic injection (see e.g., Chen et al. (1994) *Proc. Natl. Acad Sci. USA* 91:3054–3057), or by balloon catheter in conjunction with angioplasty. The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. Cells types which can be modified for gene therapy purposes include hematopoietic stem cells, myoblasts, hepatocytes, lymphocytes, skin epithelium and airway epithelium. For further descriptions of cell types, genes and methods for gene therapy see e.g., Wilson, J. M et al. (1988) *Proc. Natl Acad. Sci. USA* 85:3014–3018; Armentano, D. et al. (1990) *Proc. Natl. Acad. Sci. USA* 87:6141–6145; Wolff, J. A. et al. (1990) *Science* 247:1465–1468; Chowdhury, J. R. et al. (1991) *Science* 254:1802–1805; Ferry, N. et al. (1991) *Proc. Natl. Acad. Sci. USA* 88:8377–8381; Wilson, J. M. et al. (1992) *J. Biol. Chem.* 267:963–967; Quantin, B. et al. (1992) *Proc. Natl. Acad. Sci. USA* 89:2581–2584; Dai, Y. et al. (1992) *Proc. Natl. Acad. Sci. USA* 89:10892–10895; van Beusechem, V. W. et al. (1992) *Proc. Natl. Acad. Sci. USA* 89:7640–7644; Rosenfeld, M. A. et al. (1992) *Cell* 68:143–155; Kay, M. A. et al. (1992) *Human Gene Therapy* 3:641–647; Cristiano, R. J. et al. (1993) *Proc. Nat. Acad. Sci. USA* 90:2122–2126; Hwu, P. et al. (1993) *J. Immunol.* 150:4104–4115; and Herz, J. and Gerard, R. D. (1993) *Proc. Natl. Acad. Sci. USA* 90:2812–2816.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a bcap73 protein of the invention has one or more of the following activities: (1) it interacts with a non-bcap73 protein molecule, e.g., a bcap73 substrate, such as an actin molecule or an ezrin molecule; (2) it is involved with intracellular distribution and activity of actin; (3) it is involved in regulating changes in cytoskeletal structure; (4) it in involved with mechanisms of cell motility, and (5) it is involved with mechanisms of response to tissue damage and repair of tissue damage, and, thus, can be used to, for example, (1) interact with a non-bcap73 protein molecule, e.g., a bcap73 substrate, such as an actin molecule or an ezrin molecule; (2) affect intracellular distribution and activity of actin; (3) regulate changes in cytoskeletal structure; (4) affect mechanisms of cell motility; and (5) affect mechanisms of response to tissue damage and repair of tissue damage.

The isolated nucleic acid molecules of the invention can be used, for example, to express bcap73 protein (e.g., via a recombinant expression vector in a host cell in gene therapy applications), to detect bcap73 mRNA (e.g., in a biological sample) or a genetic alteration in a bcap73 gene, and to modulate bcap73 activity, as described further below. The bcap73 proteins can be used to treat disorders characterized by insufficient or excessive production of a bcap73 substrate or production of bcap73 inhibitors. In addition, the bcap73 proteins can be used to screen for naturally occurring bcap73 substrates, to screen for drugs, or compounds which modulate bcap73 activity, as well as to treat disorders characterized by insufficient or excessive production of bcap73 protein or production of bcap73 protein forms which have decreased, aberrant or unwanted activity compared to bcap73 wild type protein (e.g., cell motility disorders, cytoskeletal disorders neurodegenerative disorders, cardiovascular disorders, or tissue repair). Moreover, the anti-bcap73 antibodies of the invention can be used to detect and isolate bcap73 proteins, regulate the bioavailability of bcap73 proteins, and modulate bcap73 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to bcap73 proteins, have a stimulatory or inhibitory effect on, for example, bcap73 expression or bcap73 activity, or have a stimulatory or inhibitory effect on, for example, the expression or activity of bcap73 substrate.

In one embodiment, the invention provides assays for screening candidate or test compounds which are substrates of a bcap73 protein or polypeptide or biologically active portion thereof. In another embodiment, the invention provides assays for screening candidate or test compounds which bind to or modulate the activity of a bcap73 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al.-(1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a bcap73 protein or biologically active portion thereof is contacted with a test compound and the ability of the test compound to modulate bcap73 activity is determined. Determining the ability of the test compound to modulate bcap73 activity can be accomplished by monitoring, for example, intracellular calcium, IP3, or diacylglycerol concentration, phosphorylation profile of intracellular proteins, cell proliferation and/or migration, or the activity of an bcap73-regulated transcription factor. The cell, for example, can be of mammalian origin, e.g., an endothelial cell.

The ability of the test compound to modulate bcap73 binding to a substrate or to bind to bcap73 can also be determined. Determining the ability of the test compound to modulate bcap73 binding to a substrate can be accomplished, for example, by coupling the bcap73 substrate with a radioisotope or enzymatic label such that binding of the bcap73 substrate to bcap73 can be determined by detecting the labeled bcap73 substrate in a complex. Alternatively, bcap73 could be coupled with a radioisotope or enzymatic label to monitor the ability of a test compound to modulate bcap73 binding to a bcap73 substrate in a complex. Determining the ability of the test compound to bind bcap73 can be accomplished, for example, by coupling the compound with a radioisotope or enzymatic label such that binding of the compound to bcap73 can be determined by detecting the labeled bcap73 compound in a complex. For example, compounds (e.g., bcap73 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a bcap73 substrate) to interact with bcap73 without the labeling of any of the interactants. For example, a microphysiometer can be used to detect the interaction of a compound with bcap73 without the labeling of either the compound or the bcap73. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and bcap73.

In another embodiment, an assay is a cell-based assay comprising contacting a cell expressing a bcap73 target molecule (e.g., a bcap73 substrate) with a test compound and determining the ability of the test compound to modulate (e.g., stimulate or inhibit) the activity of the bcap73 target molecule. Determining the ability of the test compound to modulate the activity of a bcap73 target molecule can be accomplished, for example, by determining the ability of the bcap73 protein to bind to or interact with the bcap73 target molecule.

Determining the ability of the bcap73 protein or a biologically active fragment thereof, to bind to or interact with a bcap73 target molecule can be accomplished by one of the methods described above for determining direct binding. In a preferred embodiment, determining the ability of the bcap73 protein to bind to or interact with a bcap73 target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a bcap73 protein or biologically active portion thereof is contacted with a test compound and the ability of the test compound to bind to the bcap73 protein or biologically active portion thereof is determined. Preferred biologically active portions of the bcap73 proteins to be used in assays of the present invention include fragments which participate in interactions with non-bcap73 molecules, e.g., fragments with high surface probability scores. Binding of the test compound to the bcap73 protein can be determined either directly or indirectly as described above. In a preferred embodiment, the assay includes contacting the bcap73 protein or biologically active portion thereof with a known compound which binds bcap73 to form an assay mixture, contacting the assay mixture with a test compound, and determining the ability of the test compound to interact with a bcap73 protein, wherein determining the ability of the test compound to interact with a bcap73 protein comprises determining the ability of the test compound to preferentially bind to bcap73 or biologically active portion thereof as compared to the known compound.

In another embodiment, the assay is a cell-free assay in which a bcap73 protein or biologically active portion thereof is contacted with a test compound and the ability of the test compound to modulate (e.g., stimulate or inhibit) the activity of the bcap73 protein or biologically active portion thereof is determined. Determining the ability of the test compound to modulate the activity of a bcap73 protein can be accomplished, for example, by determining the ability of the bcap73 protein to bind to a bcap73 target molecule by one of the methods described above for determining direct binding. Determining the ability of the bcap73 protein to bind to a bcap73 target molecule can also be accomplished using a technology such as real-time Biomolecular Interaction Analysis (BIA). Sjolander, S. and Urbaniczky,C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a bcap73 protein can be accomplished by determining the ability of the bcap73 protein to further modulate the activity of a downstream effector of a bcap73 target molecule. For example, the activity of the effector molecule on an appropriate target can be determined or the binding of the effector to an appropriate target can be determined as previously described.

In yet another embodiment, the cell-free assay involves contacting a bcap73 protein or biologically active portion thereof with a known compound which binds the bcap73 protein to form an assay mixture, contacting the assay mixture with a test compound, and determining the ability of the test compound to interact with the bcap73 protein, wherein determining the ability of the test compound to interact with the bcap73 protein comprises determining the ability of the bcap73 protein to preferentially bind to or modulate the activity of a bcap73 target molecule.

In more than one embodiment of the above assay methods of the present invention, it may be desirable to immobilize either bcap73 or its target molecule to facilitate separation of complexed from uncomplexed forms of one or both of the proteins, as well as to accommodate automation of the assay. Binding of a test compound to a bcap73 protein, or interaction of a bcap73 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/bcap73 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or bcap73 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of bcap73 binding or activity determined using standard techniques.

Other techniques for immobilizing proteins on matrices can also be used in the screening assays of the invention. For example, either a bcap73 protein or a bcap73 target molecule can be immobilized utilizing conjugation of biotin and streptavidin. Biotinylated bcap73 protein or target molecules can be prepared from biotin-NHS (N-hydroxy-succinimide)

using techniques known in the art (e.g., biotinylation kit, Pierce Chemicals, Rockford, Ill.), and immobilized in the wells of streptavidin-coated 96 well plates (Pierce Chemical). Alternatively, antibodies reactive with bcap73 protein or target molecules but which do not interfere with binding of the bcap73 protein to its target molecule can be derivatized to the wells of the plate, and unbound target or bcap73 protein trapped in the wells by antibody conjugation. Methods for detecting such complexes, in addition to those described above for the GST-immobilized complexes, include immunodetection of complexes using antibodies reactive with the bcap73 protein or target molecule, as well as enzyme-linked assays which rely on detecting an enzymatic activity associated with the bcap73 protein or target molecule.

In another embodiment, modulators of bcap73 expression are identified in a method wherein a cell is contacted with a candidate compound and the expression of bcap73 mRNA or protein in the cell is determined. The level of expression of bcap73 mRNA or protein in the presence of the candidate compound is compared to the level of expression of bcap73 mRNA or protein in the absence of the candidate compound. The candidate compound can then be identified as a modulator of bcap73 expression based on this comparison. For example, when expression of bcap73 mRNA or protein is greater (statistically significantly greater) in the presence of the candidate compound than in its absence, the candidate compound is identified as a stimulator of bcap73 mRNA or protein expression. Alternatively, when expression of bcap73 mRNA or protein is less (statistically significantly less) in the presence of the candidate compound than in its absence, the candidate compound is identified as an inhibitor of bcap73 mRNA or protein expression. The level of bcap73 mRNA or protein expression in the cells can be determined by methods described herein for detecting bcap73 mRNA or protein.

In yet another aspect of the invention, the bcap73 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with bcap73 ("bcap73-binding proteins" or "bcap73-bp") and are involved in bcap73 activity. Such bcap73-binding proteins are also likely to be involved in the propagation of signals by the bcap73 proteins or bcap73 targets as, for example, downstream elements of a bcap73-mediated signaling pathway. Alternatively, such bcap73-binding proteins are likely to be bcap73 inhibitors.

The two-hybrid system is based on the modular nature of most transcription factors, which consist of separable DNA-binding and activation domains. Briefly, the assay utilizes two different DNA constructs. In one construct, the gene that codes for a bcap73 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a bcap73-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the bcap73 protein.

In another aspect, the invention pertains to a combination of two or more of the assays described herein. For example, a modulating agent can be identified using a cell-based or a cell free assay, and the ability of the agent to modulate the activity of a bcap73 protein can be confirmed in vivo, e.g., in an animal, such as an animal model for a cardiovascular disorder, e.g., a model of cardiac myocyte hypertrophy or a model for atherosclerosis. By further example, such an animal model can include one for angiogenesis (e.g. tumor induced), or an animal model which encompasses aspects of epidermal wounds (e.g. burns or surgical wounds).

This invention further pertains to novel agents identified by the above-described screening assays. Accordingly, it is within the scope of this invention to further use an agent identified as described herein in an appropriate animal model. For example, an agent identified as described herein (e.g., a bcap73 modulating agent, an antisense bcap73 nucleic acid molecule, a bcap73-specific antibody, or a bcap73-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the bcap73 nucleotide sequences, described herein, can be used to map the location of the bcap73 genes on a chromosome. The mapping of the bcap73 sequences to chromosomes is an important first step in correlating these sequences with genes associated with disease.

Briefly, bcap73 genes can be mapped to chromosomes by preparing PCR primers (preferably 15–25 bp in length) from the bcap73 nucleotide sequences. Computer analysis of the bcap73 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the bcap73 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the bcap73 nucleotide sequences to design oligonucleotide primers, sublocalization can be achieved with panels of fragments from specific chromosomes. Other mapping strategies which can similarly be used to map a bcap73 sequence to its chromosome include in situ hybridization (described in Fan, Y. et al. (1990) *Proc. Natl. Acad. Sci. USA*, 87:6223–27), prescreening with labeled flow-sorted chromosomes, and preselection by hybridization to chromosome specific cDNA libraries Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the bcap73 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The bcap73 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the bcap73 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The bcap73 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequence of SEQ ID NO: 1 can comfortably provide positive individual identification with a panel of perhaps 10 to 1,000 primers which each yield a noncoding amplified sequence of 100 bases. If predicted coding sequences, such as that of SEQ ID NO: 3 are used, a more appropriate number of primers for positive individual identification would be 500–2,000.

If a panel of reagents from bcap73 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial bcap73 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO: 1 are particularly appropriate for this use as greater numbers of polymorphisms occur in the noncoding regions, making it easier to differentiate individuals using this technique. Examples of polynucleotide reagents include the bcap73 nucleotide sequences or portions thereof, e.g., fragments derived from the noncoding regions of SEQ ID NO: 1, having a length of at least 20 bases, preferably at least 30 bases.

The bcap73 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such bcap73 probes can be used to identify tissue by species and/or by organ type.

In a similar fashion, these reagents, e.g., bcap73 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining bcap73 protein and/or nucleic acid expression as well as bcap73 activity, in the context of a biological sample (e.g., blood, serum, cells, tissue) to thereby determine whether an individual is afflicted with a disease or disorder, or is at risk of developing a disorder, associated with aberrant or unwanted bcap73 expression or activity. The invention also provides for prognostic (or predictive) assays for determining whether an individual is at risk of developing a disorder associated with bcap73 protein, nucleic acid expression or activity. For example, mutations in a bcap73 gene can be assayed in a biological sample. Such assays can be used for prognostic or predictive purpose to thereby prophylactically treat an individual prior to the onset of a disorder characterized by or associated with bcap73 protein, nucleic acid expression or activity. In a preferred embodiment, such a disorder includes cardiovascular diseases, disorders, or states involving the cardiovascular system, e.g., the heart, the blood vessels, and/or the blood.

Another aspect of the invention pertains to monitoring the influence of agents (e.g., drugs, compounds) on the expression or activity of bcap73 in clinical trials.

These and other agents are described in further detail in the following sections.

1. Diagnostic Assays

An exemplary method for detecting the presence or absence of bcap73 protein or nucleic acid in a biological sample involves obtaining a biological sample from a test subject and contacting the biological sample with a compound or an agent capable of detecting bcap73 protein or nucleic acid (e.g., mRNA, or genomic DNA) that encodes bcap73 protein such that the presence of bcap73 protein or nucleic acid is detected in the biological sample. A preferred agent for detecting bcap73 mRNA or genomic DNA is a labeled nucleic acid probe capable of hybridizing to bcap73 mRNA or genomic DNA. The nucleic acid probe can be, for example, the bcap73 nucleic acid set forth in SEQ ID NO: 1or 3, or a portion thereof, such as an oligonucleotide of at least 15, 30, 50, 100, 250 or 500 nucleotides in length and sufficient to specifically hybridize under stringent conditions to bcap73 mRNA or genomic DNA. Other suitable probes for use in the diagnostic assays of the invention are described herein.

A preferred agent for detecting bcap73 protein is an antibody capable of binding to bcap73 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect bcap73 mRNA, protein, or genomic DNA in a biological sample in vitro as well as in vivo. For example, in vitro techniques for detection of bcap73 mRNA include Northern hybridizations and in situ hybridizations. In vitro techniques for detection of bcap73 protein include enzyme linked immunosorbent assays (ELISAs), Western blots, immunoprecipitations and immunofluorescence. In vitro techniques for detection of bcap73 genomic DNA include Southern hybridizations. Furthermore, in vivo techniques for detection of bcap73 protein include introducing into a subject a labeled anti-bcap73 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting bcap73 protein, mRNA, or genomic DNA, such that the presence of bcap73 protein, mRNA or genomic DNA is detected in the biological sample, and comparing the presence of bcap73 protein, mRNA or genomic DNA in the control sample with the presence of bcap73 protein, mRNA or genomic DNA in the test sample.

The invention also encompasses kits for detecting the presence of bcap73 in a biological sample. For example, the kit can comprise a labeled compound or agent capable of detecting bcap73 protein or mRNA in a biological sample; means for determining the amount of bcap73 in the sample; and means for comparing the amount of bcap73 in the sample with a standard. The compound or agent can be packaged in a suitable container. The kit can further comprise instructions for using the kit to detect bcap73 protein or nucleic acid.

2. Prognostic Assays

The diagnostic methods described herein can furthermore be utilized to identify subjects having or at risk of developing a disease or disorder associated with aberrant or unwanted bcap73 expression or activity. As used herein, the term "aberrant" includes a bcap73 expression or activity which deviates from the wild type bcap73 expression or activity. Aberrant expression or activity includes increased or decreased expression or activity, as well as expression or activity which does not follow the wild type developmental pattern of expression or the subcellular pattern of expression or wildtype activity which is either insufficient or overabundant for therapeutic effect. For example, aberrant bcap73 expression or activity is intended to include the cases in which a mutation in the bcap73 gene causes the bcap73 gene to be under-expressed or over-expressed and situations in which such mutations result in a non-functional bcap73 protein or a protein which does not function in a wild-type fashion, e.g., a protein which does not interact with a bcap73 substrate, e.g., an actin molecule or an ezrin molecule, or one which interacts with a non-bcap73 substrate, e.g. a non-actin molecule or a non-ezrin molecule. As used herein, the term "unwanted" includes an unwanted phenomenon involved in a biological response such as cellular proliferation. For example, the term unwanted includes a bcap73 expression or activity which is undesirable in a subject.

The assays described herein, such as the preceding diagnostic assays or the following assays, can be utilized to identify a subject having or at risk of developing a disorder associated with a misregulation in bcap73 protein activity or nucleic acid expression, such as a proliferative disorder, a differentiative disorder, a pain disorder, or a cardiovascular disorder. Alternatively, the prognostic assays can be utilized to identify a subject having or at risk for developing a disorder associated with a misregulation in bcap73 protein activity or nucleic acid expression, such as a proliferative disorder. Thus, the present invention provides a method for identifying a disease or disorder associated with aberrant or unwanted bcap73 expression or activity in which a test sample is obtained from a subject and bcap73 protein or nucleic acid (e.g., mRNA or genomic DNA) is detected, wherein the presence of bcap73 protein or nucleic acid is diagnostic for a subject having or at risk of developing a disease or disorder associated with aberrant or unwanted bcap73 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted bcap73 expression or activity. For example, such methods can be used to determine whether a subject can be effectively treated with an agent for a proliferative disorder, a differentiative disorder, or a pain disorder. Thus, the present invention provides methods for determining whether a subject can be effectively treated with an agent for a disorder associated with aberrant or unwanted bcap73 expression or activity in which a test sample is obtained and bcap73 protein or nucleic acid expression or activity is detected (e.g., wherein the abundance of bcap73 protein or nucleic acid expression or activity is diagnostic for a subject that can be administered the agent to treat a disorder associated with aberrant or unwanted bcap73 expression or activity).

The methods of the invention can also be used to detect genetic alterations in a bcap73 gene, thereby determining if a subject with the altered gene is at risk for a disorder characterized by misregulation in bcap73 protein activity or nucleic acid expression, such as a proliferative disorder. In preferred embodiments, the methods include detecting, in a sample of cells from the subject, the presence or absence of a genetic alteration characterized by at least one of an alteration affecting the integrity of a gene encoding a bcap73-protein, or the mis-expression of the bcap73 gene. For example, such genetic alterations can be detected by ascertaining the existence of at least one of 1) a deletion of one or more nucleotides from a bcap73 gene; 2) an addition of one or more nucleotides to a bcap73 gene; 3) a substitution of one or more nucleotides of a bcap73 gene, 4) a chromosomal rearrangement of a bcap73 gene; 5) an alteration in the level of a messenger RNA transcript of a bcap73 gene, 6) aberrant modification of a bcap73 gene, such as of the methylation pattern of the genomic DNA, 7) the presence of a non-wild type splicing pattern of a messenger RNA transcript of a bcap73 gene, 8) a non-wild type level of a bcap73-protein, 9) allelic loss of a bcap73 gene, and 10) inappropriate post-translational modification of a bcap73-protein. As described herein, there are a large number of assays known in the art which can be used for detecting alterations in a bcap73 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the bcap73-gene (see Abravaya et al. (1995) *Nucleic Acids Res*. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a bcap73 gene under conditions such that hybridization and amplification of the bcap73-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a bcap73 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in bcap73 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in bcap73 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the bcap73 gene and detect mutations by comparing the sequence of the sample bcap73 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the bcap73 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type bcap73 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in bcap73 cDNAs obtained from samples of cells. For example, the mutY enzyme of *E. coli* cleaves A at G/A mismatches and the thymidine DNA glycosylase from HeLa cells cleaves T at,G/T mismatches (Hsu et al. (1994) *Carcinogenesis* 15:1657–1662). According to an exemplary embodiment, a probe based on a bcap73 sequence, e.g., a wild-type bcap73 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in bcap73 genes. For example, single strand conformation polymorphism (SSCP) may be used to detect differences in electrophoretic mobility between mutant and wild type nucleic acids (orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control bcap73 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a bcap73 gene.

Furthermore, any cell type or tissue in which bcap73 is expressed may be utilized in the prognostic assays described herein.

3. Monitoring of Effects During Clinical Trials

Monitoring the influence of agents (e.g., drugs) on the expression or activity of a bcap73 protein (e.g., the modulation of cell proliferation and/or migration) can be applied not only in basic drug screening, but also in clinical trials. For example, the effectiveness of an agent determined by a screening assay as described herein to increase bcap73 gene expression, protein levels, or upregulate bcap73 activity, can be monitored in clinical trials of subjects exhibiting decreased bcap73 gene expression, protein levels, or down-regulated bcap73 activity. Alternatively, the effectiveness of an agent determined by a screening assay to decrease bcap73 gene expression, protein levels, or down-regulate bcap73 activity, can be monitored in clinical trials of subjects exhibiting increased bcap73 gene expression, protein levels, or up-regulated bcap73 activity. In such clinical trials, the expression or activity of a bcap73 gene, and preferably, other genes that have been implicated in, for example, a bcap73-associated disorder can be used as a "read out" or markers of the phenotype of a particular cell.

For example, and not by way of limitation, genes, including bcap73, that are modulated in cells by treatment with an agent (e.g., compound, drug or small molecule) which modulates bcap73 activity (e.g., identified in a screening assay as described herein) can be identified. Thus, to study the effect of agents on bcap73-associated disorders (e.g., disorders characterized by deregulated cell proliferation and/or migration), for example, in a clinical trial, cells can be isolated and RNA prepared and analyzed for the levels of expression of bcap73 and other genes implicated in the bcap73-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of bcap73 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a bcap73 protein, mRNA, or genomic DNA in the preadministration sample; (iii) obtaining one or more post-administration samples from the subject; (iv) detecting the level of expression or activity of the bcap73 protein, mRNA, or genomic DNA in the post-administration samples; (v) comparing the level of expression or activity of the bcap73 protein, mRNA, or genomic DNA in the pre-administration sample with the bcap73 protein, mRNA, or genomic DNA in the post administration sample or samples; and (vi) altering the administration of the agent to the subject accordingly. For example, increased administration of the agent may be desirable to increase the expression or activity of bcap73 to higher levels than detected, i.e., to increase the effectiveness of the agent. Alternatively, decreased administration of the agent may be desirable to decrease expression or activity of bcap73 to lower levels than detected, i.e. to decrease the effectiveness of the agent. According to such an embodiment, bcap73 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted bcap73 expression or activity, e.g. a cellular disorder, a cytoskeletal disorder, a motility disorder, or a tissue-repair disorder. In a preferred embodiment, such a disorder includes cardiovascular diseases, disorders, or states involving the cardiovascular system, e.g., the heart, the blood vessels, and/or the blood. In a further preferred embodiment, such a disorder includes diseases, disorders, or states involving angiogenesis (e.g. tumor induced). In another preferred embodiment, such a disorder includes diseases, disorders, or states related to wound (e.g. epidermal wounds, burns, or surgical wounds). With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the βCAP73 molecules of the present invention or βCAP73 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted βCAP73 expression or activity, by administering to the subject a βCAP73 or an agent which modulates βCAP73 expression or at least one βCAP73 activity. Subjects at risk for a disease which is caused or contributed to by aberrant or unwanted βCAP73 expression or activity can be identified by, for example, any or a combination of diagnostic or prognostic assays as described herein. Administration of a prophylactic agent can occur prior to the manifestation of symptoms characteristic of the βCAP73 aberrance, such that a disease or disorder is prevented or, alternatively, delayed in its progression. Depending on the type of βCAP73 aberrance, for example, a βCAP73, βCAP73 agonist or βCAP73 antagonist agent can be used for treating the subject. The appropriate agent can be determined based on screening assays described herein.

2. Therapeutic Methods

Another aspect of the invention pertains to methods of modulating βCAP73 expression or activity for therapeutic purposes. Accordingly, in an exemplary embodiment, the modulatory method of the invention involves contacting a cell with a βCAP73 or agent that modulates one or more of the activities of βCAP73 protein activity associated with the cell. An agent that modulates βCAP73 protein activity can be an agent as described herein, such as a nucleic acid or a protein, a naturally-occurring target molecule of a βCAP73 protein (e.g., a βCAP73 substrate), a βCAP73 antibody, a βCAP73 agonist or antagonist, a peptidomimetic of a bcap73 agonist or antagonist, or other small molecule. In one embodiment, the agent stimulates one or more βCAP73 activities. Examples of such stimulatory agents include active βCAP73 protein and a nucleic acid molecule encoding βCAP73 that has been introduced into the cell. In another embodiment, the agent inhibits one or more βCAP73 activities. Examples of such inhibitory agents include antisense bcap73 nucleic acid molecules, anti-βCAP73 antibodies, and βCAP73 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a βCAP73 protein or nucleic acid molecule. In one embodiment, the method involves administering an agent (e.g., an agent identified by a screening assay described herein), or combination of agents that modulates (e.g., upregulates or downregulates) βCAP73 expression or activity. In another embodiment, the method involves administering a βCAP73 protein or nucleic acid molecule as therapy to compensate for reduced, aberrant, or unwanted βCAP73 expression or activity. Stimulation of βCAP73 activity is desirable in situations in which βCAP73 is abnormally down-regulated and/or in which increased βCAP73 activity is likely to have a beneficial effect. Likewise, inhibition of βCAP73 activity is desirable in situations in which βCAP73 is abnormally up-regulated and/or in which decreased βCAP73 activity is likely to have a beneficial effect.

3. Pharmacogenomics

The βCAP73 molecules of the present invention, as well as agents, or modulators which have a stimulatory or inhibitory effect on βCAP73 activity (e.g., βCAP73 gene expression) as identified by a screening assay described herein can be administered to individuals to treat (prophylactically or therapeutically) βCAP73-associated disorders (e.g., proliferative disorders) associated with aberrant or unwanted βCAP73 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a bcap73 molecule or βCAP73 modulator as well as tailoring the dosage and/or therapeutic regimen of treatment with a βCAP73 molecule or βCAP73 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a bcap73 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a βCAP73 molecule or βCAP73 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a bcap73 molecule or βCAP73 modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification and Characterization of bcap73 cDNAs

Figure 2:
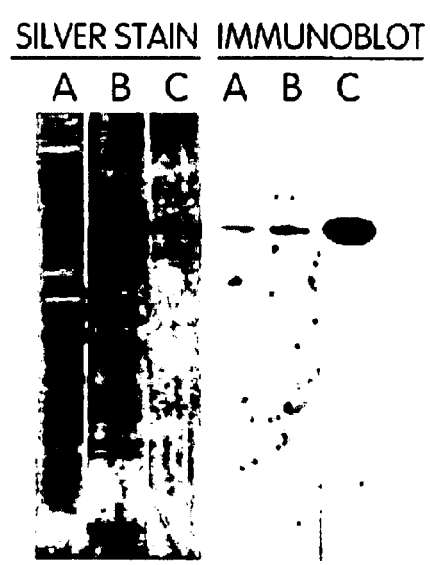
FIG. 2: Results of two-step purification of bcap73 from bovine retinal pericytes or bovine platelets using ion-exchange chromatography. A Triton X-100 lysate (A) is enriched for bcap73 with SP-sepharose (B) followed by DEAE-sepharose (C). An decrease in contaminating proteins can be seen in the silver stained SDS-PAGE, as well as a concomitant enrichment of bcap73 which is shown in the immunoblot.
Figure 3A:
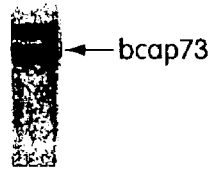
FIG. 3: (A) A northern blot shows the 4.7 kb mRNA of bcap73 in endothelial cells. (B) A schematic representation of the cDNA of bovine bcap73 which shows the portion of the cDNA that was originally identified from a bovine endothelial cell library, and the region that was reconstructed using 5' RACE (rapid amplification of cDNA ends). (C) Recombinant βCAP73 expression constructs are also indicated. (D) Schematic representation of βCAP73 protein domains from deduced amino acid sequence. The ankyrin-like repeats were identified by sequence domain search, while the 100 amino acid α-helical domain was identified through secondary structure prediction. The epitope-containing region was determined by immunoblotting of the GST-fusion constructs indicated in A, where proteins generated from the βCAP73-F and βCAP73-N constructs were immunoreactive with the anti-βCAP73 mAb while βCAP73-C was not.
Figure 3B:
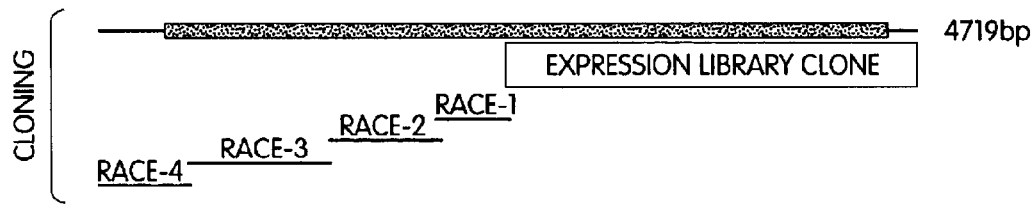
Figure 3C:
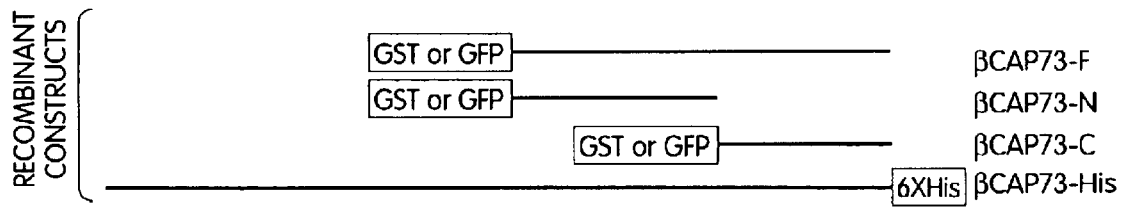
Figure 3D:

Purification of bcap73 Protein from Bovine Retinal Pericytes or Bovine Platelets A Triton X-100 soluble lysate from bovine retinal pericytes or bovine platelets can be enriched for βCAP 73 protein by using ion-exchange purification. The lysate is first applied to SP-sepharose under ionic strength conditions for βCAP 73 to bind to the resin. After washing contaminating proteins away, a fraction containing βCAP 73 protein can be eluted between 185 and 230 mM NaCl (see FIG. 2, lane B). A second ion-exchange chromatography with DEAE-sepharose is able to purify the protein further. After loading and washing steps analogous to those outlined above, the βCAP 73 protein is able to be eluted between 70 and 80 mM NaCl. A βCAP 73 protein obtained in this manner can be greater than 90% pure (see FIG. 2, lane C).

Isolation and Cloning of the Bovine βCAP 73 cDNA

The invention is based, at least in part, on the discovery of a bovine gene encoding a novel protein, referred to herein as βCAP 73. Total RNA was harvested from bovine endothelial cells (ECs) that were crawling in response to mechanical injury and purified as previously described (Hoock et al. 1991). 5 µg of polyA+ RNA isolated using PolyA Tract (Promega) served as template for expression library construction using the λ ZAPII library kit from Stratagene, following manufacturer protocols. Average insert size was 1.4 kb (+/−0.5), with a range of 600 bp to 2.5 kb, as assessed by mass excision of the library and analysis of 10 randomly chosen colonies. The number of individual clones in the library was greater than $1 \times 10^6$.

To identify the βCAP73 cDNA, $2.1 \times 10^5$ plaques were plated on 150 mm NZY plates at a density of $2.3 \times 10^4$ plaques/plate. Replica nitrocellulose filters were washed with 25 mL per filter of TBS-Tween (TBST, 20 mM Tris, pH. 7.5, 0.9% NaCl, 0.05% Tween-20) prior to blocking with 5% milk in TBST. Washed and blocked filters were probed with anti-βCAP73 mAb as follows. Concentrated hybridoma cultured supernatant containing 30 µg/mL anti-βCAP73 IgM was pre-incubated with 0.25 mg/mL XL1-Blue bacterial lysate for 1 h at RT, rocking. The blocked anti-βCAP73 IgM was then diluted 1:3 with TBST and 5% milk TBST to reach a final concentration of 10 µg/mL antibody and 2.5% milk. The filters were incubated overnight at 4° C., rocking. After extensive washing, the filters were incubated with HRP-labeled secondary antibody for 1 h at RT, washed again, and 27 positive plaques were identified. The positives were collected into two pools and rescreened. After the second round of screening, one positive plaque remained that was plaque pure after re-plating and re-probing with the anti-βCAP73 mAb. The βCAP73 cDNA-containing plasmid was excised out of the λ arms using ExAssist helper bacteriophage (Stratagene) and sequenced. The novel clone contained a 2.5 kb open reading frame that extended to the 5' end of the clone. To obtain the remainder of the βCAP73 cDNA, 5' RACE (rapid amplification of cDNA ends) was implemented.

5' RACE

5' RACE reagents were obtained from Gibco-BRL, and procedures were performed as described by the manufacturer with one modification: the reverse transcription (rev) reaction was carried out for 30 min at 50° C. instead of 42° C. βCAP73 gene-specific, anti-sense primer pairs that were used in the reactions are as follows: RACE-1, rev: 5' GCTCTAATCTGCTCTTGAGC (SEQ ID NO:5), PCR: 5' CTAGTCGACTGTTCCTCTGGTTTGACGTG (SEQ ID NO:6); RACE-2, rev: TCAGCCTGTGGTTCCCAGTGG (SEQ ID NO:7), PCR: TGTCAGGTGCTCTTTCAAGGC (SEQ ID NO:8); RACE-3, rev: 5' GTAGCTGTAAACCAT-TGACT (SEQ ID NO:9), PCR: 5' ATATTCTCTGTTCT-TGCTGA (SEQ ID NO:10); RACE-4, rev: 5' CTAGCT-TGCCTGGATTGACTC (SEQ ID NO:11), PCR: 5' TTTAGCAAGGATTGAGGACAC (SEQ ID NO:12). The 5' RACE products were purified and concentrated using Qiaquick columns (Qiagen) and ligated into pGEM-TEasy vectors (Promega). New sequences from each round of 5' RACE were compared using MacDNAsis software to resolve any PCR-generated errors. At least 6 individual clones for each round of 5' RACE were analyzed and sequenced. Each round of 5' RACE yielded 400–800 bp of new cDNA.

The sequence of the entire clone was determined to be 4736 nucleotides in length. This sequence is SEQ IN NO:1 and is shown in FIGS. 4-1 through 4-8. An open reading frame (ORF) was identified from nucleotides 392 to 4597, which codes for a deduced amino acid sequence of 1401 residues. The full cDNA with its corresponding ORF amino acid sequence is shown in FIGS. 4-1 through 4-8.

Analysis of the Bovine βCAP73 Molecules

A BLAST search (Altschul et al. (1990) *J. Mol. Biol.* 215:403) of the nucleotide sequence of bovine βCAP 73 has revealed that separate internal regions of the βCAP 73 cDNA are significantly similar to *C. familiaris* mRNA sequence for C3VS (GenBank Accession No. X99145), a Tentative Human Consensus (THC) Contiguous Sequence from the TIGR (Accession Nos. THC244788, THC186491, THC186491, THC213238), and the human KIAA1561 protein (Accession No. AB046781).

Tissue Distribution of βCAP 73 mRNA

This example describes the tissue distribution of βCAP 73 transporter mRNA, as can be determined by Northern blot hybridization and in situ hybridization.

Figure 5:
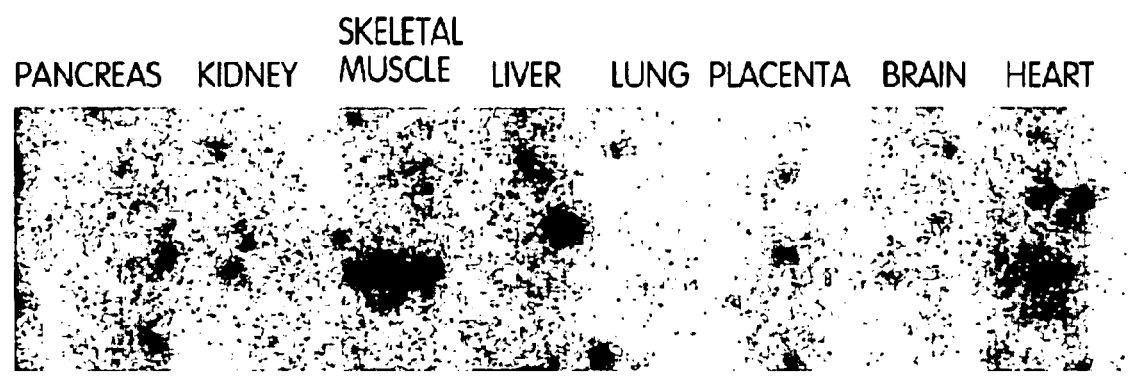

Northern blot hybridizations with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations. FIG. 5 shows the results of such an analysis, with βCAP73 mRNA detected predominantly in skeletal muscle as well as brain and heart.

To detect βCAP73 mRNA, 1 ug of polyA EC RNA from was separated in a 1.2% agarose-formaldehyde bed gel, transferred to nylon membrane (Schleicher and Scheull) by capillary transfer and UV crosslinked to the membrane. The blot was incubated in pre-hybridization solution (50% formamide, 5×SSPE, 5×Denhardt's, 1% SDS, 10% dextran sulfate, 100 µg/mL polyA and 100 µg/mL salmon sperm DNA) for at least 3 h at 42° C. Nick-translated, [$^{32}$P]-labeled probe was made from plasmid containing the library clone (nt 2303–4719 of the βCAP73 cDNA; [α-$^{32}$P] dCTP from ICN, DNase I and DNA polymerase I from Gibco-BRL). The probe was mixed with 1×10$^6$ cpm/mL into the pre-hybridization solution and incubated with the blot for 16 h at 42° C. The blot was washed first in 1×SSC (150 mM NaCl, 15 mM sodium citrate, pH 7.0), 0.1% SDS for 15 min at room temperature (RT), followed by a second wash in 0.25×SSC, 0.1% SDS for 15 min at RT. The blots were exposed to autoradiographic film (Kodak) at −80° C. for 24 h prior to development.

For in situ analysis, various tissue samples are obtained from brain, skeletal muscle, cardiovascular tissue, or other tissues and are first frozen on dry ice. Ten-micrometer-thick coronal sections of the tissues are postfixed with 4% formaldehyde in DEPC treated 1×phosphate-buffered saline at room temperature for 10 minutes before being rinsed twice in DEPC 1×phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled (5×10$^7$ cpm/mL) cRNA-probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 µg of RNase A per mL for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

To explore the relative abundance and tissue distribution of βCAP73, Northern analysis was performed. A probe was made to nt 3502–4719, a region of βCAP73 that is highly homologous to human KIAA1561 (Accession No. AB046781). Hybridization of human tissues with radiolabeled probe revealed expression of an approximately 5 kb transcript in all tissues tested. Stripping and re-probing of the blot with β-actin probe allowed the normalization of βCAP73 expression. The strongest expression occurred in skeletal muscle followed by heart, with relative expression levels of 6.3 (arbitrary units) and 1.7, respectively. Relative expression in the other tissues tested ranged from 0.63 in kidney to 0.083 in lung. Lack of expression in brain was due to the very low amount of mRNA analyzed, evidenced by the low β-actin signal.

Example 2

Recombinant Expression of βCAP 73 in Bacterial Cells

In this example, βCAP 73 was expressed as a recombinant glutathione-S-transferase (GST) fusion polypeptide in *E. coli* and the fusion polypeptide was isolated and characterized.

GST-βCAP73 Domains

Bacterial glutathione-S-transferase (GST) fusion constructs were made in the pGEX-3X vector, which contains a Factor Xa site to cleave the GST moiety from the recombinant βCAP73 domains (Pharmacia). Inserts encoding for βCAP73-F and βCAP73-C (see FIG. 2A) were made by PCR using sequence specific primers that generated restriction endonuclease sites for in-frame ligation into pGEX-3X. The βCAP73 library clone was used as the target for the PCR reactions. The primer pairs used are as follows: βCAP73-F forward) 5' CGGGATCCCCGTGGAAA-GAGAATATGAAAGATCA (SEQ ID NO:13), βCAP73-F reverse) 5' CGGGATCCCGGCACACGAGCCCCTGCCG (SEQ ID NO:14); βCAP73-C forward) 5' CGGGATC-CCCAATTCTTATGAAACAGAAAGAGCA (SEQ ID NO:15), βCAP73-C reverse) 5' CGGGATCCCGGCACAC-GAGCCCCTGCCG (SEQ ID NO:16). The βCAP73-N construct was generated by digestion of the library clone in pBluescript with EcoRI to release the βCAP73-N fragment. The fragment was then ligated in-frame into the pGEX-3X expression vector. All constructs were re-sequenced to assure that no mutations were generated during PCR amplification.

Expression and Purification of GST-βCAP73 Domains

Bacterial expression was performed basically according to the manufacturer's protocol, except that expression was induced with 0.1 mM IPTG for 2 h at 28° C. instead of 37° C. After induction, the cells were pelleted and stored at −80° C.

The βCAP73 domains were purified according to manufacturer protocols (Pharmacia). Purified GST-βCAP73 fusion products bound to glutathione-Sepharose were exchanged into Factor Xa cleavage buffer (50 mM Tris, pH 7.5, 150 mM NaCl, and 1 mM CaCl$_2$) and treated with Factor Xa at a final concentration of 0.25 U/mL of matrix for 2 h at RT, rotating. βCAP73 domains relieved of the GST moiety were then collected as flowthrough. Almost 90% of the βCAP73 domains were recovered compared to the total GST-βCAP73 that was purified. Typical yield for GST-βCAP73-F and GST-βCAP73-N fusion proteins was 0.5 mg from 100 mL of culture. The GST-βCAP73-C construct typically yielded <0.5 μg protein from 100 mL of starting culture.

Example 3

Recombinant bCAP73 Expression

Full-length βCAP73-His

The full-length βCAP73-His mammalian expression plasmid was created as follows. First, the 5' RACE fragments and the library fragment were ligated together by PCR-mediated ligation. Forward primers were made to the 5' ends of all the fragments of the βCAP73 clone. The forward primer made to the RACE-4 fragment also contained a KpnI site, underlined in the sequence. The primer sequences are RACE-1) 5' GAACTGGCTCACAAGGTGGC (SEQ ID NO:17), RACE-2) 5' GGTGACAATCTGGACATTCTAA (SEQ ID NO: 18), RACE-3) 5' TCCTGTCTATGATGAGCTGTTG (SEQ ID NO:19), RACE-4) 5' GG GGTACCAGTGTTGAGGCGGCAGGAT (SEQ ID NO:20). The following reverse primer was made for the 3' most fragment (original library fragment) that contained bases encoding for six histidines (in parentheses), a termination codon (in bold), and XbaI site (underlined) for ligation into pcDNA3 (Invitrogen): 5' GCTCTAGACTA (GTGATGGTGATGGTGATG)GCACACGAGCCCCTG CCG (SEQ ID NO:21). The reverse primers against the RACE fragments were the same as the PCR primers used to generate the RACE clones. βCAP73 clone fragments were ligated by putting the following into a PCR reaction: 1.5× 10$^{-14}$ moles each of the gel purified library fragment and RACE1 fragment, forward primer to the RACE-1 fragment and reverse primer for the library fragment, 0.2 mM dNTPs, 1.5 mM MgCl$_2$, 0.25 U/μl Tli DNA polymerase (Promega), and I×Tli polymerase buffer. PCR cycles were as follows: 5 cycles of denaturation at 95° C., 1 min, annealing and extension at 72° C. for 5 min, 20 cycles of denaturation at 95° C., 1 min, annealing at 55° C. for 30 s, and extension at 72° C. for 5 min. RACE fragments 2 and 3 were ligated using the RACE-3 forward primer and the RACE-2 PCR reverse primer in the same DNA ligation/amplification reaction as just described. The RACE 2/3 fragment was then ligated to the RACE4 fragment in the same manner, except the primers used in the reaction were the RACE4 forward and the RACE-2 PCR reverse. Finally the RACE2/3/4 fragment was ligated to the RACE1/library fragment to generate the final 4.7 kb insert by using the RACE-4 forward primer and the library fragment reverse primer in DNA ligation/amplification. The βCAP73-His insert was then digested with KpnI and XbaI restriction endonucleases and ligated into the pcDNA3 vector. The construct was then re-sequenced to assess whether PCR amplification had generated mutations.

GFP-βCAP73 Domains

Green fluorescent protein (GFP)-βCAP73 domain constructs were made in the same manner as the GST-βCAP73 domain constructs (see above), except that different primers were used in order to generate the 5' EcoRI and 3' BamHI restriction endonuclease sites (underlined) for in-frame ligation into pEGFP-C1 (Clontech). The following primer sets were used: GFP-βCAP73-N) forward, 5' G GAATTCAGTGGAAAGAGAATATGAAAGA (SEQ ID NO:22), reverse, 5' GCGGATCCTCAATGTGAACATTC (SEQ ID NO:23); GFP-βCAP73-C) forward, 5' CAT-TGAGAATTCTTATGAAACAG (SEQ ID NO:24), reverse, 5' CGGGATCCAATTCTTATGAAACAGAAAGAG (SEQ ID NO:25). All constructs were re-sequenced to check for potential PCR-generated mutations.

Overexpression and Cellular Localization of Full-length βCAP73-His and GFP-βCAP73 in Pericytes For transient overexpression, pericytes (PCs) were plated onto 8-well chamber slides (Beckton Dickinson) at 40% confluency and grown overnight at 37° C. 1 μg of DNA (GFP-βCAP73-N, GFP-βCAP73-C, βCAP73-His, or vector controls) was transfected into each well using Effectene transfection reagent (Qiagen, Santa Clarita, Calif.), and the cells were incubated for 48 h at 37° C. The GFP-βCAP73 domains were visualized live on a Zeiss IM-35 fluorescence microscope using a 40×, water-immersion objective lens (NA 0.75; Zeiss). βCAP73-His transfectants were identified after fixation and permeabilization. The cells were fixed for 5 min at RT with 4% formaldehyde made in 1×DME, prior to three washes with PBS, 5 min per wash. After fixation and washing, the cells were permeabilized with a 0.1% Triton X-100 buffer (50 mM Hepes, pH 6.9,40 mM Pipes, pH 7.2, 75 mM KCl, 0.1 mM EGTA, 1 mM MgCl$_2$, 0.1% Triton-X 100) for 90 s at RT, followed by three PBS washes, 5 min per wash. After blocking the cells with 2.5 mg/mL BSA for 1 h at RT, the cells were probed with a 1:500 dilution of INDIA probe nickel detection (Pierce, Rockford, Ill.), followed by incubation with 1 μg/mL rabbit anti-HRP antibody (Polysciences, Inc., Warrington, Pa.) and then 1 μg/mL FITC-labeled, anti-rabbit antibody. The cells were visualized on a Zeiss IM-35 fluorescence microscope equipped with a 63× planapochromat oil immersion objective lens (Zeiss).

Example 4

Expression of Recombinant bcap73 Protein in COS cells

To express the βCAP 73 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire βCAP 73 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the βCAP 73 DNA sequence is amplified by PCR using two primers. The 55 primer contains the restriction site of interest followed by approximately twenty nucleotides of the βCAP 73 coding sequence starting from the initiation codon; the 3' end sequence contains complementary sequences to the other restriction site of interest, a translation stop codon, the HA tag or FLAG tag and the last 20 nucleotides of the βCAP 73 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the βCAP 73 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the βCAP 73-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the βCAP 73 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the βCAP73 coding sequence is cloned directly into the polylinker of the pcDNA/Amp vector using the appropriate restriction sites. The resulting plasmid is transfected into COS cells in the manner described above, and the expression of the βCAP73 polypeptide is detected by radiolabelling and immunoprecipitation using a βCAP73 specific monoclonal antibody.

Example 5

Expression of βCAP73 Protein in Calpastatin-overexpressing Cells

Calpastatin-overexpressing cell lines were obtained from Dr. David Potter (Potter et al. 1998). To make lysates, cells from a confluent, 100 mm dish were rinsed three times with PBS at RT, scraped in 10 mL of PBS and transferred to a tube on ice. The cells were pelleted by centrifugation at 250×g for 5 min at 4° C. After removing the supernatant, the cell pellet was resuspended in 0.5 mL of ice cold PBS plus protease inhibitors as previously described (Shuster et al., 1996), prior to lysis by sonication on ice. The lysates were clarified by centrifugation at 20,000-×g for 20 min at 4° C., separated by SDS-PAGE, and transferred to nitrocellulose membrane. βCAP73 was detected using anti-βCAP73 mAb.

Example 6

βCAP73 Expression in Cells Stimulated to Crawl

When a confluent monolayer of ECs are disrupted by mechanical injury, cells crawl into the denuded zones in order to repopulate the wound space (Hoock et al., 1991). We wanted to observe changes in the mRNA expression of βCAP73, since a regulator of actin assembly state would likely be expressed at different levels depending on the motile state of the cells. PolyA RNA isolated from populations of cells crawling for 30, 60, and 90 min following injury were compared to confluent, stationary cells. Northern blotting revealed that βCAP73 mRNA was, indeed, heavily regulated during the motile response to injury. While βCAP73 mRNA was high in confluent cells, it was just detectable at 30 min post-injury and gradually increased as the cells continued to crawl and infiltrate the wound space. The relative expression levels compared to confluent were 0.13 at 30 min, 0.25 at 60 min, and 0.38 at 90 min, where confluent=1.

Example 7

βCAP73 Expression in Cells with Spreading Defects

Recently, a model system was developed to study the role of calpain in cell motility (Potter et al., 1998). 3T3 cells were made to stably overexpress calpastatin, the naturally occurring inhibitor of calpain. These cells are smaller than their parent cells, produced fewer lamellae, and do not spread well. Importantly, these calpain-inhibited cells accumulate ezrin, a cellular calpain substrate (Yao et al., 1993), and it appears that lack of ezrin cleavage is a primary cause of the spreading defects (Potter et al., 1998; Shuster and Herman, 1995). Because ezrin, like βCAP73, associates with the barbed ends of β-actin filaments where it may also play a role in controlling actin dynamics, we asked whether βCAP73 protein levels were coordinately increased in these mutant cells. Immunoblotting showed that, like ezrin, βCAP73 was also up regulated in these motility-defective cells. βCAP73 was barely detectable in the parental 3T3 cells, which spread and migrate rapidly over fibronectin-coated growth substrate. But in the calpastatin overexpressing cells, βCAP73 levels were induced 10-fold. This increase in βCAP73 steady state protein level was not a part of general protein increase, since many cytoskeletal proteins did not change expression or did so minimally (Potter et al., 1998). Of the ERM family members, only ezrin is significantly induced, increasing 7-fold over parental levels (compared to 2-fold radixin and moesin; no change in talin).

Example 8

Overexpression of βCAP73 and βCAP73 Domains

Because changes in actin dynamics directly affects cell shape, it was hypothesized that overexpression of a regulator of β-actin dynamics, such as βCAP73, would alter spreading, motility, and morphology. Furthermore, due to the β-isoactin capping specificity of βCAP73, it was predicted that overexpression would primarily affect cortical membrane structures. Bovine retinal PCs overexpressing βCAP73-His were assessed for alterations in cell morphology and localization of the recombinant protein 48 h after the start of transfection. In comparison to surrounding non-transfected cells, the βCAP73-His overexpressing cells were generally rounder and smaller. Using a probe against the histidine tag, the βCAP73-His fusion proteins were observed within novel surface protrusions that appeared to be apical plasma membrane-associated. Similarly, overexpression of βCAP73 domains changed cell shape. Transient overexpression of GFP-βCAP73-N and GFP-βCAP73-C in PCs caused the cells to diminish in overall size, but maintain arborized processes. GFP control cells and surrounding untransfected cells remained flat and well spread, as observed by phase microscopy. In contrast to the condensed, membrane localization of the βCAP73-His, the GFP-βCAP73-N and the GFP-βCAP73-C domains were not localized to a precise area within the cells, but remained diffuse.

Example 9

Effects of βCAP73 on β-Actin Expression
Purification of Actin Isoforms

Skeletal muscle β-actin was purified from chicken muscle acetone powder, prepared as previously described (Herman and Pollard, 1979; Spudich and Watt, 1971). Red blood cell (RBC) β-actin was purified from RBC acetone powder prepared as previously described (Puszkin et al., 1978; Shuster and Herman, 1995) with some modifications. Briefly, acetone powder made from bovine RBCs was extracted twice in 15 mL G buffer per g of acetone powder, the first extraction for 5 h on ice at 4° C. and the second extraction for 16 h on ice at 4° C. The extracts were then pooled and concentrated to one-tenth the starting volume before polymerization in 2 mM MgCl$_2$ and 100 mM KCl for 1 h at room temperature (RT). Following polymerization, the actin solution was brought up to 800 mM KCl and incubated at 1 h RT. The polymerized actin was pelleted by centrifugation at 100,000-xg for 2 h at 4° C., de-polymerized by dialysis in G buffer, and then chromatographed on Sephadex G-150 (Sigma). Fractions were analyzed for purity by SDS-PAGE followed by staining with Coomassie Blue.
Pyrene Labeling of Actin Isoforms Isoactins were pyrene labeled based on the method of Kouyama and Mihashi (1981). Pyrene-iodoacetamide (Molecular Probes) was added to the labeling reaction at a molar ratio of 1:1.125 (actin:pyrene) in the following order and final concentrations: 40 μM isoactin, 2 mM MgCl$_2$, 45 μM pyrene-iodoacetamide, 100 mM KCl. The reaction was polymerized/labeled for 1.5 h at RT in the dark. After centrifugation at 100,000-xg for 2 h at 10° C., pelleted pyrene-actin was depolymerized by dialysis in G buffer at 4° C., then clarified at 100,000-xg for 30 minutes (min) at 4° C. before being frozen as aliquots in liquid nitrogen and stored at −80° C.
Barbed-end Capping Assays The assays were performed as previously described (Weber et al., 1987) with modifications. 1 μM (50% pyrene labeled) β- or α-actin in G buffer was seeded with 0.05–0.1 nM sheared F-actin seeds (isoactins polymerized at 30 μM were sheared once through a 50 μL Hamilton syringe just prior to addition to the reaction). The capping assays were performed as follows. The 1 μM isoactin solution was pre-incubated with 0.2 mM MgCl$_2$ for 3 min at 25° C. to allow for Ca$^{2+}$/Mg$^{2+}$ exchange. At time=0, isoactin seeds, various amounts of βCAP73; 2 mM MgCl$_2$, and 100 mM KCl were added in rapid succession, mixed, and placed in a 0.5 cm$^2$ fluorimetry cuvette. Fluorescence intensity was detected on a Perkin-Elmer Luminescence Spectrometer LS 50B (excitation=365 nM, emission=407 nM). The polymerization reactions were carried out at 25° C. in 300 μl reaction volumes.
Effects of βCAP73 on β-actin Polymerization In Vitro In order to understand βCAP73 effects on the polymerization of β- and α-actins, GST-βCAP73 constructs were generated for bacterial expression.

The recombinant βCAP73 domains were tested for isoactin-specific capping of barbed-end in kinetic assays. To confine assembly to the barbed end, polymerization assays were carried out at 1 μM actin. β-Actin polymerization at the barbed end was indeed inhibited by βCAP73. 1 μM βCAP73-F inhibited β-actin assembly by 44% (FIG. 5). Addition of 1 μM βCAP73-C to β-actin was slightly inhibitory (26% inhibition), while βCAP73-N had minimal effect (5% inhibition). In contrast, none of the βCAP73 domains altered β-actin polymerization. Using 1 nM CapZ or gelsolin as controls for barbed-end inhibition, it was shown that both α- and β-actin assemblies were blocked indiscriminately.
Equivalents Those skilled in the art will recognize, or be able to ascertain using no more than many equivalents to the specific embodiments of the invention equivalents are intended to be encompassed by the following claims.

What is claimed:

1. An isolated nucleic acid molecule comprising the nucleotide sequence set forth in SEQ ID NO: 1.

2. An isolated nucleic acid molecule which encodes a polypeptide comprising the amino acid sequence set forth in SEQ ID NO: 2.

3. An isolated nucleic acid molecule comprising the nucleotide sequence set forth in SEQ ID NO: 3.

* * * * *

SEQUENCE LISTING

```
<160> NUMBER OF SEQ ID NOS: 25

<210> SEQ ID NO 1
<211> LENGTH: 4730
<212> TYPE: DNA
<213> ORGANISM: Bos taurus
<220> FEATURE:
<221> NAME/KEY: CDS
<222> LOCATION: (392)...(4597)

<400> SEQUENCE: 1
cagtgttgag gcggcaggat gtagagtgct gttcaagctt tccagtggag tccccgaaaa        60
gggaaggcag agaaagacat cttctaaata acaaatagga ggagttacag tacctgactt       120
ggggctgctc ttaatcaagt gctgccgctg caaggaagat aattttcaag cgttatgaag       180
gcggagaagg attccgaaga cgaagaaaat atccttagag atccaagcta agtgtagtgc       240
agcatgaaga ttgcagaaca ggaagagttc taagaagaag gactgagtca ctagttagga       300
gtctctctga gggctggctt tgtgagccac agtgatttgt aacttaatgc gaactaattt       360
```

-continued

```
gctgttagca acaagaaact aaatcctgtc t atg atg agc tgt tgg ttt tct      412
                                  Met Met Ser Cys Trp Phe Ser
                                   1               5 tgt gct cct aag aac aga caa gca gca gat tgg aac aaa tac gat gac    460
Cys Ala Pro Lys Asn Arg Gln Ala Ala Asp Trp Asn Lys Tyr Asp Asp
         10                  15                  20 cga ttg atg aga gca gca gaa agg gga gat gta gaa aaa gtg tcc tca    508
Arg Leu Met Arg Ala Ala Glu Arg Gly Asp Val Glu Lys Val Ser Ser
     25                  30                  35 atc ctt gct aaa aag gga gtc aat cca ggc aag cta gat gta gaa ggc    556
Ile Leu Ala Lys Lys Gly Val Asn Pro Gly Lys Leu Asp Val Glu Gly
 40                  45                  50                  55 aga tct gcc ttt cat gtt gtg gcc tca aag gga aat ctt gag tgt ttg    604
Arg Ser Ala Phe His Val Val Ala Ser Lys Gly Asn Leu Glu Cys Leu
                 60                  65                  70 aat gcc atc ctc ata cat gga gtt gat att aca acc agt gac acc gca    652
Asn Ala Ile Leu Ile His Gly Val Asp Ile Thr Thr Ser Asp Thr Ala
             75                  80                  85 gga agg aat gct ctt cac ctg gct gca aag tat ggg cat gca ctg tgt    700
Gly Arg Asn Ala Leu His Leu Ala Ala Lys Tyr Gly His Ala Leu Cys
         90                  95                 100 cta caa aaa ctt cta cag tac aat tgt ccc act gaa cat gta gac ctg    748
Leu Gln Lys Leu Leu Gln Tyr Asn Cys Pro Thr Glu His Val Asp Leu
    105                 110                 115 cag gga aga act gca ctt cat gat gca gct atg gca gac tgt cct tct    796
Gln Gly Arg Thr Ala Leu His Asp Ala Ala Met Ala Asp Cys Pro Ser
120                 125                 130                 135 agc ata cag ctg ctc tgc gac cat ggg gcc tcg gtg aat gcc aaa gat    844
Ser Ile Gln Leu Leu Cys Asp His Gly Ala Ser Val Asn Ala Lys Asp
                140                 145                 150 gta gat ggg cgg aca cca ctt gtt ctg gct acc cag atg tgt agg cca    892
Val Asp Gly Arg Thr Pro Leu Val Leu Ala Thr Gln Met Cys Arg Pro
            155                 160                 165 aca ata tgt caa ctg ctg ata gat aga ggg gcg gat att aat tcc aga    940
Thr Ile Cys Gln Leu Leu Ile Asp Arg Gly Ala Asp Ile Asn Ser Arg
        170                 175                 180 gac aaa caa aac agg act gct ctc atg cta gga tgc gag tat ggt tgc    988
Asp Lys Gln Asn Arg Thr Ala Leu Met Leu Gly Cys Glu Tyr Gly Cys
    185                 190                 195 aaa gat gca gta gaa gtc tta atc aaa aac ggc gct gac gtg acc ttg   1036
Lys Asp Ala Val Glu Val Leu Ile Lys Asn Gly Ala Asp Val Thr Leu
200                 205                 210                 215 ctg gac gcc ctt ggc cat gac agt tct tac tat gca aga att ggt gac   1084
Leu Asp Ala Leu Gly His Asp Ser Ser Tyr Tyr Ala Arg Ile Gly Asp
                220                 225                 230 aat ctg gac att cta acc tta ctg aag act gca tca gaa aat tcc aac   1132
Asn Leu Asp Ile Leu Thr Leu Leu Lys Thr Ala Ser Glu Asn Ser Asn
            235                 240                 245 aaa ggg aga gaa ctt tgg aag aaa gga cca tct tta caa cag cga aat   1180
Lys Gly Arg Glu Leu Trp Lys Lys Gly Pro Ser Leu Gln Gln Arg Asn
        250                 255                 260 ttg tct cag atg cta gat gaa gta aat acg aag tca aat cag agg gag   1228
Leu Ser Gln Met Leu Asp Glu Val Asn Thr Lys Ser Asn Gln Arg Glu
    265                 270                 275 cat caa aac att cag gat ctg gag att gaa aat gaa gat ctg aaa gag   1276
His Gln Asn Ile Gln Asp Leu Glu Ile Glu Asn Glu Asp Leu Lys Glu
280                 285                 290                 295 aga ttg aga aaa att cag caa gaa cag aga ata tta ttg gat aaa gtc   1324
Arg Leu Arg Lys Ile Gln Gln Glu Gln Arg Ile Leu Leu Asp Lys Val
                300                 305                 310
```

```
aat ggt tta cag cta cag ctg aat gag gaa gta atg gtg gct gat gat    1372
Asn Gly Leu Gln Leu Gln Leu Asn Glu Glu Val Met Val Ala Asp Asp
            315                 320                 325 ctg gaa agt gag aaa gaa aag ctg aag tcc ctt ttg gca gcc aaa gaa    1420
Leu Glu Ser Glu Lys Glu Lys Leu Lys Ser Leu Leu Ala Ala Lys Glu
        330                 335                 340 aag cag cat gaa gaa agc cta aga act att gag gct ctg aaa agt aga    1468
Lys Gln His Glu Glu Ser Leu Arg Thr Ile Glu Ala Leu Lys Ser Arg
    345                 350                 355 ttt aag tat ttt gag agt gat cat tta gga tca gga agt cat ttc agg    1516
Phe Lys Tyr Phe Glu Ser Asp His Leu Gly Ser Gly Ser His Phe Arg
360                 365                 370                 375 aaa gaa gat atg ctt ctt aaa caa ggt caa atg tac atg aca gac tca    1564
Lys Glu Asp Met Leu Leu Lys Gln Gly Gln Met Tyr Met Thr Asp Ser
            380                 385                 390 cag tgt act tcc aca ggc atg cca gtc cat atg caa agc cga tct atg    1612
Gln Cys Thr Ser Thr Gly Met Pro Val His Met Gln Ser Arg Ser Met
        395                 400                 405 tta aga cca ctg gag cta gcc tta cct aat caa gcc tca tat tcg gaa    1660
Leu Arg Pro Leu Glu Leu Ala Leu Pro Asn Gln Ala Ser Tyr Ser Glu
    410                 415                 420 aac gaa att tta aag aaa gaa tta gaa gca atg aga act ttc tgt gat    1708
Asn Glu Ile Leu Lys Lys Glu Leu Glu Ala Met Arg Thr Phe Cys Asp
425                 430                 435 tca gca aaa caa gac aga ctc aaa ctc caa aat gaa ctg gct cac aag    1756
Ser Ala Lys Gln Asp Arg Leu Lys Leu Gln Asn Glu Leu Ala His Lys
440                 445                 450                 455 gtg gcg gag tgc aag gcc tta gca ttg gaa tgt gaa agg gtg aaa gag    1804
Val Ala Glu Cys Lys Ala Leu Ala Leu Glu Cys Glu Arg Val Lys Glu
            460                 465                 470 gat tca gat gag cag ata aag caa cta gaa gat gcc ttg aaa gac gtg    1852
Asp Ser Asp Glu Gln Ile Lys Gln Leu Glu Asp Ala Leu Lys Asp Val
        475                 480                 485 cag aag aga atg tat gag tcg gaa ggt aaa gtg aaa caa atg cag aca    1900
Gln Lys Arg Met Tyr Glu Ser Glu Gly Lys Val Lys Gln Met Gln Thr
    490                 495                 500 cat ttt ctt gcc ttg aaa gag cac ctg aca agt gat gcg gcc act ggg    1948
His Phe Leu Ala Leu Lys Glu His Leu Thr Ser Asp Ala Ala Thr Gly
505                 510                 515 aac cac agg ctg atg gag gaa ctg aag gat cag ttg aaa gac atg aaa    1996
Asn His Arg Leu Met Glu Glu Leu Lys Asp Gln Leu Lys Asp Met Lys
520                 525                 530                 535 gtg aaa tac gaa ggt gcg tcc gca gaa gtg ggg aaa ttg aga aac caa    2044
Val Lys Tyr Glu Gly Ala Ser Ala Glu Val Gly Lys Leu Arg Asn Gln
            540                 545                 550 atc aaa caa aat gaa atg tta gtt gaa gag ttt aag aga gat gag ggc    2092
Ile Lys Gln Asn Glu Met Leu Val Glu Glu Phe Lys Arg Asp Glu Gly
        555                 560                 565 aag ctg atg gaa gag aat aag cga ctg cag aag gag ttg agc atg tgt    2140
Lys Leu Met Glu Glu Asn Lys Arg Leu Gln Lys Glu Leu Ser Met Cys
    570                 575                 580 gaa ctg gag cga gag aag aga gga agg aag ctc act gag atg gaa ggc    2188
Glu Leu Glu Arg Glu Lys Arg Gly Arg Lys Leu Thr Glu Met Glu Gly
585                 590                 595 cag tta aag gac ttg tca gcc aag ctg gcc ctt tct att cca gca gag    2236
Gln Leu Lys Asp Leu Ser Ala Lys Leu Ala Leu Ser Ile Pro Ala Glu
600                 605                 610                 615 aaa ttt gaa aac atg aag agc ttg tta tca aat gaa ctg aac gag aag    2284
Lys Phe Glu Asn Met Lys Ser Leu Leu Ser Asn Glu Leu Asn Glu Lys
```

-continued

| | | | | |
|---|---|---|---|---|
| | 620 | 625 | 630 | |
| gca aaa aaa tta ata gat gtg gaa aga gaa tat gaa aga tca ctt aat<br>Ala Lys Lys Leu Ile Asp Val Glu Arg Glu Tyr Glu Arg Ser Leu Asn<br>635 640 645 | | | | 2332 |
| gaa act aga cca tta aag aga gaa ctt gag aat ttg aag gcc aaa ctg<br>Glu Thr Arg Pro Leu Lys Arg Glu Leu Glu Asn Leu Lys Ala Lys Leu<br>650 655 660 | | | | 2380 |
| gct cag cac gtc aaa cca gag gaa cat gag cag ctc aag agc aga tta<br>Ala Gln His Val Lys Pro Glu Glu His Glu Gln Leu Lys Ser Arg Leu<br>665 670 675 | | | | 2428 |
| gag cag aag tca gga gaa ctt ggg aag agg atc act gag tta aca tcg<br>Glu Gln Lys Ser Gly Glu Leu Gly Lys Arg Ile Thr Glu Leu Thr Ser<br>680 685 690 695 | | | | 2476 |
| aaa aat cag acg tta caa aag gaa atc gaa aag gtc tgc ctg gat aat<br>Lys Asn Gln Thr Leu Gln Lys Glu Ile Glu Lys Val Cys Leu Asp Asn<br>700 705 710 | | | | 2524 |
| aag ctc ctt aca caa caa gta aat aac tta aca act gaa atg aaa aat<br>Lys Leu Leu Thr Gln Gln Val Asn Asn Leu Thr Thr Glu Met Lys Asn<br>715 720 725 | | | | 2572 |
| gtc cct tta aaa gta agt gaa gaa atg aaa aag tca cat gat gta att<br>Val Pro Leu Lys Val Ser Glu Glu Met Lys Lys Ser His Asp Val Ile<br>730 735 740 | | | | 2620 |
| gtt gat gat ttg aat aaa aag ctt tca gat gtg aca cac aaa tat aca<br>Val Asp Asp Leu Asn Lys Lys Leu Ser Asp Val Thr His Lys Tyr Thr<br>745 750 755 | | | | 2668 |
| gaa aag aag ttg gaa atg gag aag ttg ctt atg gaa aat gcc agt tta<br>Glu Lys Lys Leu Glu Met Glu Lys Leu Leu Met Glu Asn Ala Ser Leu<br>760 765 770 775 | | | | 2716 |
| agt aaa aat gtc agc cgc ctg gaa act gtg ttc ata cct ccc gag aga<br>Ser Lys Asn Val Ser Arg Leu Glu Thr Val Phe Ile Pro Pro Glu Arg<br>780 785 790 | | | | 2764 |
| cac gaa aaa gaa atg atg gct ctg aaa tcc aat atc act gaa ctt aag<br>His Glu Lys Glu Met Met Ala Leu Lys Ser Asn Ile Thr Glu Leu Lys<br>795 800 805 | | | | 2812 |
| aag cag ctg tct gaa ctt aat aaa aaa tgt ggt gaa gac caa gag aaa<br>Lys Gln Leu Ser Glu Leu Asn Lys Lys Cys Gly Glu Asp Gln Glu Lys<br>810 815 820 | | | | 2860 |
| ata tat tca ctc atg tct gaa aac aat gat ttg aaa aag acc atg agt<br>Ile Tyr Ser Leu Met Ser Glu Asn Asn Asp Leu Lys Lys Thr Met Ser<br>825 830 835 | | | | 2908 |
| cat cag tat gtg ccc gtg aaa acc cat gaa gag att aaa act gcc ttg<br>His Gln Tyr Val Pro Val Lys Thr His Glu Glu Ile Lys Thr Ala Leu<br>840 845 850 855 | | | | 2956 |
| agt agc aca ttg gat aaa acc aat aga gaa tta gta gat gtg aag aag<br>Ser Ser Thr Leu Asp Lys Thr Asn Arg Glu Leu Val Asp Val Lys Lys<br>860 865 870 | | | | 3004 |
| aag tgt gaa gat ata aat caa gaa ttt gtg aaa ata aaa gat gag aac<br>Lys Cys Glu Asp Ile Asn Gln Glu Phe Val Lys Ile Lys Asp Glu Asn<br>875 880 885 | | | | 3052 |
| gaa ata tta aaa aga aat ctg gag aac act cag aac caa gta aaa gct<br>Glu Ile Leu Lys Arg Asn Leu Glu Asn Thr Gln Asn Gln Val Lys Ala<br>890 895 900 | | | | 3100 |
| gag tac atc agc cta aga gag cat gaa gaa aag atg agt ggc cta agg<br>Glu Tyr Ile Ser Leu Arg Glu His Glu Glu Lys Met Ser Gly Leu Arg<br>905 910 915 | | | | 3148 |
| aag agc atg aag aag gtc cag gac aac agc gct gaa ata ctg gct aag<br>Lys Ser Met Lys Lys Val Gln Asp Asn Ser Ala Glu Ile Leu Ala Lys<br>920 925 930 935 | | | | 3196 |
| tac aaa aaa agc cag gag gag att gtc acc ctg cat gag gag att gca | | | | 3244 |

```
Tyr Lys Lys Ser Gln Glu Glu Ile Val Thr Leu His Glu Glu Ile Ala
                940                 945                 950 gcc cag aag aga gaa ctc gac acg ata cag gaa tgc atc aag cta aaa       3292
Ala Gln Lys Arg Glu Leu Asp Thr Ile Gln Glu Cys Ile Lys Leu Lys
            955                 960                 965 tat gct ccg atc atc agc ttg gaa gag tgt gag aga aaa ttt aaa gcc       3340
Tyr Ala Pro Ile Ile Ser Leu Glu Glu Cys Glu Arg Lys Phe Lys Ala
        970                 975                 980 act gag aaa gaa cta aaa gaa cag cta tcc cag cag aca cag aag tat       3388
Thr Glu Lys Glu Leu Lys Glu Gln Leu Ser Gln Gln Thr Gln Lys Tyr
    985                 990                 995 aat acc agt gaa gaa gag gcc aag aag tgc aag caa gag aat gac aag       3436
Asn Thr Ser Glu Glu Glu Ala Lys Lys Cys Lys Gln Glu Asn Asp Lys
1000                1005                1010                1015 tta aag aag gag atc ctc act ctt cag aag gat cta aag gat aag aat       3484
Leu Lys Lys Glu Ile Leu Thr Leu Gln Lys Asp Leu Lys Asp Lys Asn
                1020                1025                1030 gtt cac att gag aat tct tat gaa aca gaa aga gca tta agc aga aaa       3532
Val His Ile Glu Asn Ser Tyr Glu Thr Glu Arg Ala Leu Ser Arg Lys
            1035                1040                1045 aca gaa gag ctg aac aga cag tta aaa gac ctg ttg cag aaa tac aca       3580
Thr Glu Glu Leu Asn Arg Gln Leu Lys Asp Leu Leu Gln Lys Tyr Thr
        1050                1055                1060 gag gca aag aag gag aaa gag aag ctc gtg gag gaa aat gcc aag cag       3628
Glu Ala Lys Lys Glu Lys Glu Lys Leu Val Glu Glu Asn Ala Lys Gln
    1065                1070                1075 act tct gag atc ctt gca gca caa act ctt ttg cag aag cag cat gtt       3676
Thr Ser Glu Ile Leu Ala Ala Gln Thr Leu Leu Gln Lys Gln His Val
1080                1085                1090                1095 ccg ctg gag cag gtt gag tcc ctg aaa aaa tct ctt agt ggt aca atc       3724
Pro Leu Glu Gln Val Glu Ser Leu Lys Lys Ser Leu Ser Gly Thr Ile
                1100                1105                1110 gag aca ctc aag gaa gaa ctg aaa act aag cag aga tgt tat gag aaa       3772
Glu Thr Leu Lys Glu Glu Leu Lys Thr Lys Gln Arg Cys Tyr Glu Lys
            1115                1120                1125 gag cag cag aca gtg acc caa ctg cgg cag atg ctg gag aat cag aag       3820
Glu Gln Gln Thr Val Thr Gln Leu Arg Gln Met Leu Glu Asn Gln Lys
        1130                1135                1140 aac tcc tct gtg ccc ctg gct gag cat ttg cag gtt aag gaa gca ttt       3868
Asn Ser Ser Val Pro Leu Ala Glu His Leu Gln Val Lys Glu Ala Phe
    1145                1150                1155 gag aaa gaa gtt gga atc ata aaa gct agc ttg aga gaa aag gaa gaa       3916
Glu Lys Glu Val Gly Ile Ile Lys Ala Ser Leu Arg Glu Lys Glu Glu
1160                1165                1170                1175 gaa agc caa aac aaa act gaa gag gtc tcc aaa ctc cag tct gag att       3964
Glu Ser Gln Asn Lys Thr Glu Glu Val Ser Lys Leu Gln Ser Glu Ile
                1180                1185                1190 cag aat act aaa caa gcg tta aaa aaa tta gag act cgg gag gtg gtt       4012
Gln Asn Thr Lys Gln Ala Leu Lys Lys Leu Glu Thr Arg Glu Val Val
            1195                1200                1205 gat ttg tcg aaa tat aaa gca acg aaa agc gat ttg gag aca cag att       4060
Asp Leu Ser Lys Tyr Lys Ala Thr Lys Ser Asp Leu Glu Thr Gln Ile
        1210                1215                1220 tcc gac tta aac gaa aaa ttg gcc aat ctg aat agg aag tat gag gaa       4108
Ser Asp Leu Asn Glu Lys Leu Ala Asn Leu Asn Arg Lys Tyr Glu Glu
    1225                1230                1235 gta tgt gag gag gtt ttg cat gcc aaa aag aag gaa ctg tct gct aaa       4156
Val Cys Glu Glu Val Leu His Ala Lys Lys Lys Glu Leu Ser Ala Lys
1240                1245                1250                1255
```

```
gat gag aag gaa ttg ctc cat ttc agc ata gag caa gaa atc aaa gat      4204
Asp Glu Lys Glu Leu Leu His Phe Ser Ile Glu Gln Glu Ile Lys Asp
                1260                1265                1270 cag cag gaa cga tgt gac aaa tcc tta aca acc atc acg gag cta cag      4252
Gln Gln Glu Arg Cys Asp Lys Ser Leu Thr Thr Ile Thr Glu Leu Gln
                1275                1280                1285 aga aga ata cag gaa tct gcc aaa caa atc gaa gca aaa gat aat aag      4300
Arg Arg Ile Gln Glu Ser Ala Lys Gln Ile Glu Ala Lys Asp Asn Lys
                1290                1295                1300 ata act gaa ctg ctc aat gat gtg gag aga tta aaa cag gcc ctc aat      4348
Ile Thr Glu Leu Leu Asn Asp Val Glu Arg Leu Lys Gln Ala Leu Asn
                1305                1310                1315 ggc ctt tcc cag ctc acc tat gga agt ggg agt ccc agc aag agg cag      4396
Gly Leu Ser Gln Leu Thr Tyr Gly Ser Gly Ser Pro Ser Lys Arg Gln
1320                1325                1330                1335 agt cag ctg att gac agc ctg cag cag cag gtc agg tcc ctg cag cag      4444
Ser Gln Leu Ile Asp Ser Leu Gln Gln Gln Val Arg Ser Leu Gln Gln
                1340                1345                1350 cag ctg gcg gat gcc gac aga cag cac caa gaa gta att gca att tat      4492
Gln Leu Ala Asp Ala Asp Arg Gln His Gln Glu Val Ile Ala Ile Tyr
                1355                1360                1365 cgg aca cac ctt ctt agt gct gca cag ggt cac atg gat gag gat gtg      4540
Arg Thr His Leu Leu Ser Ala Ala Gln Gly His Met Asp Glu Asp Val
                1370                1375                1380 cag gcc gcc tta ctg cag atc ata cag atg cgg cag ggg ctc gtg tgc      4588
Gln Ala Ala Leu Leu Gln Ile Ile Gln Met Arg Gln Gly Leu Val Cys
                1385                1390                1395 tag tcg gca ccccccagcc cacagtggct ttccctgctg gtgctgagca              4637
 *  Ser Ala
     1400 ttctgtgcgc aacttcatgg cctttctggg cctcgctgtg ctagtataat taaaataaag   4697 tgtattttga tccatcaaaa aaaaaaaaaa aaa                                 4730

<210> SEQ ID NO 2
<211> LENGTH: 1401
<212> TYPE: PRT
<213> ORGANISM: Bos taurus

<400> SEQUENCE: 2

Met Met Ser Cys Trp Phe Ser Cys Ala Pro Lys Asn Arg Gln Ala Ala
  1               5                  10                  15

Asp Trp Asn Lys Tyr Asp Asp Arg Leu Met Arg Ala Ala Glu Arg Gly
                 20                  25                  30

Asp Val Glu Lys Val Ser Ser Ile Leu Ala Lys Lys Gly Val Asn Pro
             35                  40                  45

Gly Lys Leu Asp Val Glu Gly Arg Ser Ala Phe His Val Val Ala Ser
         50                  55                  60

Lys Gly Asn Leu Glu Cys Leu Asn Ala Ile Leu Ile His Gly Val Asp
 65                  70                  75                  80

Ile Thr Thr Ser Asp Thr Ala Gly Arg Asn Ala Leu His Leu Ala Ala
                 85                  90                  95

Lys Tyr Gly His Ala Leu Cys Leu Gln Lys Leu Leu Gln Tyr Asn Cys
            100                 105                 110

Pro Thr Glu His Val Asp Leu Gln Gly Arg Thr Ala Leu His Asp Ala
        115                 120                 125

Ala Met Ala Asp Cys Pro Ser Ser Ile Gln Leu Leu Cys Asp His Gly
    130                 135                 140
```

-continued

```
Ala Ser Val Asn Ala Lys Asp Val Asp Gly Arg Thr Pro Leu Val Leu
145                 150                 155                 160

Ala Thr Gln Met Cys Arg Pro Thr Ile Cys Gln Leu Leu Ile Asp Arg
                165                 170                 175

Gly Ala Asp Ile Asn Ser Arg Asp Lys Gln Asn Arg Thr Ala Leu Met
            180                 185                 190

Leu Gly Cys Glu Tyr Gly Cys Lys Asp Ala Val Glu Val Leu Ile Lys
        195                 200                 205

Asn Gly Ala Asp Val Thr Leu Leu Asp Ala Leu Gly His Asp Ser Ser
    210                 215                 220

Tyr Tyr Ala Arg Ile Gly Asp Asn Leu Asp Ile Leu Thr Leu Leu Lys
225                 230                 235                 240

Thr Ala Ser Glu Asn Ser Asn Lys Gly Arg Glu Leu Trp Lys Lys Gly
                245                 250                 255

Pro Ser Leu Gln Gln Arg Asn Leu Ser Gln Met Leu Asp Glu Val Asn
            260                 265                 270

Thr Lys Ser Asn Gln Arg Glu His Gln Asn Ile Gln Asp Leu Glu Ile
        275                 280                 285

Glu Asn Glu Asp Leu Lys Glu Arg Leu Arg Lys Ile Gln Gln Glu Gln
    290                 295                 300

Arg Ile Leu Leu Asp Lys Val Asn Gly Leu Gln Leu Gln Leu Asn Glu
305                 310                 315                 320

Glu Val Met Val Ala Asp Asp Leu Glu Ser Glu Lys Glu Lys Leu Lys
                325                 330                 335

Ser Leu Leu Ala Ala Lys Glu Lys Gln His Glu Glu Ser Leu Arg Thr
            340                 345                 350

Ile Glu Ala Leu Lys Ser Arg Phe Lys Tyr Phe Glu Ser Asp His Leu
        355                 360                 365

Gly Ser Gly Ser His Phe Arg Lys Glu Asp Met Leu Leu Lys Gln Gly
    370                 375                 380

Gln Met Tyr Met Thr Asp Ser Gln Cys Thr Ser Thr Gly Met Pro Val
385                 390                 395                 400

His Met Gln Ser Arg Ser Met Leu Arg Pro Leu Glu Leu Ala Leu Pro
                405                 410                 415

Asn Gln Ala Ser Tyr Ser Glu Asn Glu Ile Leu Lys Lys Glu Leu Glu
            420                 425                 430

Ala Met Arg Thr Phe Cys Asp Ser Ala Lys Gln Asp Arg Leu Lys Leu
        435                 440                 445

Gln Asn Glu Leu Ala His Lys Val Ala Glu Cys Lys Ala Leu Ala Leu
    450                 455                 460

Glu Cys Glu Arg Val Lys Glu Asp Ser Asp Glu Gln Ile Lys Gln Leu
465                 470                 475                 480

Glu Asp Ala Leu Lys Asp Val Gln Lys Arg Met Tyr Glu Ser Glu Gly
                485                 490                 495

Lys Val Lys Gln Met Gln Thr His Phe Leu Ala Leu Lys Glu His Leu
            500                 505                 510

Thr Ser Asp Ala Ala Thr Gly Asn His Arg Leu Met Glu Glu Leu Lys
        515                 520                 525

Asp Gln Leu Lys Asp Met Lys Val Lys Tyr Glu Gly Ala Ser Ala Glu
    530                 535                 540

Val Gly Lys Leu Arg Asn Gln Ile Lys Gln Asn Glu Met Leu Val Glu
545                 550                 555                 560

Glu Phe Lys Arg Asp Glu Gly Lys Leu Met Glu Glu Asn Lys Arg Leu
```

-continued

```
              565                 570                 575
Gln Lys Glu Leu Ser Met Cys Glu Leu Glu Arg Glu Lys Arg Gly Arg
              580                 585                 590
Lys Leu Thr Glu Met Glu Gly Gln Leu Lys Asp Leu Ser Ala Lys Leu
              595                 600                 605
Ala Leu Ser Ile Pro Ala Glu Lys Phe Glu Asn Met Lys Ser Leu Leu
              610                 615                 620
Ser Asn Glu Leu Asn Glu Lys Ala Lys Lys Leu Ile Asp Val Glu Arg
625                 630                 635                 640
Glu Tyr Glu Arg Ser Leu Asn Glu Thr Arg Pro Leu Lys Arg Glu Leu
              645                 650                 655
Glu Asn Leu Lys Ala Lys Leu Ala Gln His Val Lys Pro Glu Glu His
              660                 665                 670
Glu Gln Leu Lys Ser Arg Leu Glu Gln Lys Ser Gly Glu Leu Gly Lys
              675                 680                 685
Arg Ile Thr Glu Leu Thr Ser Lys Asn Gln Thr Leu Gln Lys Glu Ile
              690                 695                 700
Glu Lys Val Cys Leu Asp Asn Lys Leu Leu Thr Gln Gln Val Asn Asn
705                 710                 715                 720
Leu Thr Thr Glu Met Lys Asn Val Pro Leu Lys Val Ser Glu Glu Met
              725                 730                 735
Lys Lys Ser His Asp Val Ile Val Asp Asp Leu Asn Lys Lys Leu Ser
              740                 745                 750
Asp Val Thr His Lys Tyr Thr Glu Lys Lys Leu Glu Met Glu Lys Leu
              755                 760                 765
Leu Met Glu Asn Ala Ser Leu Ser Lys Asn Val Ser Arg Leu Glu Thr
              770                 775                 780
Val Phe Ile Pro Pro Glu Arg His Glu Lys Glu Met Met Ala Leu Lys
785                 790                 795                 800
Ser Asn Ile Thr Glu Leu Lys Lys Gln Leu Ser Glu Leu Asn Lys Lys
              805                 810                 815
Cys Gly Glu Asp Gln Glu Lys Ile Tyr Ser Leu Met Ser Glu Asn Asn
              820                 825                 830
Asp Leu Lys Lys Thr Met Ser His Gln Tyr Val Pro Val Lys Thr His
              835                 840                 845
Glu Glu Ile Lys Thr Ala Leu Ser Ser Thr Leu Asp Lys Thr Asn Arg
              850                 855                 860
Glu Leu Val Asp Val Lys Lys Lys Cys Glu Asp Ile Asn Gln Glu Phe
865                 870                 875                 880
Val Lys Ile Lys Asp Glu Asn Glu Ile Leu Lys Arg Asn Leu Glu Asn
              885                 890                 895
Thr Gln Asn Gln Val Lys Ala Glu Tyr Ile Ser Leu Arg Glu His Glu
              900                 905                 910
Glu Lys Met Ser Gly Leu Arg Lys Ser Met Lys Lys Val Gln Asp Asn
              915                 920                 925
Ser Ala Glu Ile Leu Ala Lys Tyr Lys Lys Ser Gln Glu Glu Ile Val
              930                 935                 940
Thr Leu His Glu Glu Ile Ala Ala Gln Lys Arg Glu Leu Asp Thr Ile
945                 950                 955                 960
Gln Glu Cys Ile Lys Leu Lys Tyr Ala Pro Ile Ile Ser Leu Glu Glu
              965                 970                 975
Cys Glu Arg Lys Phe Lys Ala Thr Glu Lys Glu Leu Lys Glu Gln Leu
              980                 985                 990
```

-continued

```
Ser Gln Gln Thr Gln Lys Tyr Asn Thr Ser Glu Glu Ala Lys Lys
        995                 1000                1005

Cys Lys Gln Glu Asn Asp Lys Leu Lys Lys Glu Ile Leu Thr Leu Gln
        1010                1015                1020

Lys Asp Leu Lys Asp Lys Asn Val His Ile Glu Asn Ser Tyr Glu Thr
1025                1030                1035                1040

Glu Arg Ala Leu Ser Arg Lys Thr Glu Glu Leu Asn Arg Gln Leu Lys
                1045                1050                1055

Asp Leu Leu Gln Lys Tyr Thr Glu Ala Lys Lys Glu Lys Glu Lys Leu
                1060                1065                1070

Val Glu Glu Asn Ala Lys Gln Thr Ser Glu Ile Leu Ala Ala Gln Thr
            1075                1080                1085

Leu Leu Gln Lys Gln His Val Pro Leu Glu Gln Val Glu Ser Leu Lys
        1090                1095                1100

Lys Ser Leu Ser Gly Thr Ile Glu Thr Leu Lys Glu Glu Leu Lys Thr
1105                1110                1115                1120

Lys Gln Arg Cys Tyr Glu Lys Glu Gln Gln Thr Val Thr Gln Leu Arg
                1125                1130                1135

Gln Met Leu Glu Asn Gln Lys Asn Ser Ser Val Pro Leu Ala Glu His
                1140                1145                1150

Leu Gln Val Lys Glu Ala Phe Glu Lys Glu Val Gly Ile Ile Lys Ala
            1155                1160                1165

Ser Leu Arg Glu Lys Glu Glu Glu Ser Gln Asn Lys Thr Glu Glu Val
        1170                1175                1180

Ser Lys Leu Gln Ser Glu Ile Gln Asn Thr Lys Gln Ala Leu Lys Lys
1185                1190                1195                1200

Leu Glu Thr Arg Glu Val Val Asp Leu Ser Lys Tyr Lys Ala Thr Lys
                1205                1210                1215

Ser Asp Leu Glu Thr Gln Ile Ser Asp Leu Asn Glu Lys Leu Ala Asn
                1220                1225                1230

Leu Asn Arg Lys Tyr Glu Glu Val Cys Glu Glu Val Leu His Ala Lys
            1235                1240                1245

Lys Lys Glu Leu Ser Ala Lys Asp Glu Lys Glu Leu Leu His Phe Ser
1250                1255                1260

Ile Glu Gln Glu Ile Lys Asp Gln Gln Glu Arg Cys Asp Lys Ser Leu
1265                1270                1275                1280

Thr Thr Ile Thr Glu Leu Gln Arg Arg Ile Gln Glu Ser Ala Lys Gln
                1285                1290                1295

Ile Glu Ala Lys Asp Asn Lys Ile Thr Glu Leu Leu Asn Asp Val Glu
            1300                1305                1310

Arg Leu Lys Gln Ala Leu Asn Gly Leu Ser Gln Leu Thr Tyr Gly Ser
        1315                1320                1325

Gly Ser Pro Ser Lys Arg Gln Ser Gln Leu Ile Asp Ser Leu Gln Gln
        1330                1335                1340

Gln Val Arg Ser Leu Gln Gln Gln Leu Ala Asp Ala Asp Arg Gln His
1345                1350                1355                1360

Gln Glu Val Ile Ala Ile Tyr Arg Thr His Leu Leu Ser Ala Ala Gln
                1365                1370                1375

Gly His Met Asp Glu Asp Val Gln Ala Ala Leu Leu Gln Ile Ile Gln
            1380                1385                1390

Met Arg Gln Gly Leu Val Cys Ser Ala
        1395                1400
```

<210> SEQ ID NO 3
<211> LENGTH: 4206
<212> TYPE: DNA
<213> ORGANISM: Bos taurus

<400> SEQUENCE: 3

| | | | | | |
|---|---|---|---|---|---|
| atgatgagct | gttggttttc | ttgtgctcct | aagaacagac | aagcagcaga | ttggaacaaa | 60 |
| tacgatgacc | gattgatgag | agcagcagaa | agggagatg | tagaaaaagt | gtcctcaatc | 120 |
| cttgctaaaa | agggagtcaa | tccaggcaag | ctagatgtag | aaggcagatc | tgcctttcat | 180 |
| gttgtggcct | caagggaaa | tcttgagtgt | ttgaatgcca | tcctcataca | tggagttgat | 240 |
| attacaacca | gtgacaccgc | aggaaggaat | gctcttcacc | tggctgcaaa | gtatgggcat | 300 |
| gcactgtgtc | tacaaaaact | tctacagtac | aattgtccca | ctgaacatgt | agacctgcag | 360 |
| ggaagaactg | cacttcatga | tgcagctatg | gcagactgtc | cttctagcat | acagctgctc | 420 |
| tgcgaccatg | gggcctcggt | gaatgccaaa | gatgtagatg | gcggacacc | acttgttctg | 480 |
| gctacccaga | tgtgtaggcc | aacaatatgt | caactgctga | tagatagagg | ggcggatatt | 540 |
| aattccagag | acaaacaaaa | caggactgct | ctcatgctag | gatgcgagta | tggttgcaaa | 600 |
| gatgcagtag | aagtcttaat | caaaaacggc | gctgacgtga | ccttgctgga | cgcccttggc | 660 |
| catgacagtt | cttactatgc | aagaattggt | gacaatctgg | acattctaac | cttactgaag | 720 |
| actgcatcag | aaaattccaa | caagggaga | gaactttgga | agaaaggacc | atctttacaa | 780 |
| cagcgaaatt | tgtctcagat | gctagatgaa | gtaaatacga | agtcaaatca | gagggagcat | 840 |
| caaaacattc | aggatctgga | gattgaaaat | gaagatctga | agagagatt | gagaaaaatt | 900 |
| cagcaagaac | agagaatatt | attggataaa | gtcaatggtt | tacagctaca | gctgaatgag | 960 |
| gaagtaatgg | tggctgatga | tctggaaagt | gagaaagaaa | agctgaagtc | ccttttggca | 1020 |
| gccaaagaaa | agcagcatga | agaaagccta | gaactattg | aggctctgaa | agtagatt | 1080 |
| aagtattttg | agagtgatca | tttaggatca | ggaagtcatt | tcaggaaaga | agatatgctt | 1140 |
| cttaaacaag | gtcaaatgta | catgacagac | tcacagtgta | cttccacagg | catgccagtc | 1200 |
| catatgcaaa | gccgatctat | gttaagacca | ctggagctag | ccttacctaa | tcaagcctca | 1260 |
| tattcggaaa | acgaaatttt | aaagaaagaa | ttagaagcaa | tgagaacttt | ctgtgattca | 1320 |
| gcaaaacaag | acagactcaa | actccaaaat | gaactggctc | acaaggtggc | ggagtgcaag | 1380 |
| gccttagcat | tggaatgtga | aagggtgaaa | gaggattcag | atgagcagat | aaagcaacta | 1440 |
| gaagatgcct | tgaaagacgt | gcagaagaga | atgtatgagt | cggaaggtaa | agtgaaacaa | 1500 |
| atgcagacac | attttcttgc | cttgaaagag | cacctgacaa | gtgatgcggc | cactgggaac | 1560 |
| cacaggctga | tggaggaact | gaaggatcag | ttgaaagaca | tgaaagtgaa | atacgaaggt | 1620 |
| gcgtccgcag | aagtggggaa | attgagaaac | caaatcaaac | aaaatgaaat | gttagttgaa | 1680 |
| gagtttaaga | gagatgaggg | caagctgatg | aagagaata | agcgactgca | gaaggagttg | 1740 |
| agcatgtgtg | aactggagcg | agagaagaga | ggaaggaagc | tcactgagat | ggaaggccag | 1800 |
| ttaaaggact | tgtcagccaa | gctggccctt | tctattccag | cagagaaatt | tgaaacatg | 1860 |
| aagagcttgt | tatcaaatga | actgaacgag | aaggcaaaaa | aattaataga | tgtggaaaga | 1920 |
| gaatatgaaa | gatcacttaa | tgaaactaga | ccattaaaga | gagaacttga | gaatttgaag | 1980 |
| gccaaactgg | ctcagcacgt | caaaccagag | gaacatgagc | agctcaagag | cagattagag | 2040 |
| cagaagtcag | gagaacttgg | gaagaggatc | actgagttaa | catcgaaaaa | tcagacgtta | 2100 |
| caaaaggaaa | tcgaaaaggt | ctgcctggat | aataagctcc | ttacacaaca | agtaaataac | 2160 |

-continued

```
ttaacaactg aaatgaaaaa tgtccctta aaagtaagtg aagaaatgaa aaagtcacat    2220
gatgtaattg ttgatgattt gaataaaaag ctttcagatg tgacacacaa atatacagaa    2280
aagaagttgg aaatggagaa gttgcttatg gaaaatgcca gtttaagtaa aaatgtcagc    2340
cgcctggaaa ctgtgttcat acctcccgag agacacgaaa aagaaatgat ggctctgaaa    2400
tccaatatca ctgaacttaa gaagcagctg tctgaactta ataaaaaatg tggtgaagac    2460
caagagaaaa tatattcact catgtctgaa acaatgatt tgaaaagac catgagtcat     2520 cagtatgtgc ccgtgaaaac ccatgaagag attaaaactg ccttgagtag cacattggat    2580
aaaaccaata gagaattagt agatgtgaag aagaagtgtg aagatataaa tcaagaattt    2640
gtgaaaataa aagatgagaa cgaaatatta aaagaaatc tggagaacac tcagaaccaa    2700
gtaaaagctg agtacatcag cctaagagag catgaagaaa agatgagtgg cctaaggaag    2760
agcatgaaga aggtccagga caacagcgct gaaatactgg ctaagtacaa aaaaagccag    2820
gaggagattg tcaccctgca tgaggagatt gcagcccaga agagagaact cgacacgata    2880
caggaatgca tcaagctaaa atatgctccg atcatcagct tggaagagtg tgagagaaaa    2940
tttaaagcca ctgagaaaga actaaaagaa cagctatccc agcagacaca gaagtataat    3000
accagtgaag aagaggccaa gaagtgcaag caagagaatg acaagttaaa gaaggagatc    3060
ctcactcttc agaaggatct aaaggataag aatgttcaca ttgagaattc ttatgaaaca    3120
gaaagagcat taagcagaaa acagaagag ctgaacagac agttaaaaga cctgttgcag    3180
aaatacacag aggcaaagaa ggagaaagag aagctcgtgg aggaaaatgc caagcagact    3240
tctgagatcc ttgcagcaca aactcttttg cagaagcagc atgttccgct ggagcaggtt    3300
gagtccctga aaaatctct tagtggtaca atcgagacac tcaaggaaga actgaaaact    3360
aagcagagat gttatgagaa agagcagcag acagtgaccc aactgcggca gatgctggag    3420
aatcagaaga actcctctgt gcccctggct gagcatttgc aggttaagga agcatttgag    3480
aaagaagttg gaatcataaa agctagcttg agagaaaagg aagaagaaag ccaaaacaaa    3540
actgaagagg tctccaaact ccagtctgag attcagaata ctaaacaagc gttaaaaaaa    3600
ttagagactc gggaggtggt tgatttgtcg aaatataaag caacgaaaag cgatttggag    3660
acacagattt ccgacttaaa cgaaaaattg gccaatctga ataggaagta tgaggaagta    3720
tgtgaggagg ttttgcatgc caaaaagaag gaactgtctg ctaaagatga aaggaattg    3780 ctccatttca gcatagagca agaaatcaaa gatcagcagg aacgatgtga caaatccta    3840 acaaccatca cggagctaca gagaagaata caggaatctg ccaaacaaat cgaagcaaaa    3900
gataataaga taactgaact gctcaatgat gtggagagat aaaacaggc cctcaatggc     3960 cttcccagc tcacctatgg aagtgggagt cccagcaaga ggcagagtca gctgattgac    4020
agcctgcagc agcaggtcag gtccctgcag cagcagctgg cggatgccga cagacagcac    4080
caagaagtaa ttgcaatta tcggacacac cttcttagtg ctgcacaggg tcacatggat    4140
gaggatgtgc aggccgcctt actgcagatc atacagatgc ggcagggct cgtgtgctag    4200 tcggca                                                               4206
```

<210> SEQ ID NO 4
<211> LENGTH: 31
<212> TYPE: PRT
<213> ORGANISM: Artificial Sequence
<220> FEATURE:
<223> OTHER INFORMATION: Motif
<220> FEATURE:

```
<221> NAME/KEY: VARIANT
<222> LOCATION: 2,7,10-11,13-15,18,19,22,23,26,27,29,30
<223> OTHER INFORMATION: Xaa may be any amino acid
<220> FEATURE:
<221> NAME/KEY: VARIANT
<222> LOCATION: 4
<223> OTHER INFORMATION: Xaa may be Pro or Ala
<220> FEATURE:
<221> NAME/KEY: VARIANT
<222> LOCATION: 16
<223> OTHER INFORMATION: Xaa may be Val or Ile
<220> FEATURE:
<221> NAME/KEY: VARIANT
<222> LOCATION: 17
<223> OTHER INFORMATION: Xaa may be Val or Ala
<220> FEATURE:
<221> NAME/KEY: VARIANT
<222> LOCATION: 31
<223> OTHER INFORMATION: Xaa may be Thr or Asp

<400> SEQUENCE: 4

Gly Xaa Thr Xaa Leu His Xaa Ala Ala Xaa Xaa Gly Xaa Xaa Xaa Xaa
 1               5                  10                  15

Xaa Xaa Xaa Leu Leu Xaa Xaa Gly Ala Xaa Xaa Asn Xaa Xaa Xaa
            20                  25                  30

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gctctaatct gctcttgagc                                              20

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
ctagtcgact gttcctctgg tttgacgtg                                    29

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tcagcctgtg gttcccagtg g                                            21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tgtcaggtgc tctttcaagg c                                            21

<210> SEQ ID NO 9
<211> LENGTH: 20
```

```
<212> TYPE: DNA
<213> ORGANISM: Artificial Sequence
<220> FEATURE:
<223> OTHER INFORMATION: Primer

<400> SEQUENCE: 9
gtagctgtaa accattgact                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
atattctctg ttcttgctga                                              20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ctagcttgcc tggattgact c                                            21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tttagcaagg attgaggaca c                                            21

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
cgggatcccc gtggaaagag aatatgaaag atca                              34

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
cgggatcccg gcacacgagc ccctgccg                                     28

<210> SEQ ID NO 15
<211> LENGTH: 34
<212> TYPE: DNA
<213> ORGANISM: Artificial Sequence
<220> FEATURE:
<223> OTHER INFORMATION: Primer

<400> SEQUENCE: 15
```

-continued cgggatcccc aattcttatg aaacagaaag agca					34

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
cgggatcccg gcacacgagc ccctgccg					28

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gaactggctc acaaggtggc					20

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ggtgacaatc tggacattct aa					22

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
tcctgtctat gatgagctgt tg					22

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
ggggtaccag tgttgaggcg gcaggat					27

<210> SEQ ID NO 21
<211> LENGTH: 47
<212> TYPE: DNA
<213> ORGANISM: Artificial Sequence
<220> FEATURE:
<223> OTHER INFORMATION: Primer

<400> SEQUENCE: 21
gctctagact agtgatggtg atggtgatgg cacacgagcc cctgccg					47

<210> SEQ ID NO 22
<211> LENGTH: 29
<212> TYPE: DNA
<213> ORGANISM: Artificial Sequence -continued

```
<220> FEATURE:
<223> OTHER INFORMATION: Primer

<400> SEQUENCE: 22
ggaattcagt ggaaagagaa tatgaaaga                                29

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
gcggatcctc aatgtgaaca ttc                                      23

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
cattgagaat tcttatgaaa cag                                      23

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
cgggatccaa ttcttatgaa acagaaagag                               30
```